US012788819B2

(12) United States Patent
Stover et al.

(10) Patent No.: US 12,788,819 B2
(45) Date of Patent: Nov. 10, 2026

(54) FORMULATED AND/OR CO-FORMULATED LIPOSOME COMPOSITIONS CONTAING TGFβ ANTAGONIST PRODRUGS USEFUL IN THE TREATMENT OF CANCER AND METHODS THEREOF

(71) Applicant: Nammi Therapeutics, Inc., Los Angeles, CA (US)

(72) Inventors: David Stover, Los Angeles, CA (US); Dhruba Bharali, Sherman Oaks, CA (US); Bruce A Hay, Niskayuna, NY (US); Tahmineh Safaie, Yucca Valley, CA (US)

(73) Assignee: Nammi Therapeutics, Inc., Los Angeles, CA (US)

( * ) Notice: Subject to any disclaimer, the term of this patent is extended or adjusted under 35 U.S.C. 154(b) by 354 days.

(21) Appl. No.: 18/445,323

(22) Filed: Jul. 10, 2023

(65) Prior Publication Data

US 2024/0050575 A1 Feb. 15, 2024

Related U.S. Application Data

(63) Continuation of application No. 17/300,063, filed on Feb. 19, 2021, now Pat. No. 11,801,304.

(51) Int. Cl.

| | |
|---|---|
| ***A61K 47/54*** | (2017.01) |
| ***A61K 9/1277*** | (2025.01) |
| ***A61K 9/51*** | (2006.01) |
| ***A61K 31/444*** | (2006.01) |
| ***A61K 45/06*** | (2006.01) |
| ***A61P 35/00*** | (2006.01) |

(52) U.S. Cl.

CPC .......... *A61K 47/543* (2017.08); *A61K 9/1277* (2013.01); *A61K 9/5192* (2013.01); *A61K 31/444* (2013.01); *A61K 45/06* (2013.01); *A61P 35/00* (2018.01)

(58) Field of Classification Search

None

See application file for complete search history.

(56) References Cited

U.S. PATENT DOCUMENTS

| | | | |
|---|---|---|---|
| 7,265,225 | B2 | 9/2007 | Beight et al. |
| 7,494,651 | B2 | 2/2009 | Jones et al. |
| 7,709,610 | B2 | 5/2010 | Williams et al. |
| 7,795,389 | B2 | 9/2010 | Sun et al. |
| 7,834,029 | B2 | 11/2010 | Beight et al. |
| 7,999,082 | B2 | 8/2011 | Holers et al. |
| 8,080,568 | B1 | 12/2011 | Kim et al. |
| 8,569,462 | B2 | 10/2013 | Bedinger et al. |
| 8,871,189 | B2 | 10/2014 | Rogers et al. |
| 8,871,744 | B2 | 10/2014 | Barbeau |
| 9,005,968 | B2 | 4/2015 | Lin et al. |
| 9,399,676 | B2 | 7/2016 | Schurpf et al. |
| 9,534,205 | B2 | 1/2017 | Shi et al. |
| 9,782,452 | B2 | 10/2017 | Scandura et al. |
| 9,889,209 | B2 | 2/2018 | Mirkin et al. |
| 10,030,229 | B2 | 7/2018 | Peterson et al. |
| 10,239,903 | B2 | 3/2019 | Benita et al. |
| 10,479,829 | B2 | 11/2019 | Van der Woning et al. |
| 10,568,883 | B2 | 2/2020 | Karp et al. |
| 11,046,729 | B2 | 6/2021 | Suto et al. |
| 2005/0245520 | A1 | 11/2005 | Dodic et al. |
| 2006/0062841 | A1 | 3/2006 | Huang et al. |
| 2013/0189780 | A1 | 7/2013 | Shoemaker et al. |
| 2017/0029778 | A1 | 2/2017 | Peterson et al. |
| 2018/0021253 | A1 | 1/2018 | Sandeep et al. |
| 2018/0071291 | A1 | 3/2018 | Stewart et al. |
| 2018/0119151 | A1 | 5/2018 | Aoki et al. |
| 2019/0125795 | A1 | 5/2019 | Rosen et al. |
| 2020/0197534 | A1 | 6/2020 | Mei et al. |

FOREIGN PATENT DOCUMENTS

| | | | | |
|---|---|---|---|---|
| EP | 2 409 708 | A1 | 1/2012 | |
| WO | WO2004/013135 | A1 | 2/2004 | |
| WO | WO2013/082389 | A1 | 6/2013 | |
| WO | WO2015/166498 | A1 | 11/2015 | |
| WO | WO2018/158727 | A1 | 9/2018 | |
| WO | WO2020/013803 | A1 | 1/2020 | |
| WO | WO 2020/257635 | A1 * | 12/2020 | ............ A61K 47/34 |

OTHER PUBLICATIONS

Gellibert et al., Journal of Medicinal Chemistry (2006), 49(7), pp. 2210-2221.*

Loomans, et al., Activin Receptor-Like Kinases: A Diverse Family Playing an Important Role in Cancer, Am. J. Cancer Res. 2016;6(11) pp. 2431-2447.

Huang, et al., Recent Progress in TGF-b Inhibitors for Cancer Therapy, Biomedicine & Pharmacotherapy 134 (2021) 111046.

Kubota, et al., Whole-organ Analysis of TGF-b-mediated Remodelling of the Tumor Microenvironment by Tissue Clearing, Comms. Bio.(2021)4:294, pp. 1-15.

Elechalawar, et al., Dual Targeting of Folate Receptor-Expressing Glioma Tumor-associated Macrophages . . . , Nanoscale Adv., 2019, 1, pp. 3555-3567.

Mura, et al., Lipid Prodrug Nanocarriers in Cancer Therapy, J. Controlled Rel., 208 (2015) pp. 25-41.

(Continued)

*Primary Examiner* — Brian J Davis

(74) *Attorney, Agent, or Firm* — LOSMP; Shane M. Popp

(57) ABSTRACT

Formulated and/or co-formulated liposomes (LNP) and solid-lipid nanoparticles (SLNP) comprising TB Prodrugs and methods of making the LNPs and SLNPs are disclosed herein. The TB prodrug compositions comprise a drug moiety, a lipid moiety, and linkage unit that inhibit ALK5. The TB Prodrugs can be formulated and/or co-formulated into a liposome or solid-lipid nanoparticle to provide a method of treating cancer, immunological disorders, and other disease by utilizing a targeted drug delivery vehicle.

22 Claims, 18 Drawing Sheets

(56) References Cited

OTHER PUBLICATIONS

Petersen, et al., Oral Administration of GW788388, an Inhibitor of TGF-b Type I and II Receptor Kinases . . . , Kidney International (2008) 73, pp. 705-715.
Zhang, et al., Biemamides A-E, Inhibitors of the TGF-b Pathway That Block the Epithelial to Mesenchymal Transition, Org Letter (Sep. 6, 2018), doi:10.1021/acs.orglett.8601871.

* cited by examiner

Figure 1. Chemical Synthesis for TB4-Prodrug
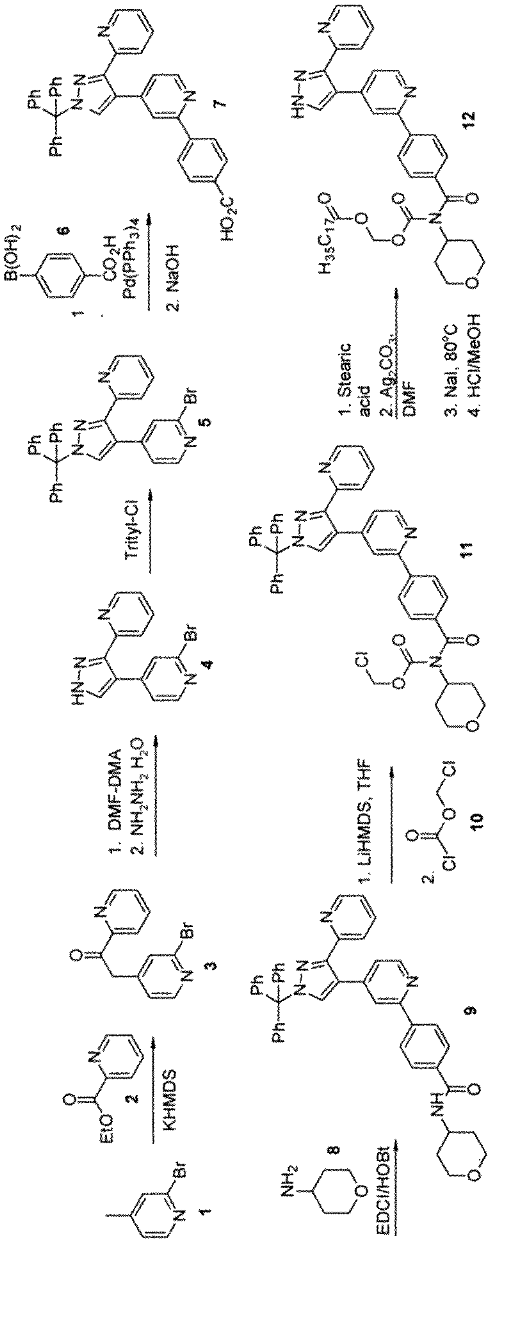
1 2 3 4 5 6 7 8 9 10 11 12

Figure 2. Chemical Synthesis for Protective Group Intermediates en route to final TB4-Prodrug
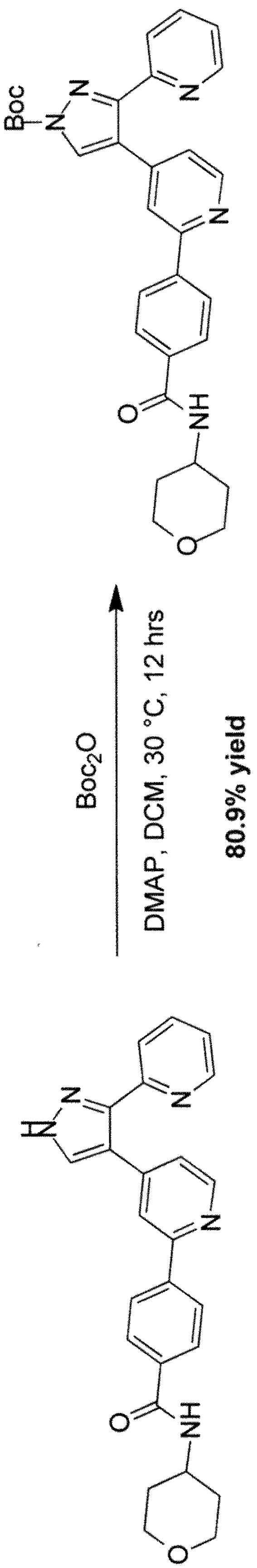
2
Mix of BOC on both pyrazole nitrogens Figure 3. Chemical Synthesis for Protective Group Intermediates en route to final TB4-Prodrug
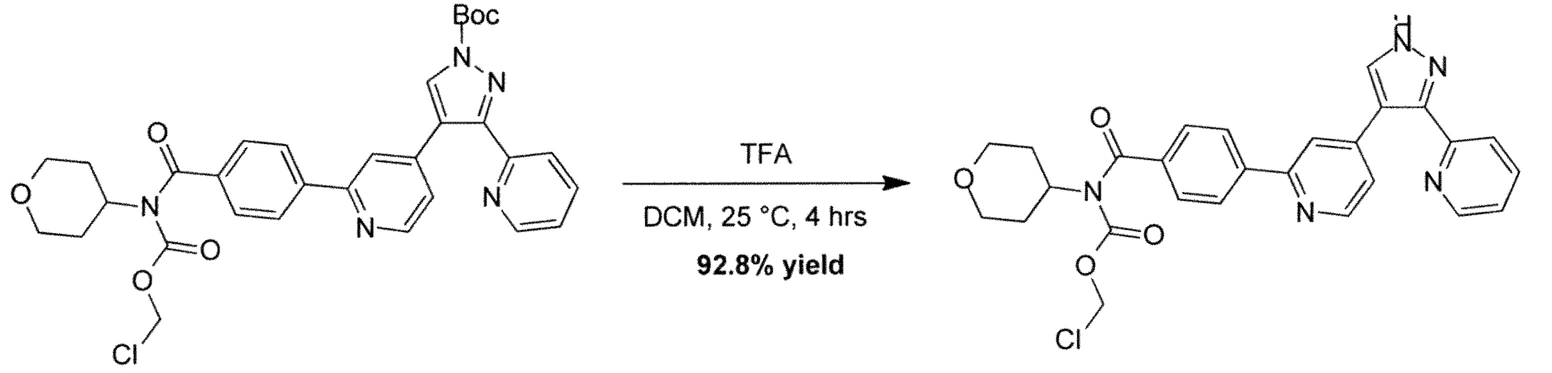
3 4

Figure 4. ALK5 Inhibitor Prodrug Synthesis Schema with Carboxylic Acid Functionality
Active Molecule with carboxylic acid functionality
Prodrug Structure Cleaved by Esterases
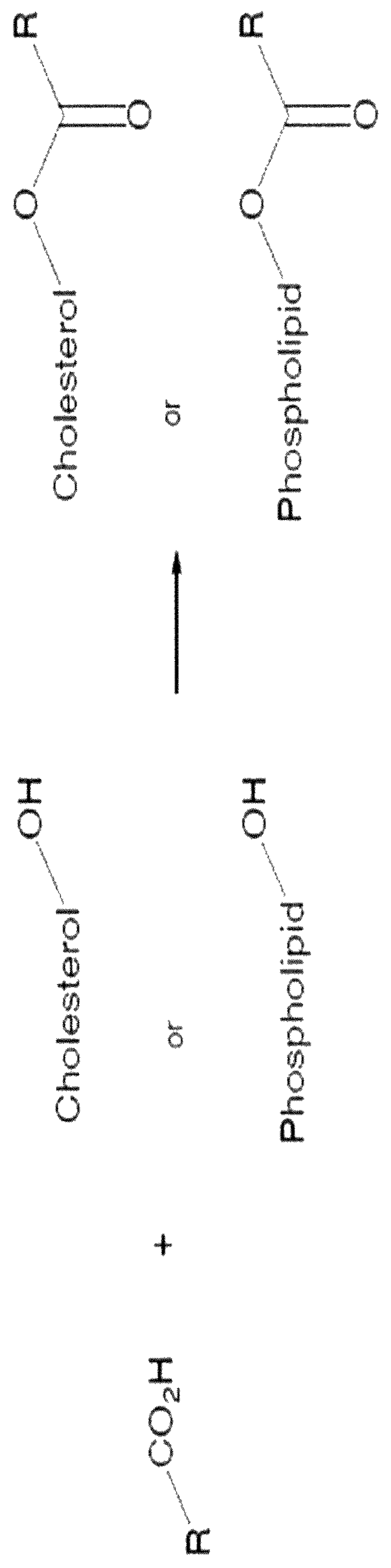
or
or Figure 5. ALK5 Inhibitor Prodrug Synthesis Schema with Alcohol Functionality
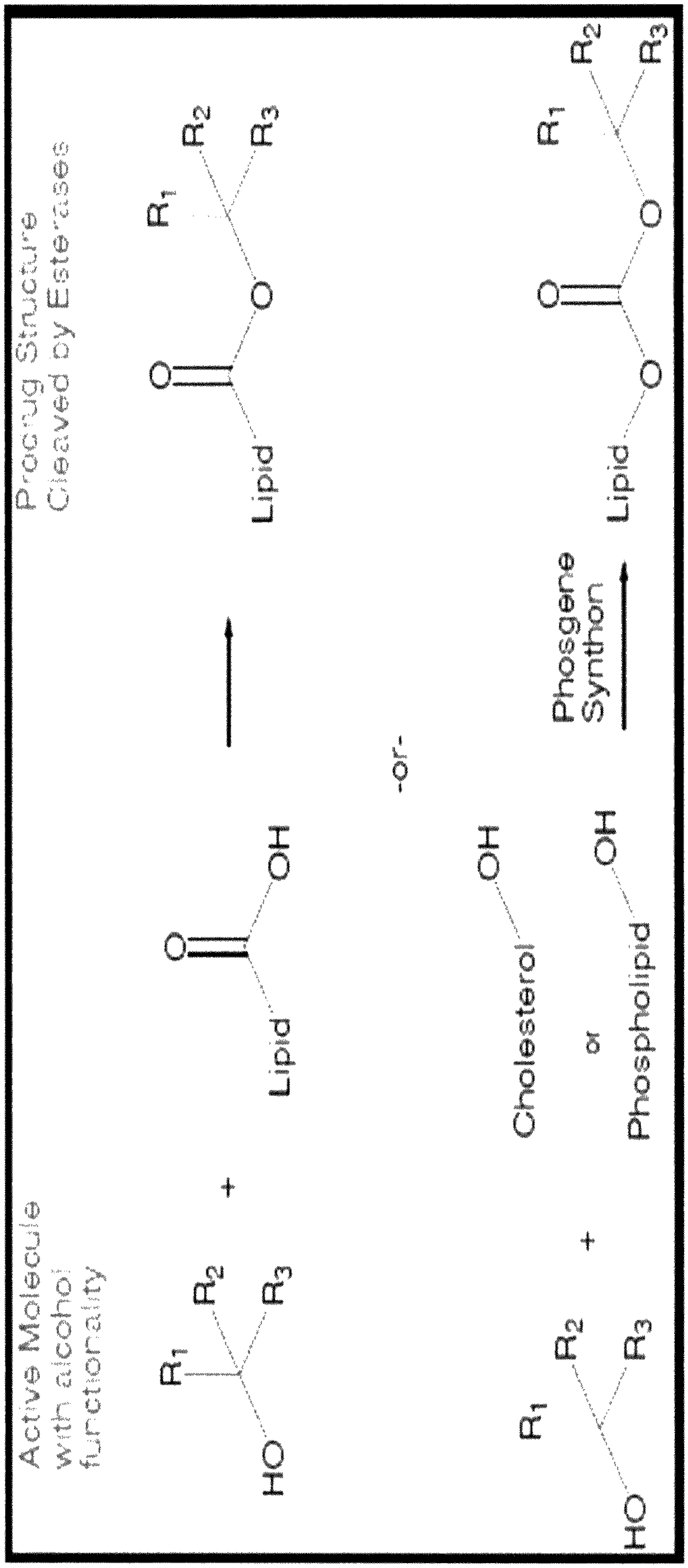

Figure 6. ALK5 Inhibitor Prodrug Synthesis Schema with Secondary Amine, Amide, or Aniline Functionality
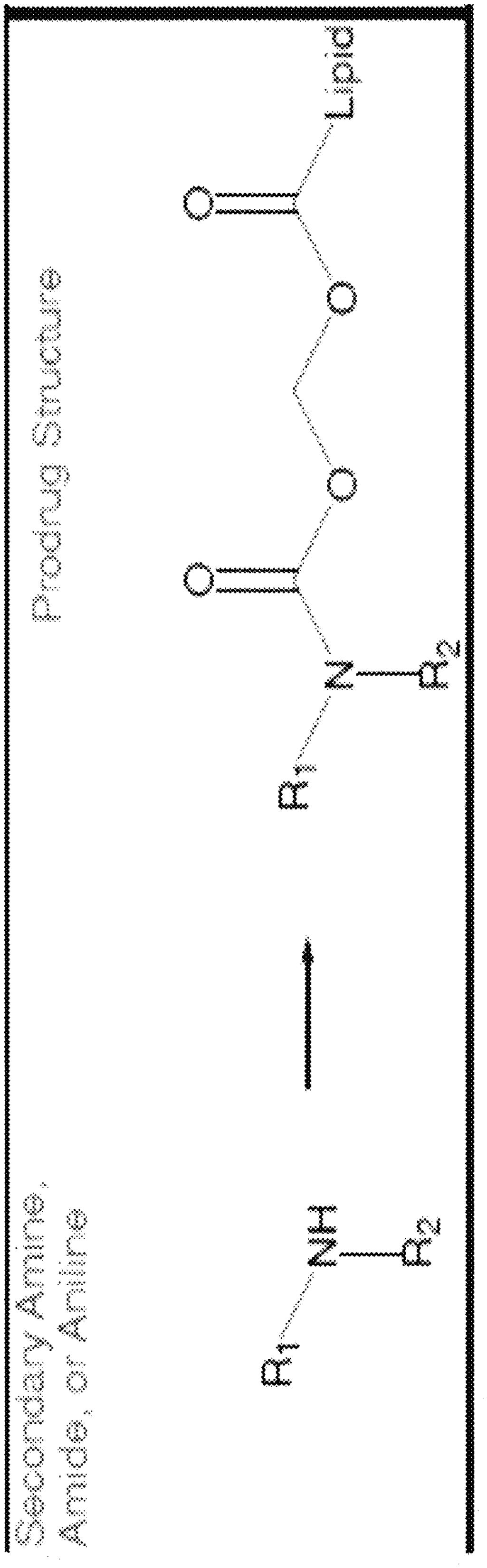

Figure 7. Chemical Synthesis for TB4-Prodrug Comprising Stearic Acid
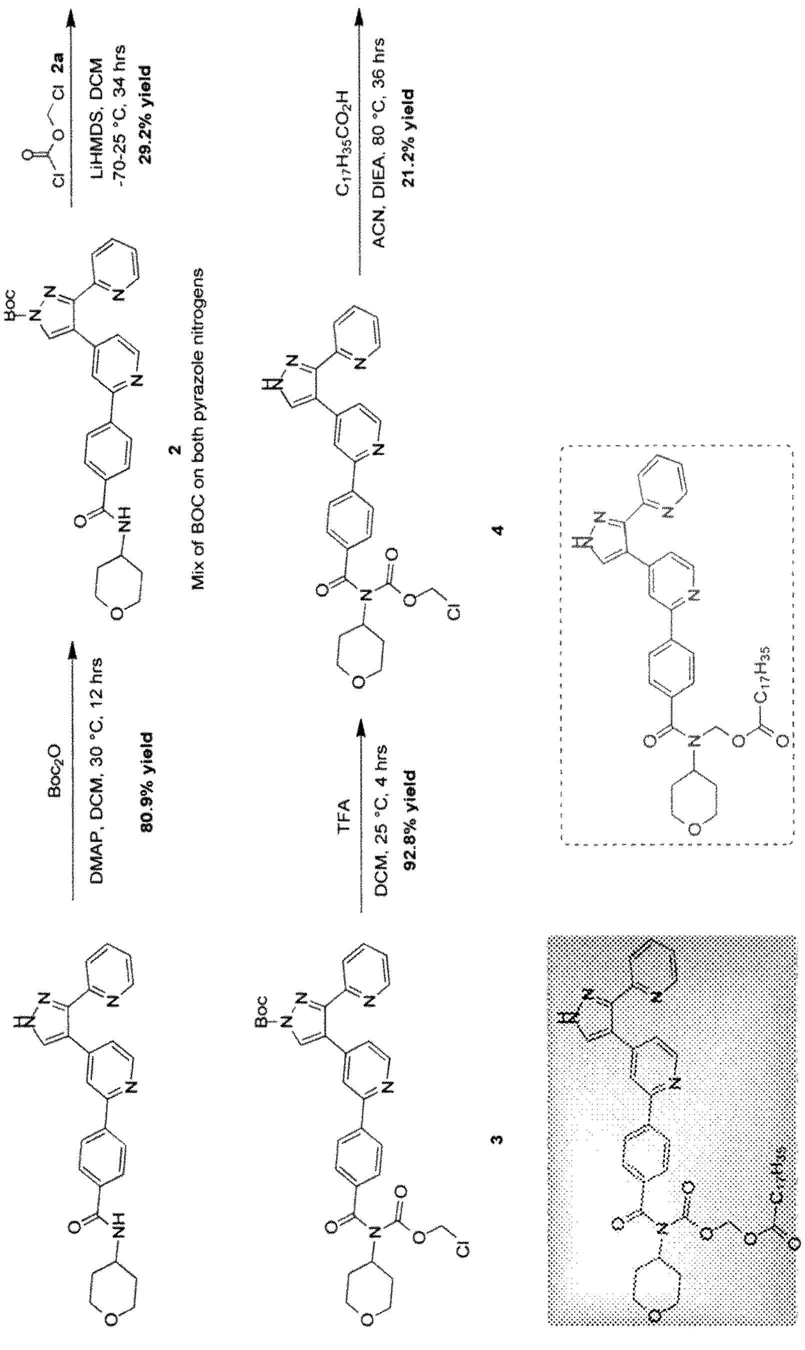
2
3
4

Figure 8. Characterization of LNP-TB4 Liposome
| | | | | | |
|---|---|---|---|---|---|
| | | | Size (d.nm): | % Intensity: | St Dev (d.nm): |
| Z-Average (d.nm): | 87.11 | Peak 1: | 120.5 | 100.0 | 68.17 |
| PdI: | 0.265 | Peak 2: | 0.000 | 0.0 | 0.000 |
| Intercept: | 0.947 | Peak 3: | 0.000 | 0.0 | 0.000 |
| Result quality : | Good | | | | |
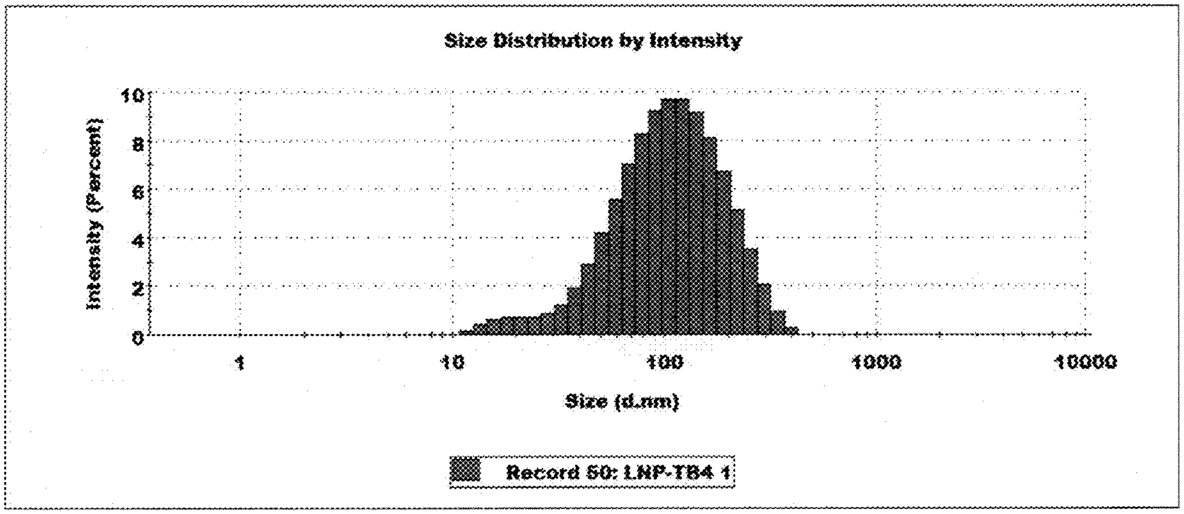

Figure 9. Characterization of LNP-TB4 Liposome (Zeta Potential)
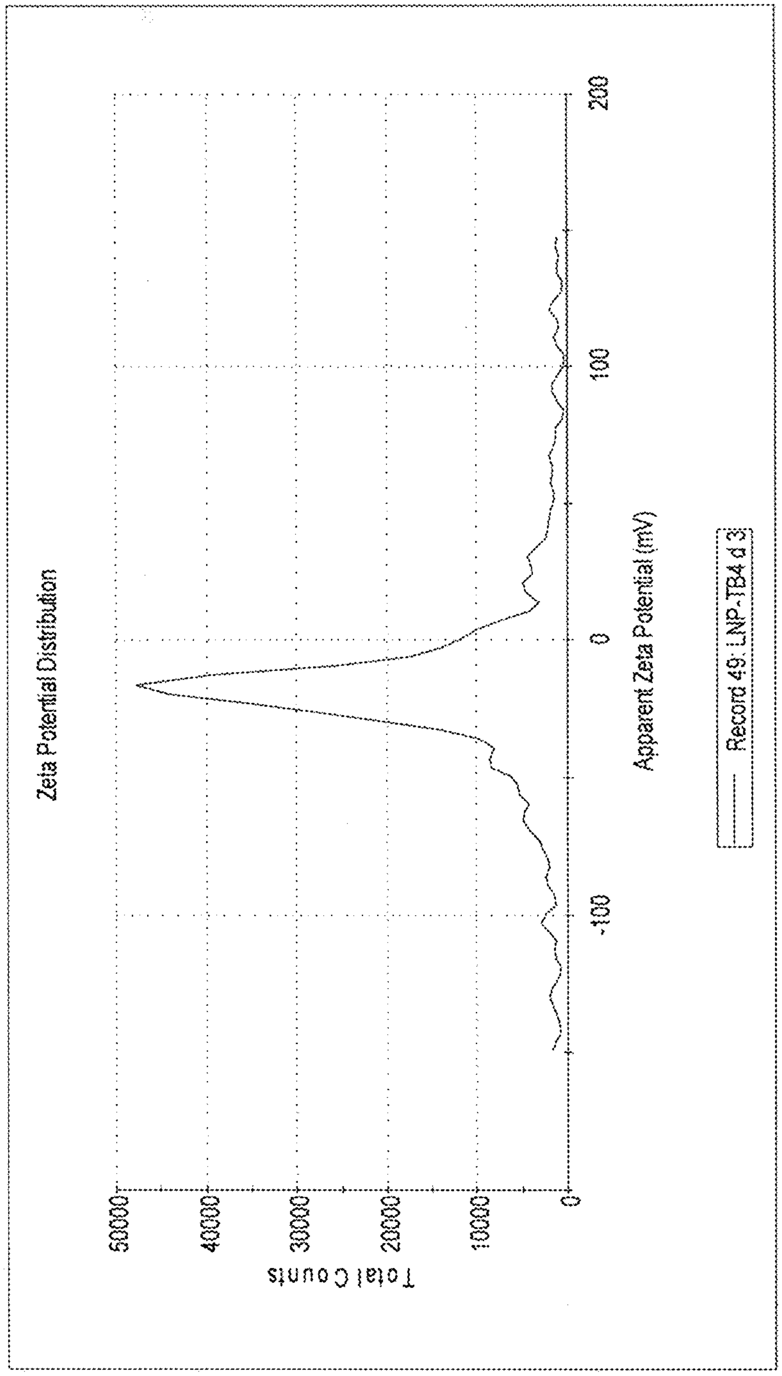

Figure 10. Characterization of LNP-TB4-ID3 Liposome
| | | | Size (d.nm): | % Intensity: | St Dev (d.nm): |
|---|---|---|---|---|---|
| Z-Average (d.nm): | 67.29 | Peak 1: | 95.30 | 100.0 | 30.72 |
| Pdi: | 0.075 | Peak 2: | 0.000 | 0.0 | 0.000 |
| Intercept: | 0.925 | Peak 3: | 0.000 | 0.0 | 0.000 |
| Result quality : | Good | | | | |
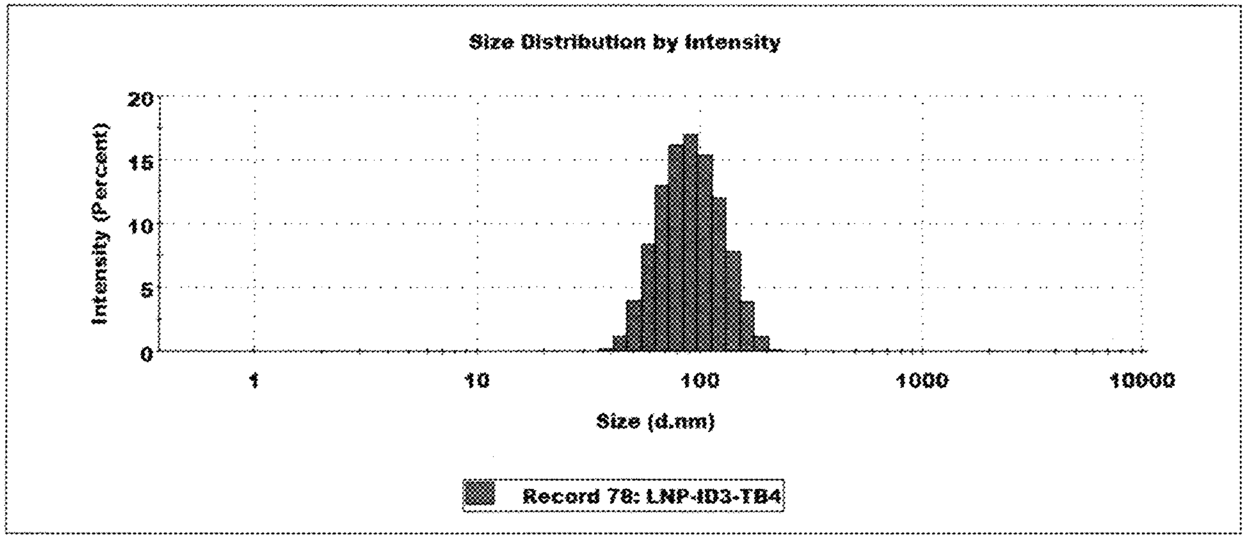

Figure 11. Characterization of LNP-TB4-iD3 Liposome (Zeta Potential)
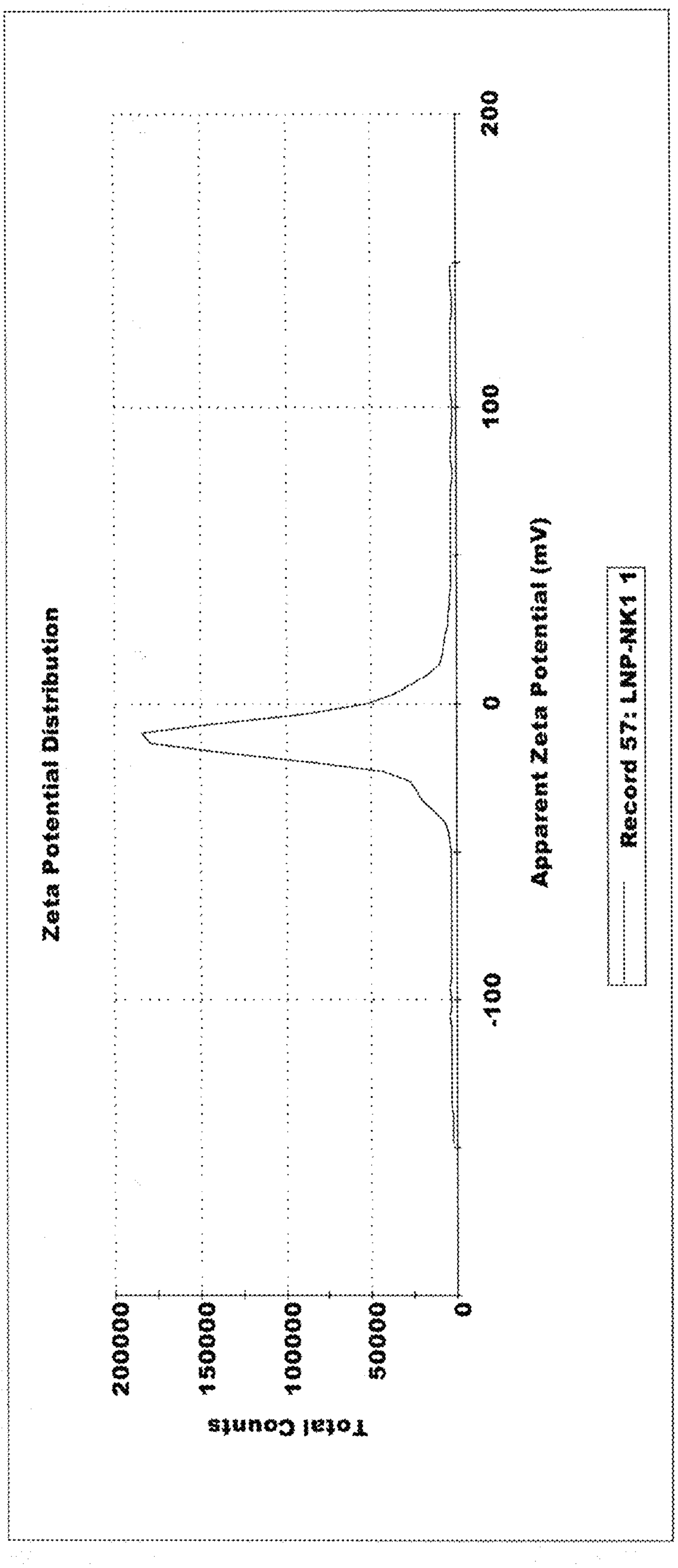

Figure 12. Characterization of SLNP-TB4 Solid-Lipid Nanoparticle
| | | | Size (d.nm): | % Intensity: | St Dev (d.nm): |
|---|---|---|---|---|---|
| Z-Average (d.nm): | 89.42 | Peak 1: | 97.61 | 100.0 | 29.95 |
| PdI: | 0.074 | Peak 2: | 0.000 | 0.0 | 0.000 |
| Intercept: | 0.923 | Peak 3: | 0.000 | 0.0 | 0.000 |
| Result quality : | Good | | | | |
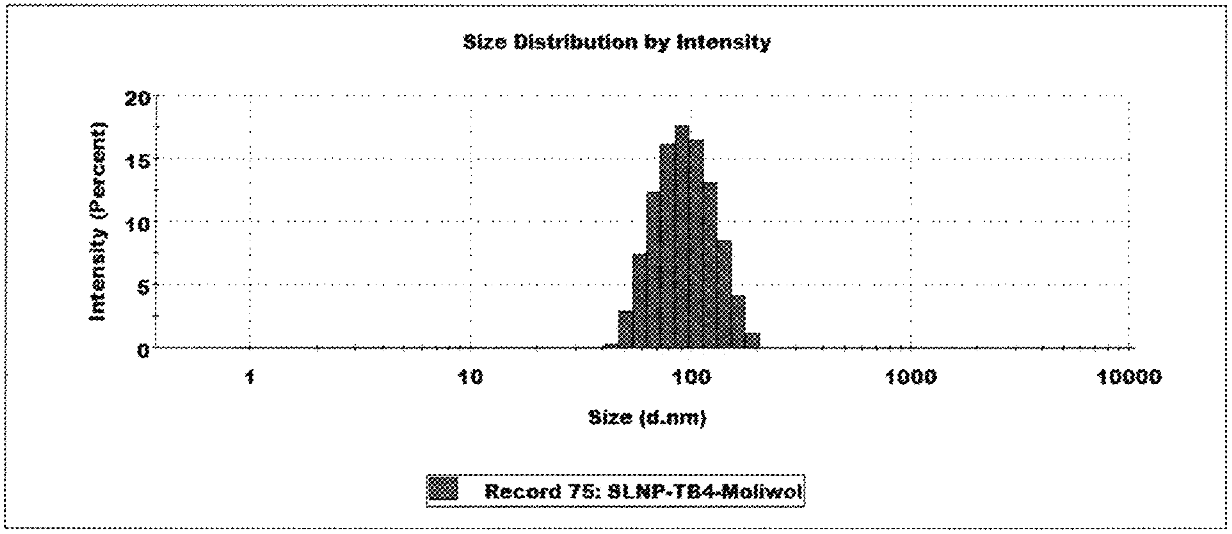

Figure 13. Characterization of SLNP-TB4 Solid-Lipid Nanoparticle (Zeta Potential)
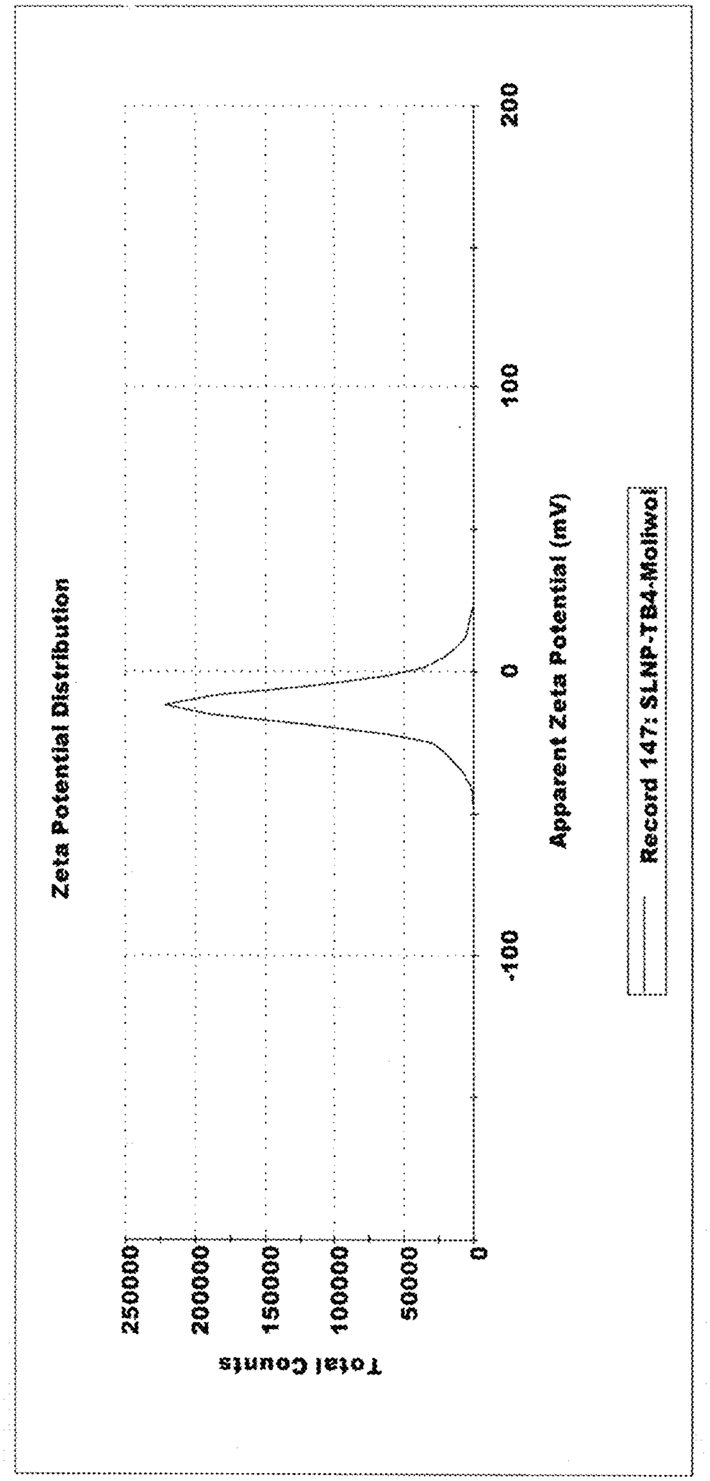

Figure 14. Characterization of SLNP-TB4-ID3 Solid-Lipid Nanoparticle
| | | | Size (d.nm): | % Intensity: | St Dev (d.nm): |
|---|---|---|---|---|---|
| Z-Average (d.nm): | 104.3 | Peak 1: | 118.4 | 100.0 | 48.92 |
| Pdl: | 0.119 | Peak 2: | 0.000 | 0.0 | 0.000 |
| Intercept: | 0.944 | Peak 3: | 0.000 | 0.0 | 0.000 |
| Result quality : | Good | | | | |
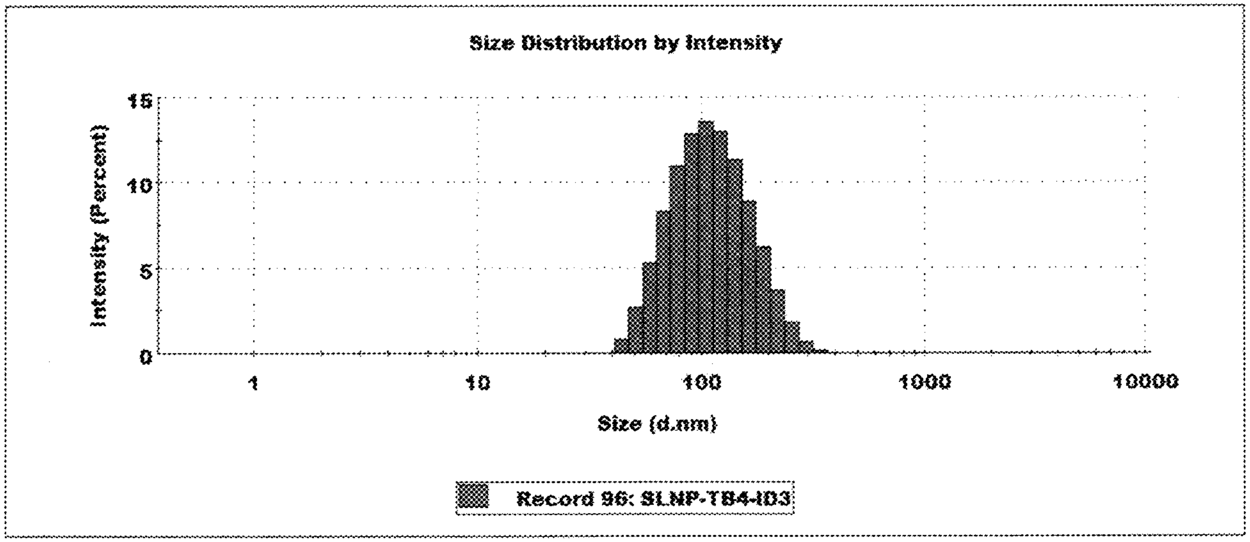

Figure 15. Characterization of SLNP-TB4-ID3 Solid-Lipid Nanoparticle (Zeta Potential)
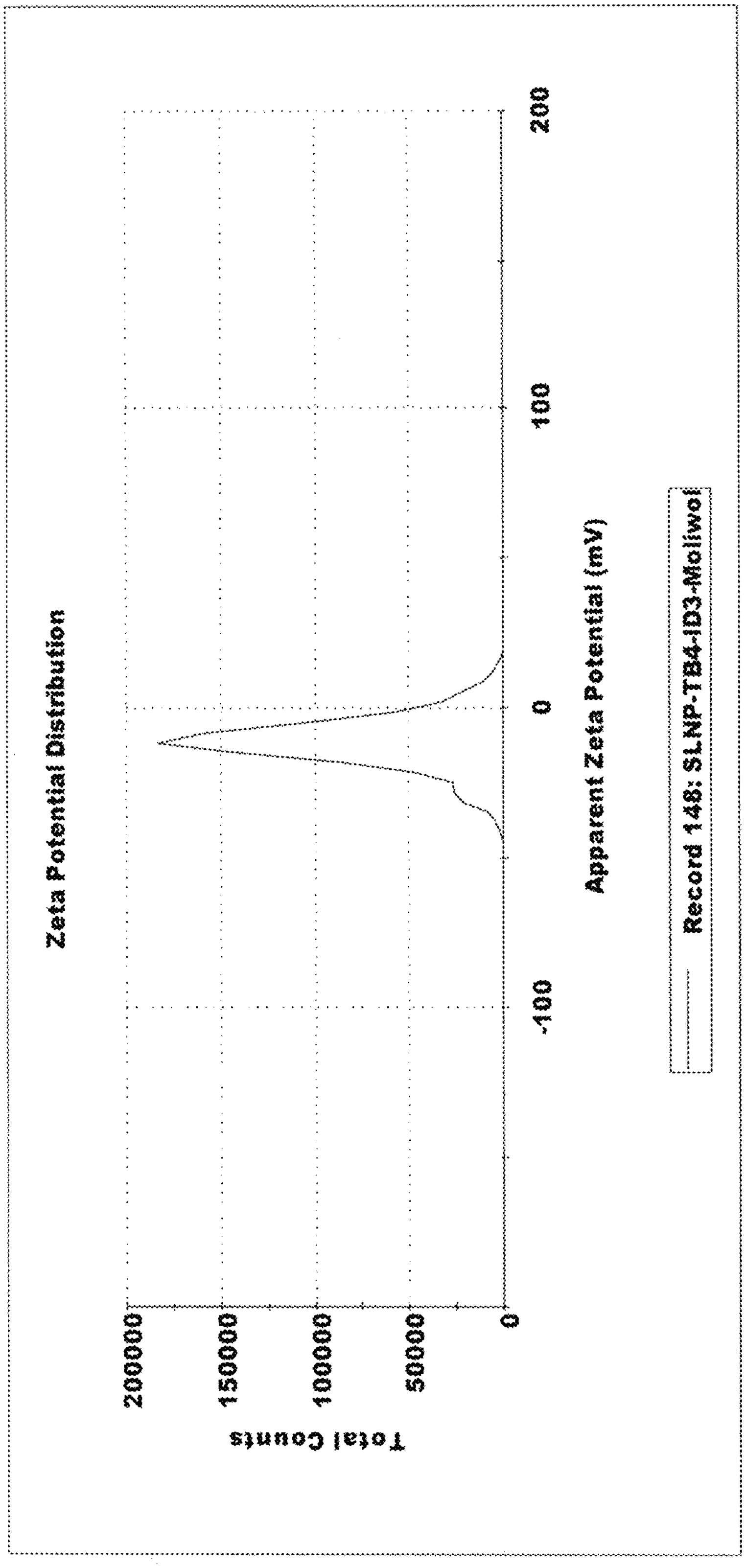

Figure 16. Tumor Inhibition of SLNP-TB4 In Combination With LNP-MTO Using B16F10 Cells *In Vivo*
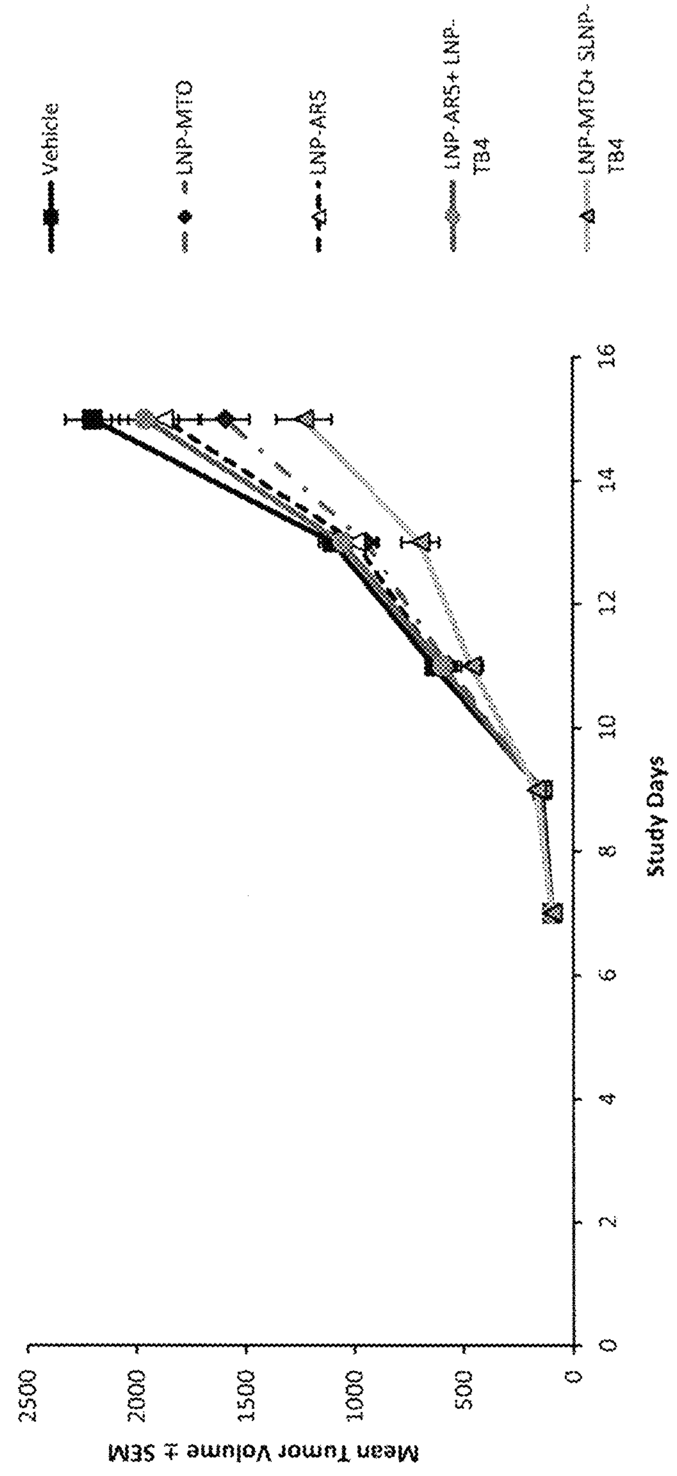

Figure 17. Tumor Inhibition of LNP-TB4 In Multiple Combination(s) Using B16F10 Cells *In Vivo*
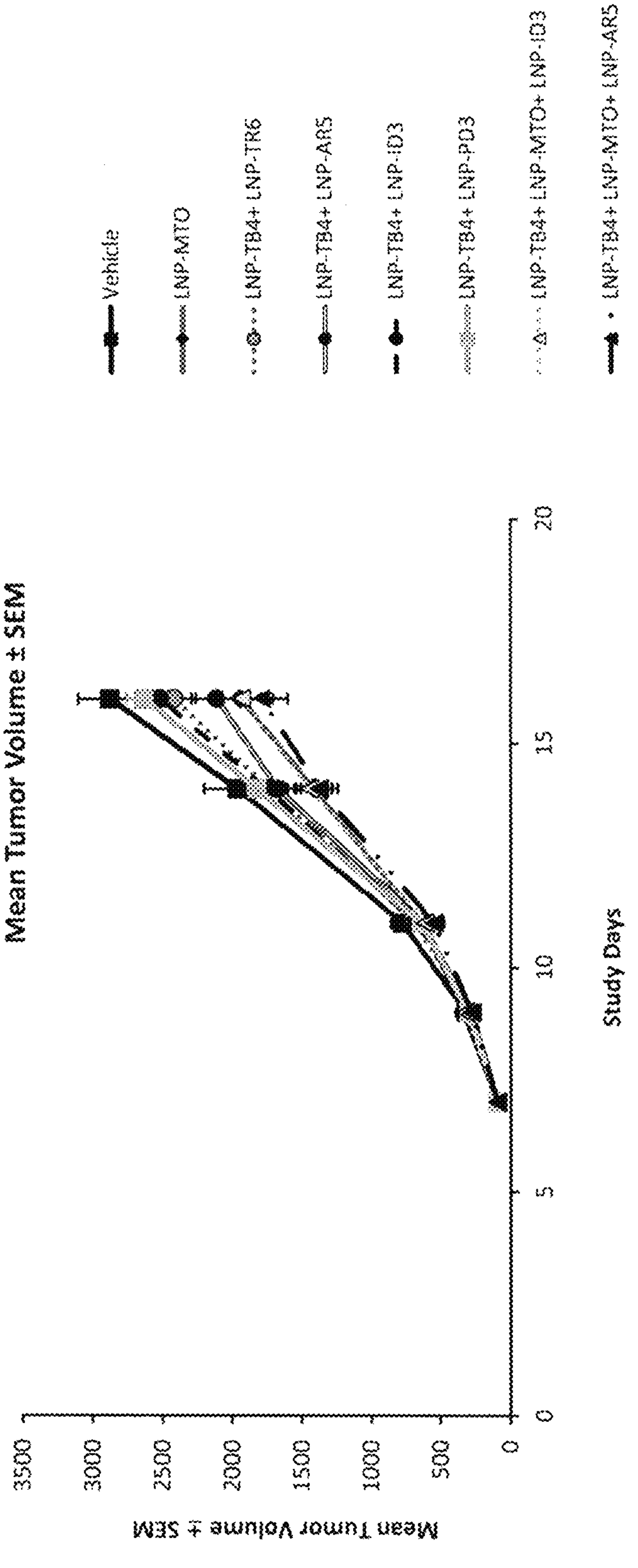

Figure 18. In *Vitro* Validation of LNP-TB4 and SLNP-TB4 Mechanism of Action.
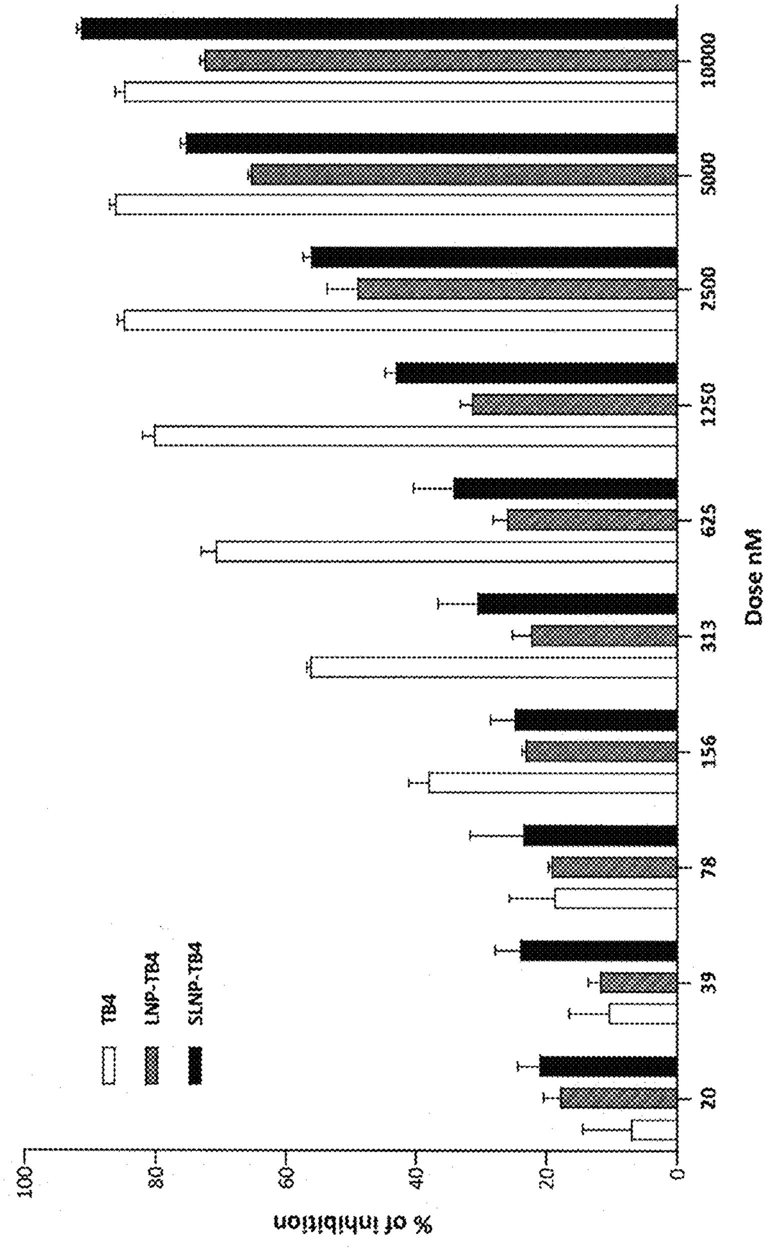

FORMULATED AND/OR CO-FORMULATED LIPOSOME COMPOSITIONS CONTAING TGFβ ANTAGONIST PRODRUGS USEFUL IN THE TREATMENT OF CANCER AND METHODS THEREOF

CROSS-REFERENCE TO RELATED APPLICATIONS

This application is a continuation of U.S. patent application Ser. No. 17/300,063, filed 19 Feb. 2021, which claims priority to U.S. Provisional Patent Application No. 62/995,887 filed 19 Feb. 2020; the contents of which are fully incorporated by reference herein.

STATEMENT OF RIGHTS TO INVENTIONS MADE UNDER FEDERALLY SPONSORED RESEARCH

Not applicable.

FIELD OF THE INVENTION

The invention described herein relates to prodrug compositions that inhibit signal transduction induced by transforming growth factor beta 1, 2, or 3 ("TGFβ") proteins after release of the active inhibitor from the prodrug and nanoformulations comprising such prodrugs. Specifically, the invention relates to prodrug compositions which are formulated within a nanocarrier (e.g., a liposome) and used as a vehicle for cancer therapy in humans. The invention also relates to co-formulations of such prodrugs with other immune-modulating agents or prodrugs. The invention further relates to the treatment of cancers and other immunological disorders and diseases.

BACKGROUND OF THE INVENTION

Cancer is the second leading cause of death next to coronary disease worldwide. Millions of people die from cancer every year and in the United States alone cancer kills well over a half-million people annually, with 1,688,780 new cancer cases diagnosed in 2017 (American Cancer Society). While deaths from heart disease have been declining significantly, those resulting from cancer generally are on the rise. In the early part of the next century, cancer is predicted to become the leading cause of death unless medical developments change the current trend.

Several cancers stand out as having high rates of mortality. In particular, carcinomas of the lung (18.4% of all cancer deaths), breast (6.6% of all cancer deaths), colorectal (9.2% of all cancer deaths), liver (8.2% of all cancer deaths), and stomach (8.2% of all cancer deaths) represent major causes of cancer death for both sexes in all ages worldwide (GLOBOCAN 2018). These and virtually all other carcinomas share a common lethal feature in that they metastasis to sites distant from the primary tumor and with very few exceptions, metastatic disease fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients also experience physical debilitations following treatment. Furthermore, many cancer patients experience a recurrence of their disease.

Although cancer therapy has improved over the past decades and survival rates have increased, the heterogeneity of cancer still demands new therapeutic strategies utilizing a plurality of treatment modalities. This is especially true in treating solid tumors at anatomical crucial sites (e.g., glioblastoma, squamous carcinoma of the head and neck and lung adenocarcinoma) which are sometimes limited to standard radiotherapy and/or chemotherapy. Nonetheless, detrimental effects of these therapies are chemo- and radio resistance, which promote loco-regional recurrences, distant metastases and second primary tumors, in addition to severe side-effects that reduce the patients' quality of life.

TGFβ refers to a subset of polypeptides of the transforming growth factor beta superfamily of cytokines. They are secreted proteins that perform many cellular functions, including the control of cell growth, cell proliferation, cell differentiation, and apoptosis. In humans, TGFβ1 is encoded by the TGFB1 gene. Functionally, TGFβ acts synergistically with TGF-α in inducing transformation. It also acts as a negative autocrine growth factor. Dysregulation of TGFβ activation and signaling may result in apoptosis. Many cells synthesize TGFβ and almost all cells have specific receptors for these cytokines. TGF-β1, TGF-β2, and TGF-β3 all function through the same receptor signaling systems. TGFβ plays an important role in controlling the immune system and shows different activities on different types of cell, or cells at different developmental stages. Most immune cells (or leukocytes) secrete TGFβ. See, LETTERIO, et. al., *Regulation of Immune Responses by TGF-beta*, Annu. Rev. Immunol. 16: pp 137-161 (1998). It has been taught that Some T cells (e.g., regulatory T cells) release TGFβ to inhibit the actions of other T cells. For example, Interleukin 1- and interleukin 2-dependent proliferation of activated T cells, and the activation of quiescent helper T cells and cytotoxic T cells is prevented by the activity of TGF-β1. See, GILBERT, et. al., *Transforming growth factor-beta 1 induces antigen-specific unresponsiveness in naïve T cells*, Immunol. Invest. 26(4): pp. 459-472 (1997) & WAHL, et. al., *TGF-beta: a mobile purveyor of immune privilege*, Immunol. Rev. 213: pp. 213-227 (2006). Similarly, TGFβ can inhibit the secretion and activity of many other cytokines including interferon-γ, tumor necrosis factor-alpha (TNF-α) and various interleukins. It can also decrease the expression levels of cytokine receptors, such as the IL-2 receptor to down-regulate the activity of immune cells. In addition, TGFβ has similar effects on B cells that also vary according to the differentiation state of the cell. It inhibits proliferation and stimulates apoptosis of B cells and plays a role in controlling the expression of antibody, transferrin, and MHC class II proteins on immature and mature B cells. LEBMAN, et. al., *The role of TGF-beta in growth differentiation, and maturation of b lymphocytes*, Microbes Infect., 1(15) pp 1297-1304 (1999). Finally, the effects of TGFβ on macrophages and monocytes is predominantly suppressive; this cytokine can inhibit the proliferation of these cells and prevent their production of reactive oxygen (e.g., superoxide ($O_2^-$)) and nitrogen (e.g., nitric oxide (NO)) intermediates. However, as with other cell types, TGFβ can also have the opposite effect on cells of myeloid origin. See, WAHL, et. al., supra. It has also been shown that TGFβ reduces the efficacy of the MHC II an astrocytes and dendritic cells, which in turn decreases the activation of appropriate helper T cell populations. See, TANG, et. al., *The Smad3 protein is involved in TGF-beta inhibition of class II transactivator and class II MHC expression*, J. of Immun, 167(1): pp. 311-319 (2001).

TGFβ elicits intracellular signals by first binding to the TGFβ Receptor II (TGFβRII), which then recruits a second receptor, TGFβ Receptor I (TGFβRI), also known as Activin-Like Kinase 5 (ALK5). Upon recruitment into the TGFβ receptor: ligand complex, TGWU phosphorylates and activates ALK5 which mediates downstream signaling leading to transcriptional regulation. It has been taught that ALK5 deletion or mutation in tumors appears to be the common form of pathway alteration. However, efforts directed at inhibiting the ALK5 cascade have shown promise. See, LOOMAS, et. al., *Activin receptor-like kinases: a diverse family playing an important role in cancer*, Am. J. Cancer Res. 6(11): pp. 2431-2447 (2016).

Currently, multiple small molecule kinase inhibitors have been identified that selectively inhibit ALK5 and have been developed to clinical stage testing as anti-cancer agents. Galunisertib (LY2157229) and Vactosertib (TEW-7197) are the most advanced therapeutic candidates in clinical trials and have demonstrated anti-cancer efficacy in humans as single agents and as combination therapies with approved drugs, validating this mechanism as a clinically meaningful approach. However, dosing is limited by cardiac toxicity induced by these molecules and combinations with other therapeutics risks increased systemic off-target toxicities.

A prodrug is a medication or compound that, after administration, is metabolized (i.e., converted within the body) into a pharmacologically active drug. Instead of administering a drug directly, a corresponding prodrug is used instead to improve how a medicine is absorbed, distributed, metabolized, and/or excreted. Prodrugs are often designed to improve bioavailability when a drug itself is poorly absorbed from the gastrointestinal tract, for example. A prodrug may be used to improve how selectively the drug interacts with cells or processes that are not its intended target. This reduces adverse or unintended effects of a drug, especially important in treatments like chemotherapy, which can have severe unintended and undesirable side effects. Prodrugs can thus be viewed as drugs containing specialized non-toxic protective groups used in a transient manner to alter or to eliminate undesirable properties in the parent molecule.

Finally, a nanocarrier is a nanomaterial being used as a transport for another substance, such as a drug. There are many different types of nanocarriers. For example, nanocarriers include polymer conjugates, polymeric nanoparticles, lipid-based carriers, and dendrimers to name a few. Different types of nanomaterial(s) being used in nanocarriers allows for hydrophobic and hydrophilic drugs to be delivered throughout the body. Since the human body contains mostly water, the ability to deliver hydrophobic drugs effectively in humans is a major therapeutic benefit of nanocarriers. Nanocarriers show promise in the drug delivery process because they can deliver drugs to site-specific targets, allowing drugs to be delivered in certain organs or cells but not in others. Site-specificity is a major therapeutic benefit since it prevents drugs from being delivered to the wrong places. Additionally, nanocarriers show specific promise for use in chemotherapy because they can help decrease the adverse, broader-scale toxicity of chemotherapy on healthy, fast growing cells around the body. Since chemotherapy drugs can be extremely toxic to human cells, it is important that they are delivered to the tumor without being released into other parts of the body.

From the aforementioned, it will be readily apparent to those skilled in the art that a new treatment paradigm is needed in the treatment of cancers and other immunological diseases. By using novel prodrugs in conjunction with modern nanocarrier modalities, a new disease treatment can be achieved with the overall goal of more effective treatment (s), reduced side effects, and greater therapeutic utility in the treatment of cancers, especially the treatment of cancers in solid tumors.

Given the current deficiencies associated with cancer treatment, it is an object of the present invention to provide new and improved methods of treating cancer(s), immunological disorders, and other diseases utilizing prodrugs encapsulated within a nanocarrier.

SUMMARY OF THE INVENTION

The invention provides for ALK5 inhibitor prodrug ("TB Prodrug") compositions comprising an ALK5 inhibitor agent, a lipid, and a biologically cleavable linker. In certain embodiments, nanocarriers comprising a TB Prodrug are formulated for use as a delivery modality to treat human diseases such as cancer, including solid tumor cancers as well as other immunological disorders. In certain embodiments, the nanocarriers comprise a lipid-bilayer capable of being incorporated into a drug delivery vehicle (i.e., a liposome). In a further preferred embodiment, the liposome comprises cholesterol hemisuccinate ("CHEMS"). In a further preferred embodiment, the liposome of the invention comprises Stearic Acid.

In a further embodiment, a TB Prodrug of the disclosure comprises a TB4-Prodrug.

In a further embodiment, the invention comprises methods of delivering an ALK5 inhibitor to a tumor comprising (i) synthesizing a TB Prodrug; (ii) formulating a TB Prodrug of the invention in a nanocarrier of the invention; and (iii) administering the nanocarrier to a patient.

In another embodiment, the invention comprises methods of delivering an ALK5 inhibitor with one or more additional immune modulating agent to a tumor comprising (i) synthesizing a TB Prodrug; (ii) co-formulating a TB Prodrug of the invention in a nanocarrier with one or more additional immune modulating agents of the invention; and (iii) administering the nanocarrier to a patient.

In another embodiment, the immune modulating agents comprise immunogenic-cell death inducing chemotherapeutics, PD-1 antagonists, toll receptor agonists, STING agonists, IDO inhibitors, CTLA4 inhibitors, CD1D agonists, and/or prodrugs thereof.

In another embodiment, the present disclosure teaches methods of synthesizing TB Prodrugs.

In another embodiment, the present disclosure teaches methods of synthesizing a TB4-Prodrug.

In another embodiment, the present disclosure teaches methods of formulating TB Prodrugs within nanocarriers, including but not limited to liposomes.

In another embodiment, the present disclosure teaches methods of formulating a TB4 Prodrug within nanocarriers, including but not limited to liposomes.

In another embodiment, the present disclosure teaches methods of treating cancer(s), immunological disorders and other diseases in humans using nanocarriers of the present disclosure.

BRIEF DESCRIPTION OF THE FIGURES

FIG. 1. Chemical Synthesis for TB4-Prodrug.

FIG. 2. Chemical Synthesis for protective group intermediates en route to final TB4-Prodrug.

FIG. 3. Chemical Synthesis for protective group intermediates en route to final TB4-Prodrug.

FIG. 4. ALK5 Inhibitor Prodrug Synthesis Schema with Carboxylic Acid Functionality.

FIG. 5. ALK5 Inhibitor Prodrug Synthesis Schema with Alcohol Functionality.

FIG. 6. ALK5 Inhibitor Prodrug Synthesis Schema with Secondary Amine, Amide, or Aniline Functionality.

FIG. 7. Chemical Synthesis for TB4-Prodrug Comprising Stearic Acid.

FIG. 8. Characterization of LNP-TB4 Liposome.

FIG. 9. Characterization of LNP-TB4 Liposome (Zeta Potential).

FIG. 10. Characterization of LNP-TB4-ID3 Liposome.

FIG. 11. Characterization of LNP-TB4-ID3 Liposome (Zeta Potential).

FIG. 12. Characterization of SLNP-TB4 Solid-Lipid Nanoparticle.

FIG. 13. Characterization of SLNP-TB4 Solid-Lipid Nanoparticle (Zeta Potential).

FIG. 14. Characterization of SLNP-TB4-ID3 Solid-Lipid Nanoparticle.

FIG. 15. Characterization of SLNP-TB4-ID3 Solid-Lipid Nanoparticle (Zeta Potential).

FIG. 16. Tumor Inhibition of SLNP-TB4 In Combination With LNP-MTO Using B16F10 Cells In Vivo.

FIG. 17. Tumor Inhibition of LNP-TB4 In Multiple Combination(s) Using B16F10 Cells In Vivo.

FIG. 18. In Vitro Validation of LNP-TB4 and SLNP-TB4 Mechanism of Action.

DETAILED DESCRIPTION OF THE INVENTION

Outline of Sections

- I.) Definitions
- II.) Prodrugs
- III.) Chemical Compounds
- IV.) Lipids
- V.) Linkage Unit(s) ("LU")
- VI.) Nanocarriers
- VII.) Liposomes
- VIII) Pharmaceutical Formulation
- IX.) Combination Therapy
- X.) Methods of Delivering Liposomes Comprising Prodrugs to a Cell
- XI.) Methods of Treating Cancer(s) and Other Immunological Disorder(s)
- XII.) KITS/Articles of Manufacture

I.) Definitions

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art.

When a trade name is used herein, reference to the trade name also refers to the product formulation, the generic drug, and the active pharmaceutical ingredient(s) of the trade name product, unless otherwise indicated by context.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub combinations of A, B, C, and D.

Numerical ranges recited herein by endpoints include all numbers and fractions subsumed within that range (e.g., 1 to 5 includes, but is not limited to, 1, 1.5, 2, 2.75, 3, 3.90, 4, and 5).

As used herein, the phrase "consisting essentially of" limits the scope of a claim to the specified materials or steps, plus those that do not materially affect the basic and novel characteristic(s) of the claimed subject matter.

The terms "advanced cancer", "locally advanced cancer", "advanced disease" and "locally advanced disease" mean cancers that have extended through the relevant tissue capsule and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease and these patients have substantially less favorable outcomes compared to patients having clinically localized (organ-confined) cancer.

As used herein the term "alkyl" can refer to $C_1$-$C_{20}$ inclusive, linear (i.e., "straight-chain"), branched, or cyclic, saturated, or at least partially and in some cases unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and alkenyl groups. "Branched" refers to an alkyl group in which a lower alkyl group, such as methyl, ethyl, or propyl, is attached to a linear alkyl chain. "Lower alkyl" refers to an alkyl group having 1 to about 8 carbon atoms (i.e., a $C_1$-$C_8$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_1$-$C_8$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered aromatic and heteroaromatic rings. The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc.) in the backbone of a ring structure. Nitrogen-containing heteroaryl moieties include, but are not limited to, pyridine, imidazole, benzimidazole, pyrazole, pyrazine, triazine, pyrimidine, and the like.

The terms "anticancer drug", "chemotherapeutic", and "anticancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). In some embodiments, the term "chemotherapeutic" as used herein refers to a non-PS molecule that is used to treat cancer and/or that has cytotoxic ability. More traditional or conventional chemotherapeutic agents can be described by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinca alkaloids (e.g., vinblastine).

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched, or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($—CH_2—$); ethylene ($—CH_2—CH_2—$); propylene ($—(CH_2)3-$); cyclohexylene ($—C_6H_{10}—$); —CH═CH—CH═CH—; $—CH═CH—CH_2—$; $—(CH2)_q—N(R)—(CH_2)—$, wherein each of q is an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($—O—CH_2—O—$); and ethylenedioxyl ($—O—(CH_2)_2—O—$). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "amino" refers to the group $—N(R)_2$ wherein each R is independently H, alkyl, substituted alkyl, aryl, substituted aryl, aralkyl, or substituted aralkyl. The terms "aminoalkyl" and "alkylamino" can refer to the group $—N(R)_2$ wherein each R is H, alkyl, or substituted alkyl, and wherein at least one R is alkyl or substituted alkyl. "Arylamine" and "aminoaryl" refer to the group $—N(R)_2$ wherein each R is H, aryl, or substituted aryl, and wherein at least one R is aryl or substituted aryl, e.g., aniline (i.e., $—NHC_6H_5$).

"Bulk" (a.k.a. Drug Substance) means the drug substance or the drug product which has not been filled into final containers for distribution. Final formulated bulk generally refers to drug product which is formulated and being stored or held prior to filling. Drug substance may be stored or held as "bulk" or "concentrated bulk" prior to formulation into drug product.

The terms "carboxylate" and "carboxylic acid" can refer to the groups —C(═O)O— and —C(═O)OH, respectively. The term "carboxyl" can also refer to the —C(═O)OH group.

The terms "conjugate" and "conjugated" as used herein can refer to the attachment (e.g., the covalent attachment) of two or more components (e.g., chemical compounds, polymers, biomolecule, particles, etc.) to one another. In some embodiments, a conjugate can comprise monovalent moieties derived from two different chemical compounds covalently linked via a bivalent linker moiety (e.g., an optionally substituted alkylene or arylene). In some embodiments, the linker can contain one or more biodegradable bond, such that one or more bonds in the linker can be broken when the prodrug is exposed to a particular physiological environment or enzyme (for example, esterases).

The term "compound" refers to and encompasses the chemical compound (e.g. a prodrug) itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above.

"Drug product" means a final formulation that contains an active drug ingredient (i.e., liposomes containing ALK5 inhibitor prodrugs) generally, but not necessarily, in association with inactive ingredients. The term also includes a finished dosage form that does not contain an active ingredient but is intended to be used as a placebo.

The term "disulfide" can refer to the —S—S— group.

The term "empty vesicle" means an unloaded lipid vesicle by itself.

The term "ester" as used herein means a chemical compound derived from acid (organic or inorganic) in which at least one —OH hydroxyl group is replaced by an —O-alkyl (alkoxy) or O-Aryl (aryloxy) group.

The term "esterase" as used herein is a hydrolase enzyme that splits esters into an acid and an alcohol.

"Excipient" means an inactive substance used as a carrier for the active ingredients in a drug such as vaccines. Excipients are also sometimes used to bulk up formulations with very potent active ingredients, to allow for convenient and accurate dosage. Examples of excipients include but are not limited to, anti-adherents, binders, coatings, disintegrants, fillers, diluents, flavors, colors, lubricants, and preservatives.

The terms "halo", "halide", or "halogen" as used herein refer to fluoro, chloro, bromo, and iodo groups.

The terms "hydroxyl" and "hydroxy" refer to the —OH group.

The terms "inhibit" or "inhibition of" as used herein means to reduce by a measurable amount, or to prevent entirely.

The terms "individual" or "patient," as used in the context of this disclosure can be used interchangeably.

As used herein, the term "ligand" refers generally to a species, such as a molecule or ion, which interacts, e.g., binds, in some way with another species. See Martell, A. E., and Hancock, R. P., Metal Complexes in Aqueous Solutions, Plenum: New York (1996), which is incorporated herein by reference in its entirety.

The term "lipid" as used herein refers to a class of naturally occurring (organic) compounds that are insoluble in polar solvents. In the context of the disclosure, a lipid refers to conventional lipids, phospholipids, cholesterol, chemically functionalized lipids for attachment of PEG and ligands, etc.

The term "lipid bilayer" or "LB" refers to any double layer of oriented amphipathic lipid molecules in which the hydrocarbon tails face inward to form a continuous non-polar phase.

The term(s) "liposome" or "lipid vesicle" or "vesicle" are used interchangeably to refer to an aqueous compartment enclosed by a lipid bilayer, as being conventionally defined (see, Stryer (1981) Biochemistry, 2d Edition, W. H. Freeman & Co., p. 213).

The term "mammal" refers to any organism classified as a mammal, including mice, rats, rabbits, dogs, cats, cows, horses, and humans. In one embodiment of the invention, the mammal is a mouse. In another embodiment of the invention, the mammal is a human.

The terms "mercapto" or "thiol" refer to the —SH group.

The terms "metastatic cancer" and "metastatic disease" mean cancers that have spread to regional lymph nodes or to distant sites and are meant to include stage D disease under the AUA system and stage T×N×M+ under the TNM system.

The terms "nanocarrier", "nanoparticle, and "nanoparticle drug carrier" are used interchangeably and refer to a nanostructure having an aqueous, solid, or polymeric interior core. In certain embodiments the nanocarrier comprises a lipid bilayer encasing (or surrounding or enveloping) the porous particle core. In certain embodiments the nanocarrier is a liposome, lipid nanoparticle ("LNP") or a solid-lipid nanoparticle ("SLNP").

The terms "nanoscale particle," "nanomaterial," "nanocarrier", and "nanoparticle" refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is between about 20 nm and about 250 nm (e.g., about 20, 30, 40, 50, 60, 70, 80, 90, 100, 110, 120, 130, 140, 150, 160, 170, 180, 190, 200, 210, 220, 230, 240, or 250 nm).

The term "nanovesicle" refers to a "lipid vesicle" having a diameter (or population of vesicles having a mean diameter) ranging from about 20 nm, or from about 30 nm, or from about 40 nm, or from about 50 nm up to about 500 nm, or up to about 400 nm, or up to about 300 nm, or up to about 200 nm, or up to about 150 nm, or up to about 100 nm, or up to about 80 nm. In certain embodiments a nanovesicle has a diameter ranging from about 40 nm up to about 80 nm, or from about 50 nm up to about 70 nm.

"Pharmaceutically acceptable" refers to a non-toxic, inert, and/or composition that is physiologically compatible with humans or other mammals.

"Pharmaceutical formulation" means the process in which different chemical substances are combined to a pure drug substance to produce a final drug product.

The term "phosphonate" refers to the $—P(=O)(OR)_2$ group, wherein each R can be independently H, alkyl, aralkyl, aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "phosphate" refers to the $—OP(=O)(OR')_2$ group, where R' is H or a negative charge.

The term "prodrug" means a medication or compound that, after administration, is metabolized into a pharmacologically active drug. For the purposes of this disclosure, a prodrug of the invention comprises three (3) components: (i) a drug moiety; (ii) a lipid moiety; and (iii) a linkage unit ("LU").

The term "TB Prodrug" means a prodrug of the inventions wherein the drug moiety comprises an ALK5 inhibitor.

The term "pyrolipid" refers to a conjugate of a lipid and a porphyrin, porphyrin derivative, or porphyrin analog. In some embodiments, the pyrolipid can comprise a lipid conjugate wherein a porphyrin or a derivative or analog thereof is covalently attached to a lipid side chain. See, for example U.S. Patent Application Publication No. 2014/0127763.

As used herein, the terms "specific", "specifically binds" and "binds specifically" refer to the selective binding of nanocarrier of the invention to the target TGFβ1 or related family member.

The term "supported lipid bilayer" means a lipid bilayer enclosing a porous particle core. This definition as set forth in the disclosure is denoted because the lipid bilayer is located on the surface and supported by a porous particle core. In certain embodiments, the lipid bilayer can have a thickness ranging from about 6 nm to about 7 nm which includes a 3-4 nm thickness of the hydrophobic core, plus the hydrated hydrophilic head group layers (each about 0.9 nm) plus two partially hydrated regions of about 0.3 nm each. In various embodiments, the lipid bilayer surrounding the liposome comprises a continuous bilayer or substantially continuous bilayer that effectively envelops and seals the ALK5 inhibitor.

The term "thioalkyl" can refer to the group —SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

The term "therapeutically effective amount" refers to the amount of active prodrug, nano-encapsulated prodrug, or pharmaceutical agent that elicits the biological or medicinal response in a tissue, system, animal, individual or human.

The term "unsupported lipid bilayer" means an uncoated lipid bilayer in a lipid vesicle or liposome.

II.) Prodrugs

As shown in the present disclosure and for the purposes of this invention, a suitable prodrug is formed by conjugating a drug moiety of the invention (See, section entitled Drug Moieties) to a lipid moiety of the invention (See, section entitled Lipids) via an LU (See, section entitled Linkage Units) of the present disclosure. For the purposes of this disclosure, formation of a TB Prodrug can utilize several strategies. (See, for example, FIG. 4, FIG. 5, and FIG. 6).

Accordingly, in some embodiments, the prodrug is a drug-lipid moiety comprising an ALK5 inhibitor of the disclosure.

In one embodiment, the prodrug comprises the following chemical structure denoted Formula I:

FORMULA I

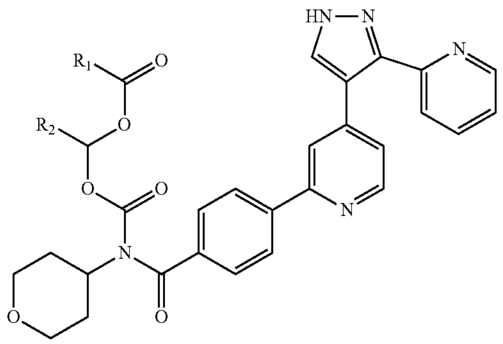

Wherein, in exemplary embodiments of FORMULA I:

$R_1$=$C_{11}$-$C_{21}$ saturated alkyl; and $R_2$=H, $CH_3$;

In a further embodiment, the prodrug comprises the following chemical structure denoted Formula II:

FORMULA II

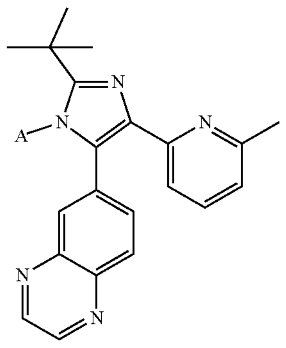

or

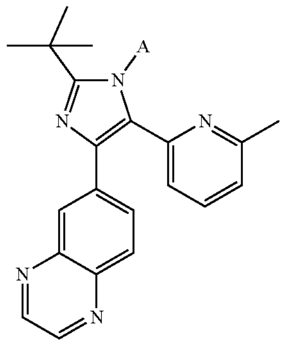

Wherein, in exemplary embodiments of FORMULA II:
A=

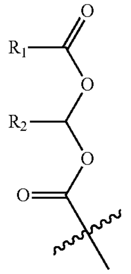

$R_1$=$C_{11}$-$C_{21}$ saturated alkyl; and
$R_2$=H, $CH_3$;

In a further embodiment, the prodrug comprises the following chemical structure denoted Formula III:

FORMULA III

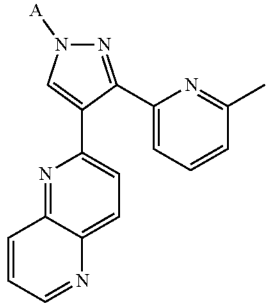

or

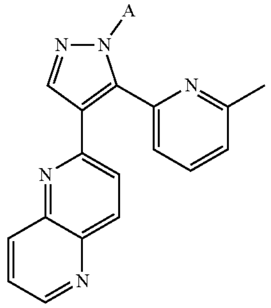

Wherein, in exemplary embodiments of FORMULA III:
A=

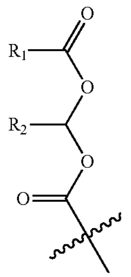

$R_1$=$C_{11}$-$C_{21}$ saturated alkyl; and
$R_2$=H, $CH_3$;

Thus, in one embodiment, the prodrug is a drug-lipid moiety comprising an ALK5 inhibitor of FORMULA I.

In a further embodiment, the prodrug is a drug-lipid moiety comprising an ALK5 inhibitor of FORMULA II.

In a further embodiment, the prodrug is a drug-lipid moiety comprising an ALK5 inhibitor of FORMULA III.

In one embodiment, the prodrug is a drug-lipid moiety comprising an ALK5 inhibitor set forth in FIG. 4.

In one embodiment, the prodrug is a drug-lipid moiety comprising an ALK5 inhibitor set forth in FIG. 5.

In one embodiment, the prodrug is a drug-lipid moiety comprising an ALK5 inhibitor set forth in FIG. 6.

In a further embodiment, the TB Prodrug is a drug-lipid moiety comprising a lipid of the disclosure.

In a further embodiment, the TB Prodrug is a drug-lipid moiety whereby the lipid is CHEMS.

In a further embodiment, the TB Prodrug is a drug-lipid moiety whereby the lipid is Stearic Acid.

In a further embodiment, the TB Prodrug is a drug-lipid moiety comprising a LU of the disclosure.

In a further embodiment, the TB Prodrug is a drug-lipid moiety whereby the LU is a hydromethylcarbamate linker.

In a further embodiment, the prodrug is a drug-lipid moiety comprising an ALK5 inhibitor of the invention, wherein the ALK5 inhibitor comprises the chemical composition(s) denoted TB4.

In a further embodiment, the prodrug is a drug-lipid moiety comprising an ALK5 inhibitor of the invention, wherein the ALK5 inhibitor comprises TB4 and has the following chemical structure:

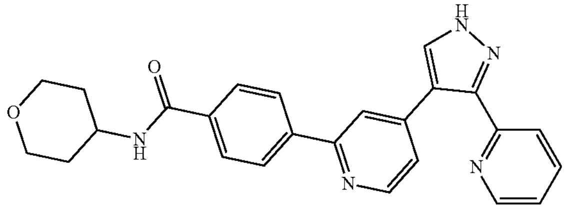 [SMILES: O=C(NC1CCOCC1)c1ccc(-c2cc(-c3c[nH]nc3-c3ccccn3)ccn2)cc1]

In a further embodiment, the prodrug is a drug-lipid moiety comprising an ALK5 inhibitor of the invention, wherein the ALK5 inhibitor comprises TB4 and further comprises a lipid of the disclosure having the following chemical formula:

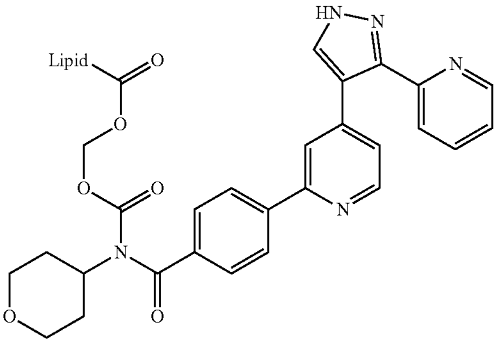

("TB4-Prodrug")

In a further embodiment, the prodrug is a drug-lipid moiety comprising an ALK5 inhibitor of the invention, wherein the ALK5 inhibitor comprises TB4 and further comprises CHEMS.

In a further embodiment, the prodrug is a drug-lipid moiety comprising an ALK5 inhibitor of the invention, wherein the ALK5 inhibitor comprises TB4 and further comprises Stearic Acid.

In a further embodiment, the prodrug is a drug-lipid moiety comprising an ALK5 inhibitor of the invention, wherein the ALK5 inhibitor comprises TB4 and further comprises CHEMS and whereby the LU is a hydromethylcarbamate linker.

In a further embodiment, the prodrug is a drug-lipid moiety comprising an ALK5 inhibitor of the invention, wherein the ALK5 inhibitor comprises TB4 and further comprises Stearic Acid and whereby the LU is a hydromethylcarbamate linker.

In a further embodiment, the prodrug is a drug-lipid moiety comprising an ALK5 inhibitor of the invention, wherein the ALK5 inhibitor comprises TB4 and further comprises Stearic Acid having the following structure:

tively. For instance, the monovalent derivative can be a deprotonated derivative of a chemical compound or lipid that comprises a hydroxyl, thiol, amino, or carboxylic acid group.

In further embodiments of the disclosure the subject matter provides an ALK5 inhibitor prodrug comprising a lipid-conjugated therapeutic agent parent drug. In some embodiments, the prodrug comprises: (a) a bivalent drug moiety, (b) a bivalent lipid moiety, and (c) a bivalent linker moiety comprising a linkage that will degrade in vivo, wherein the bivalent drug moiety and the bivalent lipid moiety are linked (e.g., covalently linked) through the linker. The bivalent drug moiety and the bivalent lipid moieties can be bivalent derivatives of a chemical compound and a lipid, respectively. For instance, the bivalent derivative can be a deprotonated derivative of a chemical compound or lipid that comprises a hydroxyl, thiol, amino, or carboxylic acid group.

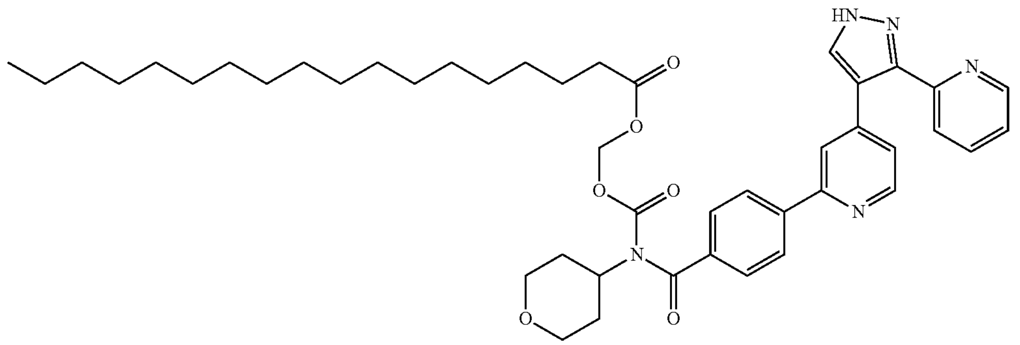 [SMILES: CCCCCCCCCCCCCCCCCC(=O)OCOC(=O)N(C(=O)c1ccc(-c2cc(-c3c[nH]nc3-c3ccccn3)ccn2)cc1)C1CCOCC1]

In a further embodiment, the prodrug is a drug-lipid moiety comprising an ALK5 inhibitor of the invention, wherein the ALK5 inhibitor comprises TB4 and further comprises Stearic Acid having the following structure:

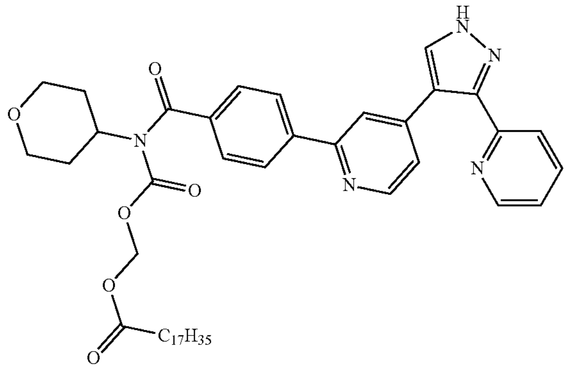

In additional embodiments of the disclosure the subject matter provides an ALK5 inhibitor prodrug comprising a lipid-conjugated therapeutic agent parent drug. In some embodiments, the prodrug comprises: (a) a monovalent drug moiety, (b) a monovalent lipid moiety, and (c) a bivalent linker moiety comprising a linkage unit that will degrade in vivo, such as a disulfide bond, wherein the monovalent drug moiety and the monovalent lipid moiety are linked (e.g., covalently linked) through the linker. The monovalent drug moiety and the monovalent lipid moieties can be monovalent derivatives of a chemical compound and a lipid, respectively.

One of ordinary skill in the art will appreciate and be enabled to make variations and modifications to the disclosed embodiment without altering the function and purpose of the invention disclosed herein. Such variations and modifications are intended within the scope of the present disclosure.

III.) Drug Moieties

Another aspect of the invention provides for novel TB Prodrug compound(s) comprising an ALK5 inhibitor with the following formula(s) denoted TB4.

One of skill in the art will appreciate that a compound is useful as an ALK5 signaling inhibitor (e.g., inhibits ALK5 and other family members). By way of brief background, ALK5 also known as TGFβ Receptor I (TGFβRI) is a membrane bound receptor which belongs to a superfamily of cytokines that act on protein kinase receptors at the plasma membrane to induce a plethora of biological signals that regulate cell growth and death, differentiation, immune response, angiogenesis, and inflammation. Dysregulation of its pathway contributes to a broad variety of pathologies, including cancer. TGFβ is an important regulatory tumor suppressor factor in epithelial cells, where it inhibits early proliferation and induces apoptosis. See, FABREGAT, et. al., *TGF-beta Signaling in Cancer Treatment*, Curr. Pharm. Des. 20(17): pp. 2934-2947 (2014). Research has shown that the development of therapeutic compounds that target TGFβ production or block its action may be useful in the treatment of cancer. See, HAQUE, et. al., *Transforming growth factor-β: A Therapeutic Target for Cancer*, Hum. Vaccin. Immunother., 13(8): pp. 1741-1750 (2017).

Based on the foregoing, the present disclosure describes a class of TGFβ inhibitors.

In one embodiment, a drug moiety of the disclosure comprises a compound with the following chemical structure (denoted TB4):

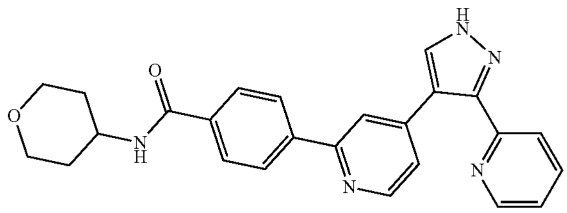

TB4

In one embodiment, a drug moiety of the disclosure comprises a protective group intermediate en route to the final TB4-Prodrug as set forth in FIG. 2.

In a further embodiment, a drug moiety of the disclosure comprises a protective group intermediate en route to the final TB4-Prodrug as set forth in FIG. 3.

One of ordinary skill in the art will appreciate and be enabled to make variations and modifications to the disclosed embodiment without altering the function and purpose of the invention disclosed herein. Such variations and modifications are intended within the scope of the present disclosure.

IV.) Lipids

Generally speaking, and for the purposes of this disclosure, the term "lipid" is used in its broadest sense and comprises several sub-categories of lipids, including but not limited to, phospholipids/fatty acids. As it is appreciated by one of skill in the art, a phospholipid represents a class of lipids that are a major component of all cell membranes. Phospholipids can form lipid bilayers because of their amphiphilic characteristic. The structure of the phospholipid molecule generally consists of two hydrophobic fatty acid "tails" and a hydrophilic "head" consisting of a phosphate group that can be modified with simple organic molecules such as choline, ethanolamine, or serine. These two components are usually joined together by a glycerol molecule. A representative list of phospholipids/fatty acid(s) of the invention are set forth in Table III.

By way of brief background, at the most fundamental level, the properties of a liposome depend upon the subtle physicochemical interactions among the various lipid species in its composition. Individual lipids can be combined to form a myriad of superstructures including bilayers, and bilayer properties can be tuned to modulate drug release and membrane stability. In a simplified bilayer model acyl chain length dictates bilayer thickness and phase transition temperature (Tm), acyl chain saturation controls bilayer fluidity, and headgroup interactions impact inter- and intra-lipid molecular forces. Liposome behavior can be adjusted by incorporating synthetic lipids such as lipid prodrugs, fusogenic lipids and functionalizable lipids into the bilayer. See, KOHLI, et. al., J. Control Release, 0: pp. 274-287 (Sep. 28, 2014).

In one embodiment of the present disclosure, a TB Prodrug comprises a monovalent lipid moiety.

In one embodiment, a TB Prodrug comprises a bivalent lipid moiety.

In one embodiment, the lipid comprises a cholesterol with the following chemical structure:

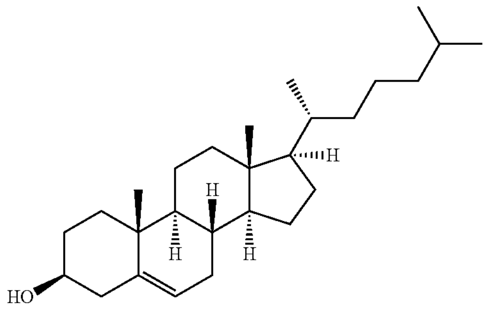

In one embodiment, the lipid comprises a DPPG with the following chemical structure:

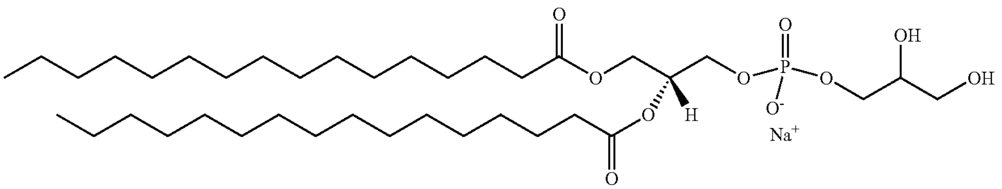 [SMILES: CCCCCCCCCCCCCCCC(=O)OC[C@H](COP(=O)([O-])OCC(O)CO)OC(=O)CCCCCCCCCCCCCCC ; [Na+]]

In one embodiment, the lipid comprises a DMPG with the following chemical structure:

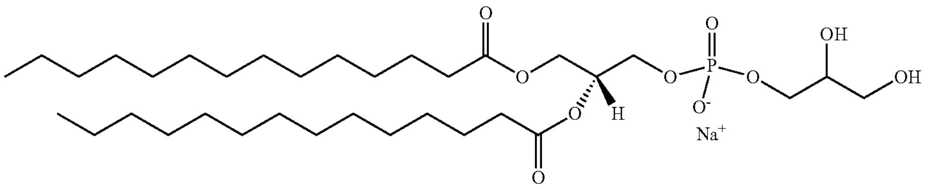 [SMILES: CCCCCCCCCCCCCC(=O)OC[C@H](COP(=O)([O-])OCC(O)CO)OC(=O)CCCCCCCCCCCCC ; [Na+]]

In one embodiment, the lipid comprises a Lyso PC with the following chemical structure:

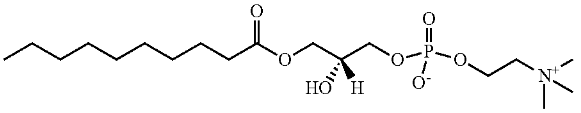 [SMILES: CCCCCCCCCC(=O)OC[C@@H](O)COP(=O)([O-])OCC[N+](C)(C)C]

In one embodiment, the lipid comprises a (Δ9-Cis) PG with the following chemical structure:

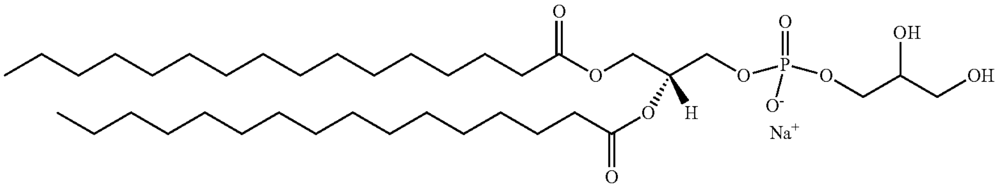 [SMILES: CCCCCCCCCCCCCCCC(=O)OC[C@H](COP(=O)([O-])OCC(O)CO)OC(=O)CCCCCCCCCCCCCCC ; [Na+]]

In one embodiment, the lipid comprises a Soy Lyso PC with the following chemical structure:

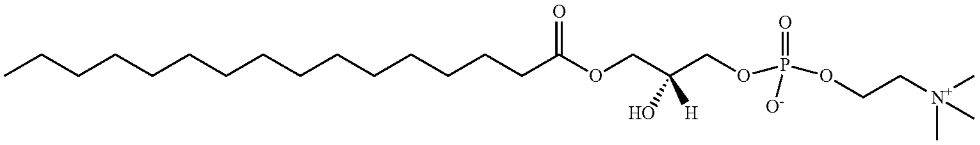 [SMILES: CCCCCCCCCCCCCCCC(=O)OC[C@@H](O)COP(=O)([O-])OCC[N+](C)(C)C]

In one embodiment, the lipid comprises a PG with the following chemical structure:

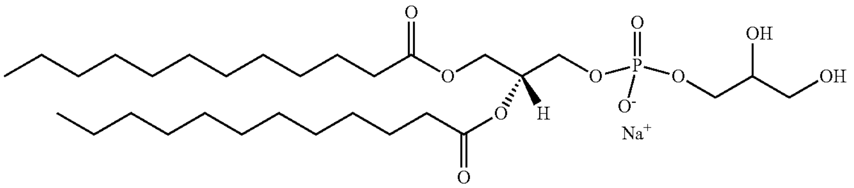 [SMILES: CCCCCCCCCCCC(=O)OC[C@H](COP(=O)([O-])OCC(O)CO)OC(=O)CCCCCCCCCCC ; [Na+]]

In one embodiment, the lipid comprises a C16 PEG2000 Ceramide with the following chemical structure:

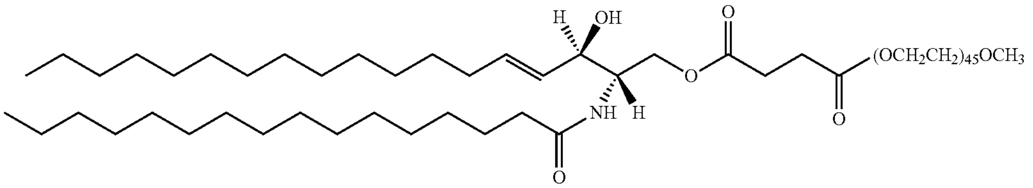

In one embodiment, the lipid comprises a cholesterol hemisuccinate ("CHEMS") with the following chemical structure:

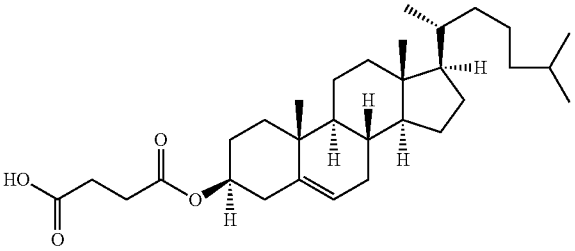

By way of reference, a complete list of the chemical formulas and abbreviation(s) of the lipids disclosed herein is set forth in Table I.

In an additional embodiment, the lipid comprises a phospholipid/fatty acid disclosed herein and set forth in Table III.

In a further embodiment, the lipid comprises a Stearic acid.

In addition, the TB Prodrugs and/or liposome(s) of the disclosure may comprise one or more helper lipids which are also referred to herein as "helper lipid components". The helper lipid components are preferably selected from the group comprising phospholipids and steroids. Phospholipids are preferably di- and monoester of the phosphoric acid. Preferred members of the phospholipids are phosphoglycerides and sphingolipids. Steroids, as used herein, are naturally occurring and synthetic compounds based on the partially hydrogenated cyclopenta[a]phenanthrene. Preferably, the steroids contain 21 to 30 C atoms. A particularly preferred steroid is cholesterol.

It is to be noted that although not wishing to be bound by any theory, due to the particular mol percentages of the helper lipid(s) contained in the lipid compositions according to the present invention, which helper lipid can be either a PEG-free helper lipid or in particular a PEG-containing helper lipid, surprising effects can be realized, more particularly if the content of any of this kind of helper lipid is contained within the concentration range specified herein.

In a further aspect of the present invention, lipid compositions which are preferably present as lipoplexes or liposomes, preferably show a neutral or overall anionic charge. The anionic lipid is preferably any neutral or anionic lipid described herein. The lipid composition comprises in a preferred embodiment any helper lipid or helper lipid combination as well as any ALK5 inhibitor as described herein (for example, TB4). In a further embodiment the composition according to the present invention containing nucleic acid(s) forms lipoplexes. In a preferred embodiment the term lipoplexes as used herein refers to a composition composed of neutral or anionic lipid, neutral helper lipid and ALK5 inhibitor of the invention. For reference into the usage of helper lipids in the art, see, by way of example, U.S. Patent Application Publication 2011/0178164; OJEDA, et. al., Int. J. of Pharmaceutics (March 2016); DABKOWSKA, et. al., J. R. Soc. Interface 9, pp. 548-561 (2012); and MOCHIZUKI, et. al., Biochimica et. Biophysica Acta, 1828, pp. 412-418 (2013).

In a preferred embodiment, the helper lipids of the invention comprise the helper lipids set forth in Table II.

In one embodiment, a TB Prodrug comprises a lipid of the invention, wherein the lipid is CHEMS and wherein the drug moiety is TB4.

In one embodiment, a TB Prodrug comprises a lipid of the invention, wherein the lipid is CHEMS and wherein the drug moiety is TB4, further comprising a LU and wherein the LU is a hydromethylcarbamate linker.

In one embodiment, a TB Prodrug comprises a lipid of the invention, wherein the lipid is CHEMS and wherein the drug moiety is TB4, further comprising a LU and wherein the LU is a hydromethylcarbamate linker, further comprising a helper lipid component, wherein the helper lipid component comprises a helper lipid of Table II.

In one embodiment, a TB Prodrug comprises a lipid of the invention, wherein the lipid is CHEMS and wherein the drug moiety is TB4 and wherein the CHEMS is monovalent.

In one embodiment, a TB Prodrug comprises a lipid of the invention, wherein the lipid is Stearic Acid and wherein the drug moiety is TB4.

In one embodiment, a TB Prodrug comprises a lipid of the invention, wherein the lipid is Stearic Acid and wherein the drug moiety is TB4 and wherein the Stearic Acid is monovalent.

In one embodiment, a TB Prodrug comprises a lipid of the invention, wherein the lipid is Stearic Acid and wherein the drug moiety is TB4, further comprising a LU and wherein the LU is a hydromethylcarbamate linker.

In one embodiment, a TB Prodrug comprises a lipid of the invention, wherein the lipid is Stearic Acid and wherein the chemical composition is TB4, further comprising a LU and wherein the LU is a hydromethylcarbamate linker, further comprising a helper lipid component, wherein the helper lipid component comprises a helper lipid of Table II.

In one embodiment, a TB Prodrug comprises a lipid of the invention, wherein the lipid is Stearic Acid and wherein the drug moiety is TB4 and wherein the TB Prodrug has the following chemical structure:

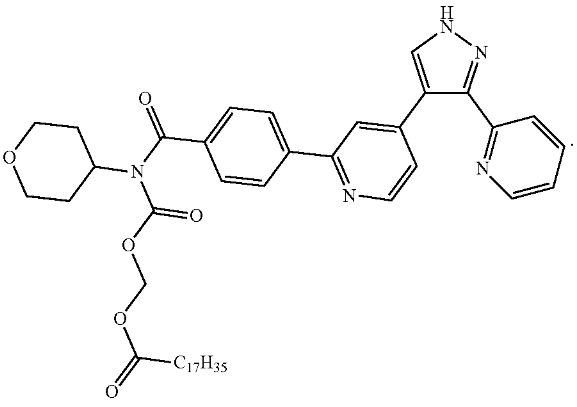

One of ordinary skill in the art will appreciate and be enabled to make variations and modifications to the disclosed embodiment without altering the function and purpose of the invention disclosed herein. Such variations and modifications are intended within the scope of the present disclosure.

V.) Linkage Unit(s) ("LU")

In some embodiments, the presently disclosed subject matter provides prodrugs comprising drug-lipid conjugates that include biodegradable linkages, such as esters, thioesters, and other linkers known in the art.

Exemplary embodiments of ester chemistry are set forth herein:

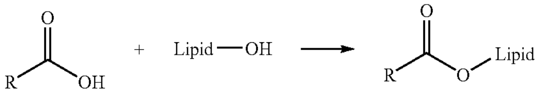

In some embodiments, the prodrug is a drug-lipid conjugate, whereby the drug-lipid conjugate is cleaved by an esterase.

In one embodiment, a prodrug of the invention comprises a LU via a secondary amine, amide, or aniline using the following schema:

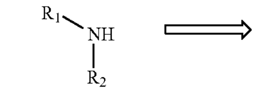

Secondary Amine, amide, or aniline

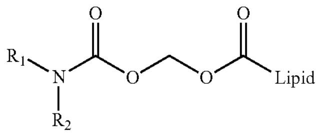

Prodrug Structure

An exemplary synthesis is as follows:

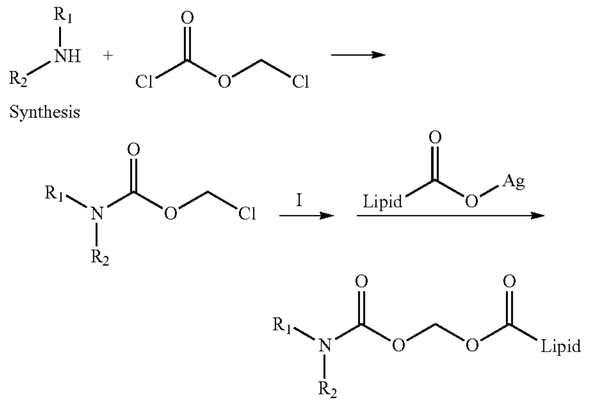

Cleavage of the prodrug structure comprising a secondary amine, amide, or aniline is obtained via esterase hydrolysis of the secondary amine, amide, or aniline prodrug under the following exemplary synthesis:

Esterase Hydrolysis of Secondary Amine/Amide/Aniline Prodrug

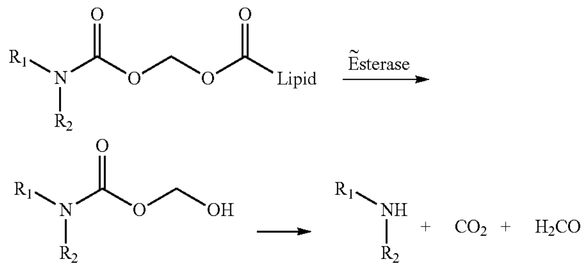

Hydrolytically Unstable

Wherein:

$R_1$—NH—$R_2$ can be any molecule with a secondary amine, amide, or aniline.

In one embodiment, the secondary amide nitrogen of the TB4 drug moiety is conjugated to CHEMS via a hydromethylcarbamate linker.

One of ordinary skill in the art will appreciate and be enabled to make variations and modifications to the disclosed embodiment without altering the function and purpose of the invention disclosed herein. Such variations and modifications are intended within the scope of the present disclosure.

VI.) Nanocarrier(s)

Generally speaking, and for the purposes of this disclosure nanocarrier(s) are within the scope of the invention. A nanocarrier is nanomaterial being used as a transport module for another substance, such as a drug. Commonly used nanocarriers include micelles, polymers, carbon-based materials, liposomes, and other substances. Because of their small size, nanocarriers can deliver drugs to otherwise inaccessible sites around the body. Nanocarriers can include polymer conjugates, polymeric nanoparticles, lipid-based carriers, dendrimers, carbon nanotubes, and gold nanoparticles. Lipid-based carriers include both liposomes, solid-lipid nanoparticles, and micelles. In certain embodiments the nanocarrier is a liposome, lipid nanoparticle ("LNP") or a solid-lipid nanoparticle ("SLNP").

In addition, nanocarriers are useful in the drug delivery process because they can deliver drugs to site-specific targets, allowing drugs to be delivered in certain organs or cells but not in others. Site-specificity poses a major therapeutic benefit since it prevents drugs from being delivered to the wrong places. In addition, nanocarriers show promise for use in chemotherapy because they can help decrease the adverse, broader-scale toxicity of chemotherapy on healthy, fast growing cells around the body. Since chemotherapy drugs can be extremely toxic to human cells, it is important that they are delivered to the tumor without being released into other parts of the body.

Generally speaking, there are four (4) methods in which nanocarriers can deliver drugs and they include passive targeting, active targeting, pH specificity, and temperature specificity.

Passive targeting refers to a nanocarrier's ability to travel down a tumor's vascular system, become trapped, and accumulate in the tumor. This accumulation is caused by the enhanced permeability and retention effect. The leaky vasculature of a tumor is the network of blood vessels that form in a tumor, which contain many small pores. These pores allow nanocarriers in, but also contain many bends that allow the nanocarriers to become trapped. As more nanocarriers become trapped, the drug accumulates at the tumor site. This accumulation causes large doses of the drug to be delivered directly to the tumor site.

Active targeting involves the incorporation of targeting modules such as ligands or antibodies on the surface of nanocarriers that are specific to certain types of cells around the body. Generally, nanocarriers have a high surface-area to volume ratio allowing for multiple ligands to be incorporated on their surfaces.

Additionally, certain nanocarriers will only release the drugs they contain in specific pH ranges. pH specificity also allows nanocarriers to deliver drugs directly to a tumor site. This is due to the fact that tumors are generally more acidic than normal human cells, with a pH around 6.8. Normal tissue has a pH of around 7.4. Thus, nanocarriers that only release drugs at certain pH ranges can therefore be used to release the drug only within acidic tumor environments. High acidic environments cause the drug to be released due to the acidic environment degrading the structure of the nanocarrier. Generally, these nanocarriers will not release drugs in neutral or basic environments, effectively targeting the acidic environments of tumors while leaving normal body cells untouched. This pH sensitivity can also be induced in micelle systems by adding copolymer chains to micelles that have been determined to act in a pH independent manor. See, W U, et. al., Biomaterials, 34(4): 1213-1222 (2012). These micelle-polymer complexes also help to prevent cancer cells from developing multi-drug resistance. The low pH environment triggers a quick release of the micelle polymers, causing a majority of the drug to be released at once, rather than gradually like other drug treatments.

Additionally, some nanocarriers have also been shown to deliver drugs more effectively at certain temperatures. Since tumor temperatures are generally higher than temperatures throughout the rest of the body, around 40° C., this temperature gradient helps act as safeguard for tumor-specific site delivery. See, REZAEI, et. al., Polymer, 53(16): 3485-3497 (2012).

As disclosed herein, lipid-based nanocarriers, such as liposomes are within the scope of this invention. Lipid-based nanoparticles (LBNPs or LNPs) such as liposomes, solid lipid nanoparticles (SLN) and nanostructured lipid carriers (NLC) can transport hydrophobic and hydrophilic molecules, display minimal or no toxicity, and increase the time of drug action by means of a prolonged half-life and a controlled release of the drug. Lipid nanoparticles can include chemical modifications to avoid the detection by the immune system (gangliosides or polyethylene glycol (PEG)) or to improve the solubility of the drug. In addition, they can be prepared in formulations sensitive to the pH in order to promote drug release in an acid environment and can also be associated with small molecules or antibodies that recognize tumor cells or their receptors (such as folic acid (FoA)). Nanodrugs can also be used in combination with other therapeutic strategies to improve the response of patients. See, GARCIA-PINEL, et. al., Nanomaterials 9(639) (2019).

In various embodiments silica some drug carriers described herein comprise a porous silica (or other material) nanoparticle (e.g., a silica body having a surface and defining a plurality of pores that are suitable to receive molecules therein) coated with a lipid bilayer. The fact that the nanoparticle is referred to as a silica nanoparticle does not preclude materials other than silica from also being incorporated within the silica nanoparticle. In some embodiments, the silica nanoparticle may be substantially spherical with a plurality of pore openings through the surface providing access to the pores. However, in various embodiments the silica nanoparticle can have shapes other than substantially spherical shapes. Thus, for example, in certain embodiments the silica nanoparticle can be substantially ovoid, rod-shaped, a substantially regular polygon, an irregular polygon, and the like.

Generally, the silica nanoparticle comprises a silica body that defines an outer surface between the pore openings, as well as side walls within the pores. The pores can extend through the silica body to another pore opening, or a pore can extend only partially through the silica body such that that it has a bottom surface of defined by the silica body.

In some embodiments, the silica body is mesoporous. In other embodiments, the silica body is microporous. As used herein, "mesoporous" means having pores with a diameter between about 2 nm and about 50 nm, while "microporous" means having pores with a diameter smaller than about 2 nm. In general, the pores may be of any size, but in typical embodiments are large enough to contain one or more therapeutic compounds therein. In such embodiments, the pores allow small molecules, for example, therapeutic compounds such as anticancer compounds to adhere or bind to the inside surface of the pores, and to be released from the silica body when used for therapeutic purposes. In some embodiments, the pores are substantially cylindrical.

In certain embodiments the nanoparticles comprise pores having pore diameters between about 1 nm and about 10 nm in diameter or between about 2 nm and about 8 nm. In certain embodiments the nanoparticles comprise pores having pore diameters between about 1 nm and about 6 nm, or between about 2 nm and about 5 nm. Other embodiments include particles having pore diameters less than 2.5 nm.

In other embodiments, the pore diameters are between 1.5 and 2.5 nm. Silica nanoparticles having other pore sizes may be prepared, for example, by using different surfactants or swelling agents during the preparation of the silica nanoparticles. In various embodiments the nanoparticles can include particles as large (e.g., average, or median diameter (or another characteristic dimension) as about 1000 nm. However, in various embodiments the nanoparticles are typically less than 500 nm or less than about 300 nm as, in general, particles larger than 300 nm may be less effective in entering living cells or blood vessel fenestrations. In certain embodiments the nanoparticles range in size from about 40 nm, or from about 50 nm, or from about 60 nm up to about 100 nm, or up to about 90 nm, or up to about 80 nm, or up to about 70 nm. In certain embodiments the nanoparticles range in size from about 60 nm to about 70 nm. Some embodiments include nanoparticles having an average maximum dimension between about 50 nm and about 1000 nm. Other embodiments include nanoparticles having an average maximum dimension between about 50 nm and about 500 nm. Other embodiments include nanoparticles having an average maximum dimension between about 50 nm and about 200 nm.

In some embodiments, the average maximum dimension is greater than about 20 nm, greater than about 30 nm, greater than 40 nm, or greater than about 50 nm. Other embodiments include nanoparticles having an average maximum dimension less than about 500 nm, less than about 300 nm, less than about 200 nm, less than about 100 nm or less than about 75 nm. As used herein, the size of the nanoparticle refers to the average or median size of the primary particles, as measured by transmission electron microscopy (TEM) or similar visualization techniques known in the art. Further examples of mesoporous silica nanoparticles include, but are not limited to, MCM-41, MCM-48, and SBA-15. See, KATIYARE, et. al., J. Chromotog. 1122(1-2): 13-20 (2006).

Methods of making porous silica nanoparticles are well known to those of skill in the art. In certain embodiments mesoporous silica nanoparticle are synthesized by reacting tetraethyl orthosilicate (TEOS) with a template made of micellar rods. The result is a collection of nano-sized spheres or rods that are filled with a regular arrangement of pores. The template can then be removed by washing with a solvent adjusted to the proper pH (See, e.g., TREWYN et al. (2007) Chem. Eng. J. 137(1): 23-29).

In certain embodiments mesoporous particles can also be synthesized using a simple sol-gel method (See, e.g., NANDIYANTO, et al. (2009) Microporous and Mesoporous Mat. 120(3): 447-453). In certain embodiments tetraethyl orthosilicate can also be used with an additional polymer monomer as a template. In certain embodiments 3-mercaptopropyl)trimethoxysilane (MPTMS) is used instead of TEOS.

In certain embodiments the mesoporous silica nanoparticles are cores are synthesized by a modification of the sol/gel procedure described by MENG et. al. (2015) ACS Nemo, 9(4): 3540-3557.

While the methods described herein have been demonstrated with respect to porous silica nanoparticles (e.g., mesoporous silica), it will be recognized by those skilled in the art that similar methods can be used with other porous nanoparticles. Numerous other mesoporous materials that can be used in drug delivery nanoparticles are known to those of skill in the art. For example, in certain embodiments mesoporous carbon nanoparticles could be utilized.

Mesoporous carbon nanoparticles are well known to those of skill in the art (See, e.g., HUANG et. al. (2016) Carbon, 101:135-142; ZHU et. al. (2014) Asian J. Pharm. Sci., 9(2): 82-91; and the like).

Similarly, in certain embodiments, mesoporous polymeric particles can be utilized. The syntheses of highly ordered mesoporous polymers and carbon frameworks from organic-organic assembly of triblock copolymers with soluble, low-molecular-weight phenolic resin precursors (resols) by an evaporation induced self-assembly strategy have been reported by MENG, et. al. (2006) Chem. Mat. 6(18): 4447-4464.

The nanoparticles described herein are illustrative and non-limiting. Using the teachings provided herein numerous other lipid bilayer coated nanoparticles will be available to one of skill in the art.

In one embodiment, the invention teaches nanocarriers which comprise TB Prodrugs.

In one embodiment, the invention teaches a nanocarrier comprising a liposome, wherein the lipid comprises CHEMS.

In one embodiment, the invention teaches a nanocarrier comprising a liposome, wherein the lipid comprises Stearic Acid.

In one embodiment, the invention teaches a nanocarrier comprising a liposome, wherein the lipid comprises CHEMS and whereby the liposome further comprises a TB Prodrug.

In one embodiment, the invention teaches a nanocarrier comprising a liposome, wherein the lipid comprises CHEMS and whereby the liposome further comprises TB4.

In one embodiment, the invention teaches a nanocarrier comprising a liposome, wherein the lipid comprises Stearic Acid and whereby the liposome further comprises an ALK5 inhibitor.

In one embodiment, the invention teaches a nanocarrier comprising a liposome, wherein the lipid comprises Stearic Acid and whereby the liposome further comprises TB4.

In one embodiment, the invention teaches a nanocarrier comprising a liposome, wherein the lipid comprises Stearic Acid and whereby the liposome further comprises TB4 (denoted LNP-TB4).

In a further embodiment, the invention teaches a nanocarrier comprising a liposome, wherein the lipid comprises Stearic Acid and whereby the liposome further comprises TB4 and whereby the liposome is co-formulated with 103 (denoted LNP-TB4-ID3).

In a preferred embodiment, the lipid particle comprises a solid-lipid nanoparticle (SLNP) comprising a liposome which comprises TB4-Prodrug.

In one embodiment, the invention teaches a nanocarrier comprising a solid-lipid nanoparticle ("SLNP"), wherein the solid-lipid nanoparticle comprises Stearic Acid and whereby the solid-lipid nanoparticle further comprises TB4 (denoted SLNP-TB4).

In a further embodiment, the invention teaches a nanocarrier comprising a solid-lipid nanoparticle ("SLNP"), wherein the solid-lipid nanoparticle comprises Stearic Acid and whereby the solid-lipid nanoparticle further comprises TB4 and whereby the SLNP is co-formulated with ID3 (denoted SLNP-TB4-ID3).

In a further preferred embodiment, the solid-lipid nanoparticle of the invention comprises a composition having the following ratio(s):

| Constituent of the SLNP | Amount (% w/w) |
|---|---|
| Lipid 1 (lipid-prodrug) | 5-80 |
| Lipid 2 (lipid-prodrug) | 0-40 |
| Helper lipids | 0-80 |
| DSPE-PEG2000 | 0-10 |
| Stabilizer(s) | 0.5-20 |

Whereby Lipid 1 comprises a TB4-Prodrug, wherein the lipid moiety comprises Stearic Acid and whereby the helper lipids are the helper lipids set forth in Table II and whereby the stabilizers are selected from the group consisting of polyvinyl alcohol (e.g., Moliwol 488), poloxamers (e.g., Pluronic F127), Tween 80, PEG400, and Kolliphor RH 40 and whereby Lipid 2 (lipid prodrug) comprises a lipid prodrug of the disclosure or a lipid prodrug selected from the group consisting of ID3, AR5, TR3, ID1 inhibitors (for examples ID3-STEA, ID3-CHEM, AR5-STEA, TR3-STEA, ID1-CHOL, etc.), MPLA, and Telratolimod.

One of ordinary skill in the art will appreciate and be enabled to make variations and modifications to the disclosed embodiment without altering the function and purpose of the invention disclosed herein. Such variations and modifications are intended within the scope of the present disclosure.

Additionally, the scope of the present disclosure teaches three (3) possible treatment modalities using the formulated prodrugs of the invention. See, PCT Patent Publication No. WO2018/213631.

The first treatment modality involves combination of a TB Prodrug in combination with another therapeutic (e.g., another formulated prodrug which inhibits ALK5 and other family members, a chemotherapy agent (such as an ICD-inducing chemotherapy), etc.) into a single liposome that allows systemic (or local) biodistribution and drug delivery to tumor sites. The dual-delivery approach achieves synergistic enhancement of adaptive and innate immunity, leading to a significant improvement in animal survival. In certain embodiments the nanocarrier comprises a vesicle (i.e., a lipid bilayer enclosing a fluid).

A second treatment modality involves local delivery to a tumor or peri-tumoral region, of an agent that inhibits ALK5 and other family members in combination with a lipid (e.g., a liposome) that comprises an inhibitor of ALK5 signaling.

A third treatment modality involves vaccination utilizing dying cancer cells (e.g., KPC cells) in which inhibition of ALK5 is induced ex vivo. It is discovered that such vaccination can generate a systemic immune response that can interfere with tumor growth at a remote site as well as allowing adoptive transfer to non-immune animals. One of skill in the art will appreciate and be enabled to perform methods the treatment modalities provided herein.

VII.) Liposomes

In one aspect, the presently disclosed subject matter is based on an approach for providing a TB Prodrug of the disclosure (See, section entitled Prodrugs) suitable for incorporation into a nanocarrier comprising lipid coating layers to provide enhanced delivery of the corresponding prodrugs and for providing combination therapies including the prodrugs. The advantages for using prodrugs of the invention include the facilitation of controlled formulation into an LNP of the disclosure (e.g., a liposome). This allows the prodrug to be maintained in an inactive form during systemic circulation, which allows the liposome to release the active agent after engulfment by a cell, for example within a tumor.

In certain embodiments one or more TB Prodrugs (e.g., any one or more of the TB Prodrugs inhibitors taught in Formula I, Formula II, Formula III, and/or a TB4-Prodrug) (See, section entitled prodrugs) are formulated a lipid moiety that forms a vesicle (e.g., a liposome) structure in aqueous solution or that can form a component of a lipid bilayer comprising a liposome. The liposomes can be used directly, provided as components in a combined formulation (e.g., in combination with another drug moiety or therapeutic modality as disclosed herein).

In certain embodiments, the liposome that is formulated with the TB Prodrug comprises a lipid, PHGP, vitamin E, cholesterol, and/or a fatty acid.

In one embodiment, the liposome comprises cholesterol.

In one embodiment, the liposome comprises DSPC.

In one embodiment, the liposome comprises HSPC.

In one embodiment, the liposome comprises DSPE-$PEG_{2000}$.

In one embodiment, the liposome comprises DPPG.

In one embodiment, the liposome comprises DMPG.

In one embodiment, the liposome Lyso PC.

In one embodiment, the liposome (Δ9-Cis) PG.

In one embodiment, the liposome comprises Soy Lyso PC.

In one embodiment, the liposome comprises PG.

In one embodiment, the liposome comprises PA-PEG3-mannose.

In one embodiment, the liposome comprises C16 PEG2000 Ceramide.

In one embodiment, the liposome comprises MPLA.

In one embodiment, the liposome comprises CHEMS.

In one embodiment, the liposome comprises Stearic Acid.

In one embodiment, the liposome comprises a phospholipid set forth in Table III.

In one embodiment, the liposome comprises TB4 and further comprises CHEMS and further comprises a LU wherein said LU is a hydromethylcarbamate linker.

In one embodiment, the liposome comprises TB4 and further comprises Stearic Acid and further comprises a LU wherein said LU is a hydromethylcarbamate linker.

In one embodiment, the liposome comprises TB4 and further comprises CHEMS and further comprises a LU wherein said LU is a hydromethylcarbamate linker and further comprises a helper lipid set forth in Table II.

In one embodiment, the liposome comprises TB4 and further comprises a Stearic Acid and further comprises a LU wherein said LU is a hydromethylcarbamate linker and further comprises a helper lipid set forth in Table II.

In one embodiment, the liposome of the disclosure comprises a TB Prodrug co-formulated with one or more additional immune modulating agents, whereby the immune modulating agents includes, but is not limited to, immunogenic-cell death inducing chemotherapeutics, toll receptor agonists, sting agonists, IDO inhibitors, CTLA4 inhibitors, PD-1 inhibitors, and/or prodrugs thereof.

In a preferred embodiment, the liposome comprises a TB Prodrug co-formulated with an ICD-inducing Chemotherapeutic.

In a preferred embodiment, the liposome comprises a TB Prodrug co-formulated with an ICD-inducing Chemotherapeutic selected from the list: doxorubicin (DOX), mitoxantrone (MTO), Oxaliplatin (OXA), Cyclophosphamide (CP), Bortezomib, Carfilzomib, or Paclitaxel.

In a preferred embodiment, the liposome comprises a TB Prodrug co-formulated with a Toll Receptor TLR agonist/Prodrug.

In a further preferred embodiment, the Toll Receptor TLR agonist/Prodrug is selected from the group consisting of TR3, TR4, TR5, and TR6.

In a preferred embodiment, the liposome comprises a TB Prodrug co-formulated with Toll Receptor (TLR) agonist/Prodrug selected from the list: Resiquimod (R848), Gardiquimod, 852A, DSR 6434, Telratolimod, CU-T12-9, monophosphoryl Lipid A (MPLA), 3D(6-acyl)-PHAD®, SMU127, Pam3CSK4, or 3D-PHAD® or prodrugs thereof In a preferred embodiment, the liposome comprises a TB Prodrug co-formulated with a PD-1 inhibitor/Prodrug.

In a preferred embodiment, the liposome comprises a TB Prodrug co-formulated with a PD-1 inhibitor/Prodrug, selected from the list: AUNP12, CA-170, or BMS-986189 or prodrugs thereof.

In a preferred embodiment, the liposome comprises a TB Prodrug co-formulated with an IDO-1 inhibitor/Prodrug.

In a preferred embodiment, the liposome comprises a TB Prodrug co-formulated with an IDO-1 inhibitor/Prodrug, selected from the list epacadostat, L-1-methyl tryptophan (Indoximod), D-1-methyl tryptophan, Linrodostat mesylate (BMS 986205), MK-7162, LY-3381916, KHK-2455, HTI-1090, DN-1406131, or BGB-5777.

In a preferred embodiment, the liposome comprises a TB Prodrug co-formulated with doxorubicin (DOX).

In a preferred embodiment, the liposome comprises a TB Prodrug co-formulated with mitoxantrone (MTO).

In a preferred embodiment, the liposome comprises a TB Prodrug co-formulated with doxorubicin (DOX) and an PD-1 prodrug.

In a preferred embodiment, the liposome comprises a TB Prodrug co-formulated with mitoxantrone (MTO) and a PD-1 prodrug.

In a preferred embodiment, the liposome comprises a TB Prodrug co-formulated with doxorubicin (DOX) and an IDO-1 prodrug.

In a preferred embodiment, the liposome comprises a TB Prodrug co-formulated with mitoxantrone (MTO) and an IDO-1 prodrug.

In a preferred embodiment, the liposome comprises a TB Prodrug co-formulated with doxorubicin (DOX) and a TLR agonist/prodrug.

In a preferred embodiment, the liposome comprises a TB Prodrug co-formulated with mitoxantrone (MTO) and a TLR agonist/prodrug.

In a preferred embodiment, the liposome comprises a TB Prodrug co-formulated with doxorubicin (DOX) and a PD-1 prodrug and a TLR agonist/prodrug.

In a preferred embodiment, the liposome comprises a TB Prodrug co-formulated with mitoxantrone (MTO) and a PD-1 prodrug and a TLR agonist/prodrug.

In a preferred embodiment, the liposome comprises a TB Prodrug co-formulated with a TLR agonist/prodrug.

In a preferred embodiment, the liposome comprises a TB Prodrug co-formulated with an IDO antagonist/prodrug.

In a preferred embodiment, the liposome comprises a TB Prodrug co-formulated with a CD1D agonist/prodrug.

In a preferred embodiment, the liposome comprises a TB Prodrug co-formulated with a TLR agonist/prodrug and a PD-1 prodrug.

In a preferred embodiment, the liposome comprises a TB Prodrug co-formulated with a TLR agonist/prodrug and an IDO-1 prodrug.

In a preferred embodiment, the liposome comprises TB4-Prodrug co-formulated with doxorubicin (DOX).

In a preferred embodiment, the liposome comprises TB4-Prodrug co-formulated with mitoxantrone (MTO).

In a preferred embodiment, the liposome comprises TB4-Prodrug co-formulated with doxorubicin (DOX) and/or and IDO prodrug and/or a TLR agonist/prodrug.

In a preferred embodiment, the liposome comprises TB4-Prodrug co-formulated with mitoxantrone (MTO) and/or and IDO prodrug and/or a TLR agonist/prodrug.

One of skill in the art will appreciate and understand that solubility is one of most common problems faced by the artisan in the drug development process. Chemical conjugation of a drug/anti-cancer agents via lipid molecules (i.e., lipid-based prodrugs) provides a platform to solve the problem of formulating the drugs in an aqueous suspension. The major advantages of delivering drug(s) with lipid conjugation (lipid-based prodrugs) lies on its ability to improve pharmacokinetics/half-life and targeted delivery.

With suitable selection of lipid molecules, lipid-based prodrug(s) can be integrated/formulated in a liposomal formulation using techniques known in the art, which has many more advantages over conventional drug delivery system. (KOHLI, et. al., J. Control Release, 0: pp 274-287 (Sep. 28, 2014); and GARCIA-PINEL, et. al., Nanomaterials 9:638 (2019). The advantage of combining lipid-prodrug with liposomes is twofold: (i) liposomes containing lipid-prodrug not only increase the solubility of the drug/prodrug itself, but (ii) also have the ability to encapsulate multiple drugs (both hydrophilic and lipophilic) (see, section entitled nanocarriers).

For the purposes of this disclosure, the major advantage of liposome formulations are as follows:

i) biocompatibility/biodegradability and no general toxicity of the liposome's formulations;
ii) flexibility and manipulation of size and surface charge depending on the required purpose. Liposome formulation(s), for the purposes of this disclosure, can have a size range of 40-150 nm in diameter and a surface charge in the range of −40 to +40 mV; and
iii) Liposomes of the invention have either a single or multiple lipid-prodrugs as the constituent lipid portion of the liposome(s). Additionally, multiple drugs (e.g., that work in different mechanism of action) and with different solubility profile (hydrophilic or lipophilic) can be formulated (either in the lipid bilayers or in the hydrophilic core) in these liposomes.

As one of ordinary skill in the art will appreciate, all methods of making liposomes involve four (4) basic stages:

(i) Drying down lipids from organic solvent;
(ii) Dispersing the lipid in aqueous solution;
(iii) Purifying the resultant liposome; and
(iv) Analyzing the final product.

See, AKBARZADEH, et. al., Nanoscale Research Letters, 8:102 (2013).

Another aspect of the invention discloses liposomal encapsulation technology (LET) which is a delivery technique used to transmit drugs. LET is a method of generating sub-microscopic foams called liposomes, which encapsulate numerous materials. These 'liposomes' form a barrier around their contents, which is resistant to enzymes in the mouth and stomach, alkaline solutions, digestive juices, bile salts, and intestinal flora that are generated in the human body, as well as free radicals. The contents of the liposomes are, therefore, protected from oxidation and degradation. This protective phospholipid shield or barrier remains undamaged until the contents of the liposome are delivered to the exact target gland, organ, or system where the contents will be utilized (See, section entitled nanocarriers).

In one embodiment, liposome(s) of the disclosure are synthesized using a plurality of different ratios of TB Prodrugs, lipids, and/or lipid-prodrugs. As disclosed herein, the TB Prodrugs may comprise helper lipids as disclosed herein (See, for example Table II).

In one embodiment, liposome(s) of the disclosure are synthesized using a plurality of different ratios of TB Prodrugs, lipids, and/or lipid-prodrugs. As disclosed herein, the TB Prodrugs may further comprise DSPE-PEGs.

In a preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Lipid 2 (lipid-prodrug) | 0-40 |
| Helper lipids | 50-80 |
| DSPE-PEG 2000 | 2-5 |

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 50-80 |
| DSPEG-PEG 2000 | 2-5 |

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 50-80 |
| DSPEG-PEG 2000 | 2-5 |

Whereby Lipid 1 comprises a TB4-Prodrug, wherein the lipid moiety comprises CHEMS.

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 50-80 |
| DSPEG-PEG 2000 | 2-5 |

Whereby Lipid 1 comprises a TB4-Prodrug, wherein the lipid moiety comprises Stearic Acid.

One of ordinary skill in the art will appreciate and be enabled to make variations and modifications to the disclosed embodiment without altering the function and purpose of the invention disclosed herein. Such variations and modifications are intended within the scope of the present disclosure.

VIII.) Pharmaceutical Formulation

As used herein, the term "drug" is synonymous with "pharmaceutical". In certain embodiments, the liposome of the disclosure is fabricated to an encapsulated dosage form to and given to a patient for the treatment of disease.

Generally speaking, pharmaceutical formulation is the process in which different chemical substances are combined to a pure drug substance to produce a final drug product. Formulation studies involve developing a preparation of the drug which is both stable and acceptable to the patient. For orally taken drugs, this usually involves incorporating the drug into a tablet or a capsule. It is important to appreciate that a dosage form contains a variety of other substances apart from the drug itself, and studies have to be carried out to ensure that the drug is compatible with these other substances.

An excipient is an inactive substance used as a carrier for the active ingredients of a drug product, in this case a liposome comprising a TB Prodrug. In addition, excipients can be used to aid the process by which a drug product is manufactured. The active substance is then dissolved or mixed with an excipient. Excipients are also sometimes used to bulk up formulations with very potent active ingredients, to allow for convenient and accurate dosage. Once the active ingredient has been purified, it cannot stay in purified form for an extended period of time. In many cases it will denature, fall out of solution, or stick to the sides of the container.

To stabilize the active ingredient, excipients are added to ensure that the active ingredient stays active and is stable for a long enough period of time that the shelf-life of the product makes it competitive with other products and safe for the end-user. Examples of excipients include but are not limited to, anti-adherents, binders, coatings, disintegrants, fillers, diluents, flavors, colors, lubricants, and preservatives. The final formulation comprises and active ingredient and excipients which are then enclosed in the pharmaceutical dosage form.

Pre-formulation involves the characterization of a drug's physical, chemical, and mechanical properties in order to choose what other ingredients should be used in the preparation. Formulation studies then consider such factors as stability, particle size, polymorphism, pH, and solubility, as all of these can influence bioavailability and hence the activity of a drug. The drug must be combined with inactive additives by a method which ensures that the quantity of drug present is consistent in each dosage unit (e.g., each vial). The dosage should have a uniform appearance.

It is unlikely that these studies will be complete by the time clinical trials commence. This means that simple preparations are developed initially for use in phase I clinical trials. These typically consist of vials, hand-filled capsules containing a small amount of the drug and a diluent. Proof of the long-term stability of these formulations is not required, as they will be used (tested) in a matter of days. However, long-term stability is critical in supply chain management since the time the final formulation is packaged until it reaches the patient can be several months or years. Consideration has to be given to what is called the drug load (i.e., the ratio of the active drug to the total contents of the dose). A low drug load may cause homogeneity problems. A high drug load may pose flow problems or require large capsules if the compound has a low bulk density. By the time phase III clinical trials are reached, the formulation of the drug should have been developed to be close to the preparation that will ultimately be used in the market.

A knowledge of stability is essential by this stage, and conditions must have been developed to ensure that the drug is stable in the preparation. If the drug proves unstable, it will invalidate the results from clinical trials since it would be impossible to know what the administered dose actually was. Stability studies are carried out to test whether temperature, humidity, oxidation, or photolysis (ultraviolet light or visible light) have any effect, and the preparation is analyzed to see if any degradation products have been formed. It is also important to check whether there are any unwanted interactions between the preparation and the container. If a plastic container is used, tests are carried out to see whether any of the ingredients become adsorbed on to the plastic, and whether any plasticizers, lubricants, pigments, or stabilizers leach out of the plastic into the preparation. Even the adhesives for the container label need to be tested, to ensure they do not leach through the plastic container into the preparation. The way a drug is formulated can avoid some of the problems associated with oral administration. Drugs are normally taken orally as tablets or capsules. The drug (active substance) itself needs to be soluble in aqueous solution at a controlled rate. Such factors as particle size and crystal form can significantly affect dissolution. Fast dissolution is not always ideal. For example, slow dissolution rates can prolong the duration of action or avoid initial high plasma levels.

In some embodiments, the nanocarrier (e.g., a liposome comprising an TB prodrug) and/or the liposome comprising a TB prodrug and co-formulated with an immune modulating agent are administered alone or in a mixture with a physiologically acceptable carrier (such as physiological saline or phosphate buffer) selected in accordance with the route of administration and standard pharmaceutical practice. For example, when used as an injectable, the nanocarriers can be formulated as a sterile suspension, dispersion, or emulsion with a pharmaceutically acceptable carrier. In certain embodiments normal saline can be employed as the pharmaceutically acceptable carrier. Other suitable carriers include, e.g., water, buffered water, 0.4% saline, 0.3% glycine, 5% glucose and the like, including glycoproteins for enhanced stability, such as albumin, lipoprotein, globulin, etc. In compositions comprising saline or other salt-containing carriers, the carrier is preferably added following nanocarrier formation. Thus, after the nanocarrier is formed and loaded with suitable drug(s), the nanocarrier can be diluted into pharmaceutically acceptable carriers such as normal saline. Similarly, the TB prodrug liposomes can be introduced into carriers that facilitate suspension of the nanomaterials (e.g., emulsions, dilutions, etc.).

The pharmaceutical compositions may be sterilized by conventional, well-known sterilization techniques. The resulting aqueous solutions, suspensions, dispersions, emulsions, etc., may be packaged for use or filtered under aseptic conditions. In certain embodiments the drug delivery nanocarriers (e.g., LB-coated nanoparticles) are lyophilized, the lyophilized preparation being combined with a sterile aqueous solution prior to administration. The compositions may also contain pharmaceutically acceptable auxiliary substances as required to approximate physiological conditions, such as pH-adjusting and buffering agents, tonicity adjusting agents and the like, for example, sodium acetate, sodium lactate, sodium chloride, potassium chloride, calcium chloride, etc.

Additionally, in certain embodiments, the pharmaceutical formulation may include lipid-protective agents that protect lipids against free-radical and lipid-peroxidative damage on storage. Lipophilic free-radical quenchers, such as alphatocopherol and water-soluble iron-specific chelators, such as ferrioxamine, are suitable and contemplated herein. The concentration of nanocarrier (e.g., liposome comprising TB prodrugs) in the pharmaceutical formulations can vary widely, e.g., from less than approximately 0.05%, usually at least approximately 2 to 5% to as much as 10 to 50%, or to 40%, or to 30% by weight and are selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, nanocarriers composed of irritating lipids may be diluted to low concentrations to lessen inflammation at the site of administration. The amount of nanocarriers administered will depend upon the particular drug used, the disease state being treated and the judgment of the clinician but will generally be between approximately 0.01 and approximately 50 mg per kilogram of body weight, preferably between approximately 0.1 and approximately 5 mg per kg of body weight.

One of skill in the art will appreciate that exact dosages will vary depending upon such factors as the particular TB prodrugs and any co-formulated immune modulating agents and the desirable medical effect, as well as patient factors such as age, sex, general condition, and the like. Those of skill in the art can readily take these factors into account and use them to establish effective therapeutic concentrations without resort to undue experimentation.

For administration to humans (or to non-human mammals) in the curative, remissive, retardive, or prophylactic treatment of diseases described herein the prescribing physician will ultimately determine the appropriate dosage of the drug for a given human (or non-human) subject, and this can be expected to vary according to the age, weight, and response of the individual as well as the nature and severity of the patient's disease. In certain embodiments the dosage of the drug provided by the nanocarrier(s) can be approximately equal to that employed for the free drug. However as noted above, the nanocarriers described herein can significantly reduce the toxicity of the drug(s) administered thereby and significantly increase a therapeutic window. Accordingly, in some cases dosages in excess of those prescribed for the free drug(s) will be utilized.

One of ordinary skill in the art will appreciate and be enabled to make variations and modifications to the disclosed embodiment without altering the function and purpose of the invention disclosed herein. Such variations and modifications are intended within the scope of the present disclosure.

IX.) Combination Therapy

As the skilled artisan will appreciate and understand, cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Thus, the liposomes comprising TB Prodrugs of the present disclosure can be used in combination with one or more other enzyme/protein/receptor inhibitors or one or more therapies for the treatment of diseases, such as cancer or infections. Examples of diseases and indications treatable with combination therapies include those set forth in the present disclosure. Examples of cancers include, but are not limited to, solid tumors and liquid tumors, such as blood cancers. Examples of infections include viral infections, bacterial infections, fungus infections or parasite infections.

For example, the liposomes comprising TB Prodrugs of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, PI3K (alpha, beta, gamma, delta), CSFIR, KIT, FLK-II, KDR/FLK-1, FLK-4, flt-1, FGFR1, FGFR2, FGFR3, FGFR4, c-Met, Ron, Sea, TRKA, TRKB, TRKC, TAM kinases (Axl, Mer, Tyro3), FLT3, VEGFR/F1t2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In further embodiments, the liposomes comprising TB Prodrugs of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), a poly ADP ribose polymerase (PARP) inhibitor such as rucaparib, olaparib, niraparib, veliparib, or talazoparib, an arginase inhibitor (INCB01158), a PD-1 inhibitor, a PD-1/L-1 inhibitor, a PD-1/L-2 inhibitor, a CTLA-4 antagonist, and an adenosine receptor antagonist or combinations thereof.

Additionally, the liposomes comprising TB Prodrugs of the present disclosure can further be used in combination with other methods of treating cancers, for example by chemotherapy, irradiation therapy, tumor-targeted therapy, adjuvant therapy, immunotherapy, or surgery.

Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like.

The liposomes comprising TB Prodrugs can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Other anti-cancer agent(s) include antibody therapeutics such as trastuzumab (Herceptin), antibodies to costimulatory molecules such as CTLA-4 (e.g., ipilimumab), 4-1BB (e.g., urelumab, utomilumab), antibodies to PD-1 and PD-L1/L2, or antibodies to cytokines (IL-10, TGF-.beta., etc.).

Examples of antibodies to PD-1 and/or PD-L1/L2 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

In addition, liposomes comprising TB Prodrugs of the present disclosure can be used in combination with one or more immune checkpoint inhibitors for the treatment of diseases, such as cancer or infections. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2.

In some embodiments, the immune checkpoint molecule is a stimulatory checkpoint molecule selected from CD27, CD28, CD40, ICOS, OX40, GITR and CD137. In further embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In further embodiments, the liposomes comprising TB Prodrugs provided herein can be used in combination with one or more agents selected from KIR inhibitors, TIGIT inhibitors, LAIR1 inhibitors, CD160 inhibitors, 2B4 inhibitors and TGF beta inhibitors.

X.) Methods of Delivering Nanocarriers Comprising TB Prodrugs to a Cell Expressing ALK5

As it is known in the art, a wide variety of compositions and methods for using prodrugs and/or nanocarriers to kill tumor cells are known in the art. In the context of cancers, typical methods entail administering to a mammal having a tumor, a biologically effective amount of a TB prodrug of the disclosure, and/or a nanocarrier of the disclosure comprising a TB prodrug.

A typical embodiment is a method of delivering a therapeutic agent to a cell expressing ALK5, comprising forming a TB prodrug by conjugating a drug moiety of the disclosure with a lipid of the disclosure via a Linkage Unit, and exposing the cell to the TB prodrug.

In one embodiment, the TB prodrug comprises a drug moiety of Formula I and CHEMS conjugated via a LU comprising a hydromethylcarbamate linker.

In one embodiment, the TB prodrug comprises a drug moiety of Formula I and Stearic Acid conjugated via a LU comprising a hydromethylcarbamate linker.

In one embodiment, the TB prodrug comprises a drug moiety of Formula II and CHEMS conjugated via a LU comprising a hydromethylcarbamate linker.

In one embodiment, the TB prodrug comprises a drug moiety of Formula II and Stearic Acid conjugated via a LU comprising a hydromethylcarbamate linker.

In one embodiment, the TB prodrug comprises a drug moiety of Formula III and CHEMS conjugated via a LU comprising a hydromethylcarbamate linker.

In one embodiment, the TB prodrug comprises a drug moiety of Formula III and Stearic Acid conjugated via a LU comprising a hydromethylcarbamate linker.

In one embodiment, the TB prodrug comprises a TB4-Prodrug, whereby the lipid moiety comprises CHEMS conjugated via a LU comprising a hydromethylcarbamate linker.

In one embodiment, the TB prodrug comprises a TB4-Prodrug, whereby the lipid moiety comprises Stearic Acid conjugated via a LU comprising a hydromethylcarbamate linker.

Another illustrative embodiment is a method of treating an individual suspected of suffering from metastasized cancer, comprising a step of administering parenterally to said individual a pharmaceutical composition comprising a therapeutically effective amount of a TB prodrug produced by conjugating a drug moiety with a lipid of the disclosure via a Linkage Unit, and exposing the cell to the TB prodrug.

In one embodiment, the TB prodrug comprises a drug moiety of Formula I and CHEMS conjugated via a LU comprising a hydromethylcarbamate linker.

In one embodiment, the TB prodrug comprises a drug moiety of Formula I and Stearic Acid conjugated via a LU comprising a hydromethylcarbamate linker.

In one embodiment, the TB prodrug comprises a drug moiety of Formula II and CHEMS conjugated via a LU comprising a hydromethylcarbamate linker.

In one embodiment, the TB prodrug comprises a drug moiety of Formula II and Stearic Acid conjugated via a LU comprising a hydromethylcarbamate linker.

In one embodiment, the TB prodrug comprises a drug moiety of Formula III and CHEMS conjugated via a LU comprising a hydromethylcarbamate linker.

In one embodiment, the TB prodrug comprises a drug moiety of Formula III and Stearic Acid conjugated via a LU comprising a hydromethylcarbamate linker.

In one embodiment, the TB prodrug comprises a TB4-Prodrug, whereby the lipid moiety comprises CHEMS conjugated via a LU comprising a hydromethylcarbamate linker.

In one embodiment, the TB prodrug comprises a TB4-Prodrug, whereby the lipid moiety comprises Stearic Acid conjugated via a LU comprising a hydromethylcarbamate linker.

TB Prodrugs, liposomes, and co-formulated liposomes of the present disclosure inhibit the activity of TGFβ protein/protein interaction and, thus, are useful in treating diseases and disorders associated with activity of TGFβ and the diseases and disorders associated with kinase inhibition. In further embodiments of the disclosure, the TB Prodrugs, liposomes, or pharmaceutically acceptable salts or stereoisomers thereof, are useful for therapeutic administration to enhance, stimulate and/or increase immunity in cancer, chronic infection, or sepsis, including enhancement of response to vaccination.

In further embodiments, the present disclosure provides a method for inhibiting the ALK5 T-cell function. The method includes administering to an individual or a patient an TB prodrug, liposomes, SLNPs, and/or of any of the formulas as described herein (e.g., TB4 and/or a TB4-Prodrug), or of an TB prodrug, liposomes, SLNPs, and nano-encapsulated ALK5 inhibitor prodrugs as recited in any of the claims and described herein, or a pharmaceutically acceptable salt or a stereoisomer thereof. The TB Prodrug, liposomes, SLNPs, and nano-encapsulated ALK5 inhibitor prodrugs of the present disclosure can be used alone, in combination with other agents or therapies or as an adjuvant or neoadjuvant for the treatment of diseases or disorders, including cancer and other diseases. For the uses and methods described herein, any of the TB Prodrugs, liposomes, and nano-encapsulated TB Prodrugs of the disclosure, including any of the embodiments thereof, may be used.

In addition, The TB Prodrugs, liposomes, SLNPs, and nano-encapsulated TB Prodrugs of the present disclosure inhibit ALK5 and/or T-cell function, resulting in an TGFβ pathway blockade.

In further embodiments, the present disclosure provides treatment of an individual or a patient in vivo using TB Prodrugs, liposomes, and nano-encapsulated TB Prodrug or a salt or stereoisomer thereof such that growth of cancerous tumors is inhibited.

TB Prodrugs, liposomes, and nano-encapsulated TB Prodrugs, or of any of the formulas as described herein (e.g., TB4-Prodrug), or TB Prodrugs, liposomes, SLNPs, and nano-encapsulated TB Prodrugs as recited in any of the claims and described herein, or a salt or stereoisomer thereof, can be used to inhibit the growth of cancerous tumors.

In the alternative, TB Prodrugs, liposomes, SLNPs, and nano-encapsulated TB Prodrugs of the disclosure, or of any of the formulas as described herein, or a compound as recited in any of the claims and described herein (e.g., TB4-Prodrug), or a salt or stereoisomer thereof, can be used in conjunction with other agents or standard cancer treatments, as described in this disclosure.

In a further embodiment, the present disclosure provides a method for inhibiting growth of tumor cells in vitro. The method includes contacting the tumor cells in vitro with TB Prodrugs, liposomes, and nano-encapsulated TB Prodrugs of the disclosure, or of any of the formulas as described herein (e.g., TB4-Prodrug), or of an TB prodrug, liposomes, SLNPs, and nano-encapsulated TB Prodrugs as recited in any of the claims and described herein, or of a salt or stereoisomer thereof.

In a further embodiment, the present disclosure provides a method for inhibiting growth of tumor cells in a patient. The method includes contacting the tumor cells with TB Prodrugs, liposomes, and nano-encapsulated TB Prodrugs of the disclosure, or of any of the formulas as described herein (e.g., TB4-Prodrug), or of an TB prodrug, liposomes, SLNPs, and nano-encapsulated TB Prodrugs as recited in any of the claims and described herein, or of a salt or stereoisomer thereof.

XI.) Methods of Treating Cancer(s) and Other Immunological Disorder(s)

Another embodiment of the present disclosure is a method for treating cancer. The method comprises administering to a patient, a therapeutically effective amount of a liposome comprising an TB Prodrug (i.e., TB4-Prodrug) herein, a compound as recited in any of the claims and described herein, or a salt thereof. Examples of cancers include those whose growth may be inhibited using ALK5 inhibitors of the disclosure and TB Prodrugs of the disclosure and cancers typically responsive to immunotherapy.

In some embodiments, the present disclosure provides a method of enhancing, stimulating and/or increasing the immune response in a patient. The method includes administering to the patient a therapeutically effective amount of a TB prodrug and/or a nanocarrier comprising the same (i.e., TB4-Prodrug), a compound or composition as recited in any of the claims and described herein, or a salt thereof.

In one embodiment, the method(s) include administering to the patient a therapeutically effective amount of LNP-TB4 or a salt thereof.

In a further embodiment, the method(s) include administering to the patient a therapeutically effective amount of SLNP-TB4 or a salt thereof.

Non-limiting examples of cancers that are treatable using the liposomes comprising TB Prodrugs, TB Prodrugs and co-formulated liposomes of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers, especially metastatic cancers that express ALK5.

In some embodiments, cancers treatable with liposomes, or TB Prodrugs of the present disclosure include melanoma (e.g., metastatic malignant melanoma), renal cancer (e.g., clear cell carcinoma), prostate cancer (e.g., hormone refractory prostate adenocarcinoma), breast cancer, colon cancer, lung cancer (e.g., non-small cell lung cancer and small cell lung cancer), squamous cell head and neck cancer, urothelial cancer (e.g. bladder) and cancers with high microsatellite instability ($MSI^{high}$). Additionally, the disclosure includes refractory or recurrent malignancies whose growth may be inhibited using the liposomes, or TB Prodrugs or co-formulated liposomes of the disclosure.

In additional embodiments, cancers that are treatable using the formulated and/or co-formulated liposomes or TB Prodrugs of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In further embodiments, cancers that are treatable using the formulated and/or co-formulated liposomes or TB Prodrugs of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In addition, in some embodiments, the formulated and/or co-formulated liposomes, or TB Prodrugs of the present disclosure can be used to treat sickle cell disease and sickle cell anemia.

Furthermore, in some embodiments, diseases and indications that are treatable using the formulated and/or co-formulated liposomes, or TB Prodrugs of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Additionally, TGFβ, ALK5, and/or kinase pathway blockade with formulated and/or co-formulated liposomes, or TB Prodrugs of the present disclosure can also be used for treating infections such as viral, bacteria, fungus, and parasite infections.

The present disclosure provides a method for treating infections such as viral infections. The method includes administering to a patient, a therapeutically effective amount of a formulated and/or co-formulated liposome or TB Prodrugs or any of the formulas as described herein (i.e., TB4-Prodrug) as recited in any of the claims and described herein, a salt thereof.

In one embodiment, the method(s) include administering to the patient a therapeutically effective amount of LNP-TB4 or a salt thereof.

In a further embodiment, the method(s) include administering to the patient a therapeutically effective amount of SLNP-TB4 or a salt thereof.

Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, Ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In addition, the present disclosure provides a method for treating bacterial infections. The method includes administering to a patient, a therapeutically effective amount of a formulated and/or co-formulated liposome or TB Prodrugs, or any of the formulas as described herein (i.e., TB4-Prodrug) as recited in any of the claims and described herein, or a salt thereof.

Examples of pathogenic bacteria causing infections treatable by methods of the disclosure, include but are not limited to, *chlamydia, rickettsia* bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

In addition, the present disclosure provides a method for treating fungus infections. The method includes administering to a patient, a therapeutically effective amount of a formulated and/or co-formulated liposome or TB Prodrugs, or any of the formulas as described herein (i.e., TB4-Prodrug) as recited in any of the claims and described herein, or a salt thereof.

In one embodiment, the method(s) include administering to the patient a therapeutically effective amount of LNP-TB4 or a salt thereof.

In a further embodiment, the method(s) include administering to the patient a therapeutically effective amount of SLNP-TB4 or a salt thereof.

Examples of pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, Niger*, etc.), Genus Mucorales (*Mucor, absidia*, rhizophus), *Sporothrix schenkii, Blastomyces dermatitidis, Paracoccidioides brasiliensis, Coccidioides immitis* and *Histoplasma capsulatum.*

Additionally, the present disclosure provides a method for treating parasite infections. The method includes administering to a patient, a therapeutically effective amount of a formulated and/or co-formulated liposome or TB Prodrugs, or any of the formulas as described herein (i.e., TB4-Prodrug) as recited in any of the claims and described herein, or a salt thereof.

In one embodiment, the method(s) include administering to the patient a therapeutically effective amount of LNP-TB4 or a salt thereof.

In a further embodiment, the method(s) include administering to the patient a therapeutically effective amount of SLNP-TB4 or a salt thereof.

Examples of pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

In a further set of embodiments that are within the scope of this disclosure, the formulated and/or co-formulated nanocarriers, liposomes, SLNPs or TB Prodrugs, or any of the formulas as described herein (i.e. TB4-Prodrug) are useful in preventing or reducing the risk of developing any of the diseases referred to in this disclosure; e.g., preventing or reducing the risk of developing a disease, condition or disorder in an individual who may be predisposed to the disease, condition or disorder but does not yet experience or display the pathology or symptomatology of the disease.

In one embodiment, the method(s) include administering to the patient a therapeutically effective amount of LNP-TB4 or a salt thereof.

In a further embodiment, the method(s) include administering to the patient a therapeutically effective amount of SLNP-TB4 or a salt thereof.

XII.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a formulated and/or co-formulated nanocarrier that is or can be detectably labeled and/or is loaded with an TB prodrug of the disclosure. Kits can comprise a container comprising a drug unit. The kit can include all or part of the formulated and/or co-formulated nanocarriers and/or an TB prodrug.

The kit of the invention will typically comprise the container described above, and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing, or prognosing a condition, such as a cancer or other immunological disorder.

The terms "kit" and "article of manufacture" can be used as synonyms.

In another embodiment of the invention, an article(s) of manufacture containing compositions, such as formulated and/or co-formulated nanocarriers and/or TB Prodrugs are within the scope of this disclosure. The article of manufacture typically comprises at least one container and at least one label. Suitable containers include, for example, bottles, vials, syringes, and test tubes. The containers can be formed from a variety of materials such as glass, metal, or plastic. The container can hold formulated and/or co-formulated nanocarriers loaded with TB Prodrugs.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be formulated and/or co-formulated nanocarriers loaded with TB Prodrugs and/or TB Prodrugs as disclosed herein.

The article of manufacture can further comprise a second container comprising a pharmaceutically acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

In one embodiment, the kit or article of manufacture comprises LNP-TB4 and/or a therapeutically effective amount of LNP-TB4.

In one embodiment, the kit or article of manufacture comprises SLNP-TB4 and/or a therapeutically effective amount of SLNP-TB4.

Exemplary Embodiments

Among the provided embodiments are:

1) A TB prodrug composition comprising,
   (i) a drug moiety;
   (ii) a lipid moiety; and
   (iii) a linkage unit ("LU"),
   whereby the drug moiety comprises a TGFβ antagonist and whereby the LU conjugates the drug moiety with the lipid moiety.
2) The TB prodrug of claim 1, further comprising the chemical structure set forth in FORMULA I.
3) The TB prodrug of claim 1, further comprising the chemical structure set forth in FORMULA II.
4) The TB prodrug of claim 1, further comprising the chemical structure set forth in FORMULA III.
5) The TB prodrug of claim 1, wherein the drug moiety comprises the chemical structure set forth as TB4.
6) The TB prodrug of claim 1, wherein the LU is a hydromethylcarbamate linker.
7) The TB prodrug of claim 1, wherein the lipid moiety comprises a lipid set forth in Table I.
8) The TB prodrug of claim 1, wherein the lipid moiety comprises a lipid set forth in Table III.
9) The TB prodrug of claim 1, wherein the lipid moiety comprises CHEMS.
10) The TB prodrug of claim 1, wherein the lipid moiety comprises Stearic Acid.
11) The TB prodrug of claim 1, wherein the drug moiety comprises the chemical structure set forth as TB4 and wherein the lipid moiety comprises Stearic acid and wherein the compound has the following chemical structure:

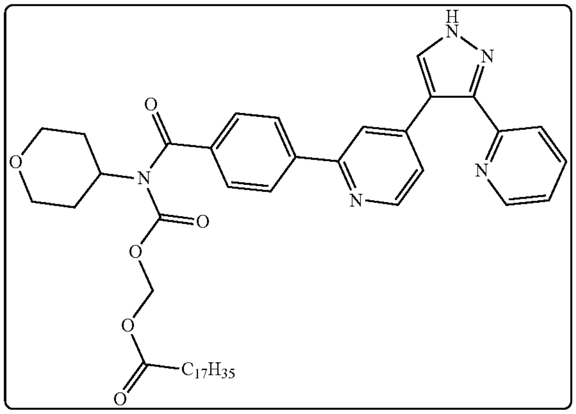

12) A TB prodrug composition comprising,
   (i) a drug moiety, whereby the drug moiety comprises TB4;
   (ii) a lipid moiety, whereby the lipid moiety comprises CHEMS; and
   (iii) LU, whereby the LU comprises a hydromethylcarbamate linker.
13) A TB prodrug composition comprising,
   (i) a drug moiety, whereby the drug moiety comprises TB4;
   (ii) a lipid moiety, whereby the lipid moiety comprises Stearic Acid; and
   (iii) a LU, whereby the LU comprises a hydromethylcarbamate linker.
14) A TB prodrug composition of claim 13, having the following chemical structure:

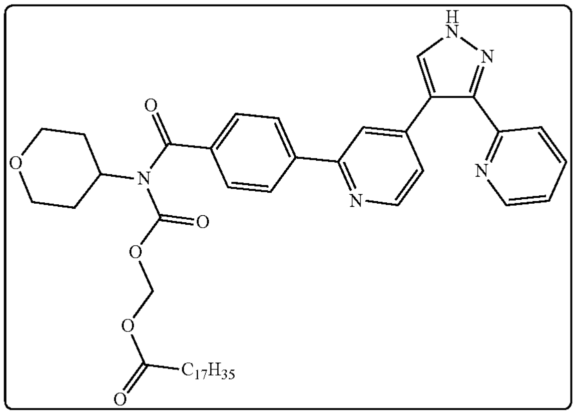

15) A nanocarrier comprising, a TB prodrug whereby the nanocarrier releases an active ALK5 inhibitor after cleavage of a LU.

16) The nanocarrier of claim 15, wherein the LU is a hydromethylcarbamate linker.

17) The nanocarrier of claim 15, further comprising a helper lipid, whereby the helper lipid is set forth in Table II.

18) The nanocarrier of claim 15, wherein the TB prodrug comprises TB4.

19) The nanocarrier of claim 15, wherein the nanocarrier is a liposome.

20) The liposome of claim 19, wherein the TB prodrug comprises TB4 and is denoted LNP-TB4.

21) The liposome of claim 19, whereby the liposome is further co-formulated with one or more immune modulating agent or a lipid-prodrug thereof, wherein the immune modulating agent is selected from the group consisting of immunogenic-cell death inducing chemotherapeutics, toll-receptor agonists, STING agonists, CTLA-4 inhibitors, IDO inhibitors, PD-1/PD-L1 inhibitors, CD1D agonists and/or prodrugs thereof.

22) The liposome of claim 19, whereby the liposome is further co-formulated with an ICD-inducing chemotherapeutic, wherein the ICD-inducing chemotherapeutic is selected from the group consisting of DOX, MTO, OXA, CP, Bortezomib, Carfilzomib, or Paclitaxel.

23) The liposome of claim 19, further comprising DOX.

24) The liposome of claim 19, further comprising MTO.

25) The liposome of claim 22, further comprising DOX.

26) The liposome of claim 22, further comprising MTO.

27) The liposome of claim 19, whereby the liposome is further co-formulated with a toll-receptor agonist or a lipid-prodrug thereof, wherein the toll-receptor agonist is selected from the group consisting of Resiquimod (R848), Gardiquimod, 852A, DSR 6434, Telratolimod, CU-T12-9, monophosphoryl Lipid A (MPLA), 3D(6-acyl)-PHAD®, SMU127, Pam3CSK4, or 3D-PHAD®.

28) The liposome of claim 19, whereby the liposome is further co-formulated with a PD-1/PD-L1 antagonist or a lipid-prodrug thereof, wherein the PD-1/PD-L1 antagonist is selected from the group consisting of AUNP12, CA-170, or BMS-986189.

29) A kit comprising a liposome of any one of claims 15-28.

30) The nanocarrier of claim 15, wherein the nanocarrier is a solid-lipid nanoparticle (SLNP).

31) The SLNP of claim 30, wherein the TB prodrug comprises TB4 and is denoted SLNP-TB4.

32) The SLNP of claim 30, whereby the SLNP is further co-formulated with one or more immune modulating agent or a lipid-prodrug thereof, wherein the immune modulating agent is selected from the group consisting of immunogenic-cell death inducing chemotherapeutics, toll-receptor agonists, STING agonists, CTLA-4 inhibitors, IDO inhibitors, PD-1/PD-L1 inhibitors, CD1D agonists and/or prodrugs thereof.

33) The SLNP of claim 30, whereby the SLNP is further co-formulated with an ICD-inducing chemotherapeutic, wherein the ICD-inducing chemotherapeutic is selected from the group consisting of DOX, MTO, OXA, CP, Bortezomib, Carfilzomib, or Paclitaxel.

34) The SLNP of claim 30, further comprising DOX.

35) The SLNP of claim 30, further comprising MTO.

36) The SLNP of claim 33, further comprising DOX.

37) The SLNP of claim 33, further comprising MTO.

38) The SLNP of claim 30, whereby the liposome is further co-formulated with a toll-receptor agonist or a lipid-prodrug thereof, wherein the toll-receptor agonist is selected from the group consisting of Resiquimod (R848), Gardiquimod, 852A, DSR 6434, Telratolimod, CU-T12-9, monophosphoryl Lipid A (MPLA), 3D(6-acyl)-PHAD®, SMU127, Pam3CSK4, or 3D-PHAD®.

39) The SLNP of claim 30, whereby the liposome is further co-formulated with a PD-1/PD-L1 antagonist or a lipid-prodrug thereof, wherein the PD-1/PD-L1 antagonist is selected from the group consisting of AUNP12, CA-170, or BMS-986189.

40) A kit comprising a SLNP of any one of claims 30-39.

41) A method of treating a subject suffering or diagnosed with cancer comprising, (i) administering to a subject in need of such treatment an effective amount of a nanocarrier, wherein the nanocarrier comprises a TB prodrug; and (ii) a pharmaceutically acceptable salt thereof.

42) The method of claim 41, wherein the TB prodrug comprises a TB4-Prodrug.

43) The method of claim 41, wherein the nanocarrier comprises a TB4-Prodrug further co-formulated with and ICD-inducing chemotherapeutic.

44) The method of claim 41, wherein the nanocarrier comprises a TB4-Prodrug further co-formulated with an immune modulating agent.

45) The method of claim 41, wherein the nanocarrier is a liposome.

46) The method of claim 45, wherein the liposome is LNP-TB4.

47) The method of claim 41, wherein the nanocarrier is a solid-lipid nanoparticle.

48) The method of claim 47, wherein the liposome is SLNP-TB4.

49) A method of treating a subject suffering or diagnosed with cancer comprising, (iii) administering to a subject in need of such treatment an effective amount of a nanocarrier, wherein the nanocarrier comprises a TB prodrug; and (iv) a pharmaceutically acceptable salt thereof.

50) The method of claim 49, wherein the TB prodrug comprises a TB4-Prodrug.

51) The method of claim 49, wherein the nanocarrier comprises a TB4-Prodrug further co-formulated with and ICD-inducing chemotherapeutic.

52) The method of claim 49, wherein the nanocarrier comprises a TB4-Prodrug further co-formulated with an immune modulating agent.

53) The method of claim 49, wherein the nanocarrier is a solid-lipid nanoparticle ("SLNP").

54) The methods of claim 53, wherein the SLNP is SLNP-TB4.

55) The method of claim 49, wherein the nanocarrier is a liposome.

56) The method of claim 55, wherein the liposome is LNP-TB4.

57) A TB4 Prodrug having the following chemical structure:

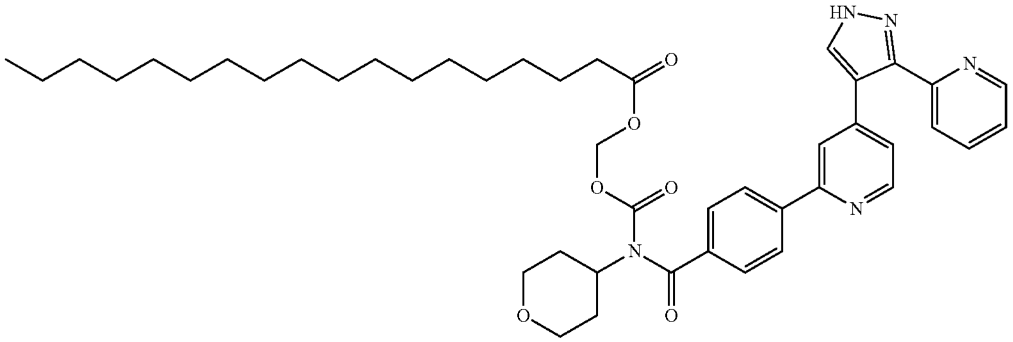 [SMILES: CCCCCCCCCCCCCCCCCC(=O)OCOC(=O)N(C(=O)c1ccc(-c2cc(-c3c[nH]nc3-c3ccccn3)ccn2)cc1)C1CCOCC1]

58) A liposome comprising the TB4 Prodrug of claim 57.

59) A liposome comprising the TB4 Prodrug of claim 57, further comprising a helper lipid.

60) A liposome of claim 59, wherein the helper lipid is set forth in Table II.

61) A solid-lipid nanoparticle (SLNP) comprising the TB4 Prodrug of claim 57.

62) A TB4 Prodrug having the following chemical structure:

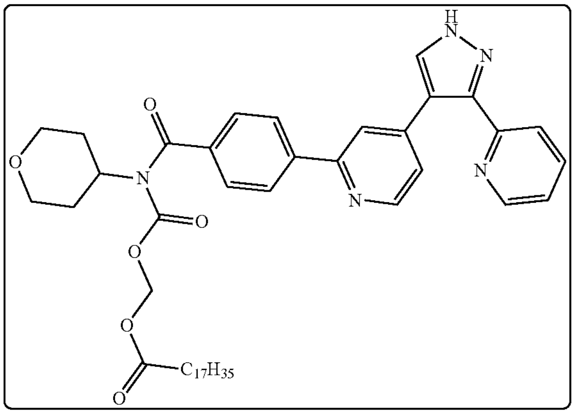

63) A liposome comprising the TB4 Prodrug of claim 62.

64) A liposome comprising the TB4 Prodrug of claim 62, further comprising a helper lipid.

65) A liposome of claim 64, wherein the helper lipid is set forth in Table II.

66) A liposome of claim 62, denoted LNP-TB4.

67) A solid lipid nanoparticle (SLNP) comprising the TB4-Prodrug of claim 62.

68) The SLNP of claim 67, denoted SLNP-TB4.

69) The liposome of claim 63 co-formulated with AR5.

70) The liposome of claim 63 co-formulated with TR6.

71) The liposome of claim 63 co-formulated with 103.

72) The liposome of claim 63 co-formulated with PD3.

73) The liposome of claim 63 co-formulated with MTO.

74) The liposome of claim 63 co-formulated with MTO and 103.

75) The liposome of claim 63 co-formulated with MTO and AR5.

76) The SLNP of claim 68 co-formulated with MTO.

77) The SLNP of claim 68 co-formulated with AR5.

78) The SLNP of claim 68 co-formulated with 103.

79) The SLNP of claim 68 co-formulated with PD3.

80) The SLNP of claim 68 co-formulated with MTO and 103.

81) The SLNP of claim 68 co-formulated with MTO and AR5.

EXAMPLES

Various aspects of the invention are further described and illustrated by way of the several examples that follow, none of which is intended to limit the scope of the invention.

Example 1: Chemical Synthesis of TB4 Prodrug Comprising Stearic Acid

Chemical synthesis of a TB4 prodrug comprising Stearic Acid is synthesized using the following protocol. First, Compound (1) is treated with Compound (2) and KHMDS to yield Intermediate 3. Then, Intermediate 3 is treated successively with DMF dimethyl acetal, then hydrazine hydrate to yield Intermediate 4. Then, Intermediate 4 is treated with trityl chloride to yield Intermediate 5. Next, Intermediate 5 is treated with Reagent (6) and palladiumtriphenylphosphine followed by hydrolysis with sodium hydroxide to yield Intermediate 7. Then, Intermediate 7 is treated with Reagent (8) and EDCl/HOBt to yield Intermediate 9. Then, Intermediate 9 is treated with lithiumhexamethyldisilazide followed by chloromethyl chloroformate (10) to yield Intermediate 11. Finally, Intermediate 11 in DMF is treated successively with stearic acid, then silver carbonate, then sodium iodide at 80° C., then HCl in methanol to yield final prodrug TB4 comprising Stearic Acid. (12). (FIG. 1). The synthesis set forth in this example yields a TB4-Prodrug with the following chemical structure:

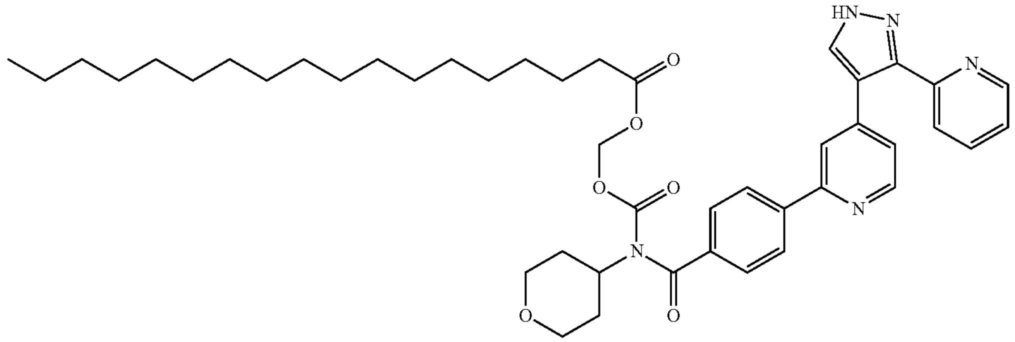

Example 2: Chemical Synthesis for Protective Group Intermediates En Route to TB4 Prodrug To synthesize the protective group intermediate, the following protocol was used. Briefly, to a solution of TB4 (13.0 g, 30.5 mmol, 1.00 eq) in DCM (1.50 L) was added $Boc_2O$ (8.00 g, 36.7 mmol, 8.42 mL, 1.20 eq) and DMAP (746 mg, 6.11 mmol, 0.20 eq) at 15° C. After addition, the reaction mixture was stirred at 30° C. for 12 hrs. TLC (Dichloromethane:Methanol=10:1) showed that TB4 ($R_f$=0.2) was consumed and one major new spot ($R_f$=0.5) was formed. LCMS confirmed that the desired mass (RT=0.850 min) was detected. The reaction mixture was concentrated under reduced pressure to give the crude product. The crude product was purified by column chromatography ($SiO_2$, Dichloromethane:Methanol=50:1-30:1, $R_f$=0.5) to afford Compound 2 (13.0 g, 24.7 mmol, 80.9% yield) as a white solid. The resulting compound is set forth in FIG. 2.

Example 3: Chemical Synthesis for Protective Group Intermediates En Route to TB4 Prodrug In another embodiment, a further protective group intermediate was synthesized in the following manner. Briefly, to a solution of Compound 3 (4.50 g, 7.28 mmol, 1.00 eq) in DCM (225 mL) was added TFA (16.6 g, 145 mmol, 10.8 mL, 20.0 eq) at 25° C. After addition, the reaction mixture was stirred at 25° C. for another 4 hrs. LCMS confirmed that the reaction was completed and the desired mass (RT=0.874 min) was detected. The reaction mixture was adjusted to pH=7-8 with saturated $NaHCO_3$ solution and extracted with DCM (150 mL*2). The combined organic layer was washed with brine (150 mL), dried over $Na_2SO_4$, filtered, and concentrated to give Compound 4 (3.50 g, 6.76 mmol, 92.81% yield) as a yellow solid. The resulting compound is set forth in FIG. 3.

Example 4: Chemical Synthesis of TB4 Prodrug Comprising Stearic Acid

Chemical synthesis of a TB4-Prodrug comprising Stearic Acid is synthesized using the following protocol. First, to a solution of TB4 (13.0 g, 30.5 mmol, 1.00 eq) in DCM (1.50 L) was added $Boc_2O$ (8.00 g, 36.7 mmol, 8.42 mL, 1.20 eq) and DMAP (746 mg, 6.11 mmol, 0.20 eq) at 15° C. After addition, the reaction mixture was stirred at 30° C. for 12 hrs. TLC (Dichloromethane:Methanol=10:1) showed that TB4 ($R_f$=0.2) was consumed and one major new spot ($R_f$=0.5) was formed. LCMS showed that the desired mass (RT=0.850 min) was detected. The reaction mixture was concentrated under reduced pressure to give the crude product. The crude product was purified by column chromatography ($SiO_2$, Dichloromethane:Methanol=50:1-30:1, $R_f$=0.5) to afford Compound 2 (13.0 g, 24.7 mmol, 80.9% yield) as a white solid. Then, to a solution of Compound 2 (9.00 g, 17.1 mmol, 1.00 eq) in DCM (1000 mL) was added LiHMDS (1 M, 37.6 mL, 2.20 eq) at −70° C. under $N_2$ for 1 hr. The mixture was added Compound 2a (9.36 g, 72.5 mmol, 6.45 mL, 4.24 eq) in DCM (50 mL) at −70° C. The mixture was stirred at −70° C. for 6 hrs. Then the mixture was stirred at 15° C. for another 6 hrs. LCMS showed that 18.4% of Compound 2 (RT=1.038 mins) was remained and 33.1% desired mass (RT=1.195 mins) was detected. The mixture was poured into saturated $NH_4Cl$ solution (500 mL) and was extracted with DCM (200 mL*2). The combined organic layers were washed with brine (500 mL), dried over $Na_2SO_4$ and concentrated and confirmed by LCMS. The crude product was purified by reverse-MPLC (ACN/$H_2O$, TFA condition) and after removing the ACN and the water phase was extracted with ethyl acetate (300 mL*3). The combined organic layers were washed with brine (200 mL), dried over $Na_2SO_4$, and concentrated under reduced pressure to give Compound 3 (6.20 g, 10.0 mmol, 29.2% yield) as a yellow solid, which was confirmed by LCMS. Then, to a solution of Compound 3 (4.50 g, 7.28 mmol, 1.00 eq) in DCM (225 mL) was added TFA (16.6 g, 145 mmol, 10.8 mL, 20.0 eq) at 25° C. After addition, the reaction mixture was stirred at 25° C. for another 4 hrs. LCMS showed that the reaction was completed and the desired mass (RT=0.874 min) was detected. The reaction mixture was adjusted to pH=7-8 with saturated $NaHCO_3$ solution and extracted with DCM (150 mL*2). The combined organic layer was washed with brine (150 mL), dried over $Na_2SO_4$, filtered, and concentrated to give Compound 4 (3.50 g, 6.76 mmol, 92.81% yield) as a yellow solid, which was used for next step directly without further purification. Finally, to a solution of Compound 4 (3.50 g, 6.76 mmol, 1.00 eq) and stearic acid (2.88 g, 10.1 mmol, 3.41 mL, 1.50 eq) in ACN (175 mL) was added DIEA (2.62 g, 20.3 mmol, 3.53 mL, 3.00 eq). After addition, the reaction mixture was stirred at 80° C. for another 36 hrs. LCMS showed that Compound 4 was completed incompletely, and the desired mass (RT=1.383 min) was detected. The mixture was concentrated under reduced pressure at 45° C. to give the crude product that was confirmed by LCMS. The crude product was combined with ET34822-17 to purify by reverse-MPLC (MeOH/$H_2O$/TFA condition) and then concentrated to give the crude product. The crude product was purified by column chromatography ($SiO_2$, Petroleum ether:Ethyl acetate=1:1 to Ethyl acetate: Methanol=10:1), which was detected by TLC (Ethyl acetate: Methanol=10:1, $R_f$=TB4 comprising Stearic acid (1.3 g, 1.59 mmol, 21.2% yield, 93.9% purity) was obtained as a yellow gum, which was confirmed by $^1$H NMR, FNMR, LCMS, and HPLC. The resulting compound and synthesis is set forth in FIG. 7. The synthesis set forth in this example yields a TB4-Prodrug with the following chemical structure:

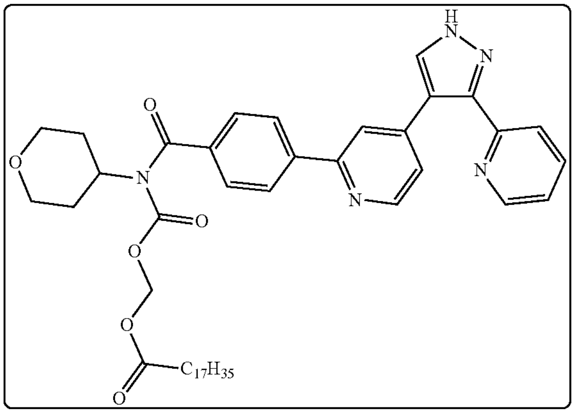

Example 5: Synthesis and Characterization of LNP-TB4 Liposome

In another experiment, a liposome comprising the TB4 prodrug (denoted LNP-TB4) was synthesized in the following manner. Briefly, In the first step, a lipid stock solution of POPC (1-palmitoyl-2-oleoyl-glycero-3-phosphocholine), CHOL, and DSPE-PEG, was prepared in ethanol (20 mg/ml) separately. TB4 prodrug (TB4+Stearic Acid) stock solution was prepared in acetonitrile (20 mg/ml) as it was not soluble in ethanol. The of lipid mixture of POPC, CHOL, TB4+ Stearic Acid and DSPE-PEG was mixed together at a molar ratio of 51:29:16.5:3.5, and subsequently diluted with ethanol to get a total lipid concentration of 10 mg/ml. This lipid mixture was heated at 55-60 degree Centigrade using the heating block attachment in the microfluidizer. Similarly, the aqueous phase containing 1 mM PBS buffer was also preheated at 55-60 degree centigrade before passing through the microfluidics cartridge at the flow rate of 5:1 (aqueous: organic phase, lipid mixture). The solvent was removed using dialysis membrane of cut off 12 KDa size (Sigma Aldrich) against DI water for at least 24 hrs. The Dialysis water was changed at least 5 times during the period of 24 hrs. to maximize the removal of the solvent. After the removal of the solvent, the LNP-TB4 was concentrated according to the need using Amicon centrifugal filtration device (cut off size 10 KDa, at 3000 g).

Characterization of the LNP-TB4 liposome was determined using a Malvern Zetasizer (Malvern Instrumentation Co., Westborough, MA, USA). Briefly, two (2) ml of LNP-TB4 liposomes (concentration of the liposome was of 0.5-1 mg/ml) was placed in a 4-sided, clear, plastic cuvette and analyzed directly at 25° C. The results shown in FIG. 8 show the Zav size of the nanoparticles were approximately 87 nm with a PDI of approximately 0.265.

Additionally, Zeta potential of the LNP-TB4 liposomes in aqueous dispersion was determined using a Malvern zeta seizer Instrument (Malvern Instrumentation Co, Westborough, MA, USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results slim the Zeta potential determination of LNP-TB4 was approximately −15.1 mV (FIG. 9).

Example 6: Synthesis and Characterization of LNP-TB4-ID3 Liposome

In another experiment, a liposome comprising the TB4 prodrug (denoted LNP-TB4) was co-formulated with ID3 and synthesized in the following manner. Briefly, in the first step, a lipid stock solution of POPC (1-palmitoyl-2-oleoyl-glycero-3-phosphocholine), CHOL, and DSPE-PEG, was prepared in ethanol (20 mg/ml) separately. Then a stock solution of TB4 prodrug (TB4+Stearic Acid) and ID3 prodrug was prepared in acetonitrile (20 mg/ml) as it was not soluble in ethanol. Then the lipid mixture of POPC, CHOL, TB4+Stearic Acid, ID3, and DSPE-PEG was mixed together at a molar ratio of 53:31:6:6:4, and subsequently diluted with ethanol to get a total lipid concentration of 10 mg/ml. This lipid mixture was heated at 50 degree Centigrade using the heating block attachment in the microfluidizer. Similarly, the aqueous phase containing 1 mM PBS buffer was also preheated at 50 degree centigrade before passing through the microfluidics cartridge at the flow rate of 4.5:1 (aqueous: organic phase, lipid mixture). The solvent was removed using dialysis membrane of cut off 12 KDa size (Sigma Aldrich) against DI water for at least 24 hrs. The Dialysis water was changed at least 5 times during the period of 24 hrs. to maximize the removal of the solvent. After the removal of the solvent, the LNP-TB4-ID3 was concentrated according to the need using Amicon centrifugal filtration device (cut off size 10 KDa, at 3000 g).

Characterization of the LNP-TB4-ID3 liposome was determined using a Malvern Zetasizer (Malvern Instrumentation Co., Westborough, MA, USA). Briefly, two (2) ml of LNP-TB4-ID3 liposomes (concentration of the liposome was of 0.5-1 mg/ml) was placed in a 4-sided, clear, plastic cuvette and analyzed directly at 25° C. The results shown in FIG. 10 show the Zav size of the nanoparticles were approximately 87 nm with a PDI of approximately 0.075.

Additionally, Zeta potential of the LNP-TB4-ID3 liposome in aqueous dispersion was determined using a Malvern zeta seizer Instrument (Malvern Instrumentation Co, Westborough, MA, USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-TB4-ID3 was approximately −11.5 mV (FIG. 11).

Additionally, a summary table of additional co-formulated LNP-TB4 is set forth Table IV.

Example 7: Synthesis and Characterization of SLNP-TB4 Solid-Lipid Nanoparticle

In another experiment, a solid-lipid nanoparticle (SLNP) comprising the TB4 prodrug (denoted SLNP-TB4) was synthesized in the following manner. Briefly, SLNPs comprising the TB4 prodrug were prepared using different types of emulsifier(s) such as Moliwol 488 (Polyvinyl alcohol), Pluronic F 127, and Kolliphor RH 40. In the first step, a lipid stock solution of POPC, CHOL, DSPE-PEG, was prepared in ethanol (20 mg/mi). Then, a TB4 prodrug stock solution was prepared in acetonitrile (20 mg/ml). The of lipid mixture of POPC, CHOL, TB4 and DSPE-PEG at a molar ratio of 51:29:15:5 was mixed together and then was diluted with ethanol to get a lipid concentration of 10 mg/ml. This lipid mixture was heated at 55 degree Centigrade using the heating block attachment in the microfluidizer. Similarly, the aqueous phase containing 2% w/v Moliwol 488 (or 2% w/v Pluronic F127/Kolliphor RH 40) solution was also pre-heated at 55 degree centigrade before passing through the microfluidics cartridge at the flow rate of 5:1 (aqueous: organic phase, lipid mixture). The solvent was removed using dialysis membrane of cut off 12 KDa size (Sigma Aldrich) against DI water for at least 24 hrs. The Dialysis water was changed at least 5 times during the period of 24 hrs. to maximize the removal of the solvent. After the removal of the solvent, SLNPs were passed through a 0.2-micron filter membrane (cellulose acetate). The SLNP-TB4 was concentrated according to the need using Amicon centrifugal filtration device (cut off size 10 KDa, at 3000 g).

Characterization of the SLNP-TB4 was determined using a Malvern Zetasizer (Malvern Instrumentation Co., Westborough, MA, USA). Briefly, two (2) ml of SLNP-TB4 (concentration of the SLNP was of 0.5-1 mg/ml) was placed in a 4-sided, clear, plastic cuvette and analyzed directly at 25° C. The results shown in FIG. 12 show the Zav size of the nanoparticles were approximately 90 nm with a PDI of approximately 0.074.

Additionally, Zeta potential of the SLNP-TB4 solid-lipid nanoparticle in aqueous dispersion was determined using a Malvern zeta seizer Instrument (Malvern Instrumentation Co, Westborough, MA, USA). Briefly, approximately one (1) ml of the SLNP (concentration approximately 2 mg/ml in 20 mM NaCl) was placed in a disposable capillary zeta potential cell available for the Zetasizer. The measurement was done at 25° C. The results show the Zeta potential determination of SLNP-TB4 was approximately −11.9 mV (FIG. 13).

Example 8: Synthesis and Characterization of SLNP-TB4-ID3 Solid-Lipid Nanoparticle In another experiment, a solid-lipid nanoparticle (SLNP) comprising the TB4 prodrug co-formulated with 1D3 (denoted SLNP-TB4-ID3) was synthesized in the following manner. Briefly, SLNPs comprising the TB4 prodrug were prepared using different types of emulsifier(s) such as Moliwol 488 (Polyvinyl alcohol), Pluronic F 127, and Kolliphor RH 40. In the first step, a lipid stock solution of POPC, CHOL, DSPE-PEG, was prepared in ethanol (20 mg/ml). Then, a TB4 and 103 prodrug stock solution was prepared in acetonitrile (20 mg/ml). The of lipid mixture of POPC, CHOL, TB4, 103, and DSPE-PEG at a molar ratio of 52:29:7:7:5 was mixed together and then was diluted with ethanol to get a lipid concentration of 10 mg/ml. This lipid mixture was heated at 55 degree Centigrade using the heating block attachment in the microfluidizer. Similarly, the aqueous phase containing 2% w/v Moliwol 488 (or 2% w/v Pluronic F127/Kolliphor RH 40) solution was also pre-heated at 55 degree centigrade before passing through the microfluidics cartridge at the flow rate of 5:1 (aqueous: organic phase, lipid mixture). The solvent was removed using dialysis membrane of cut off 12 KDa size (Sigma Aldrich) against DI water for at least 24 hrs. The Dialysis water was changed at least 5 times during the period of 24 hrs. to maximize the removal of the solvent. After the removal of the solvent, SLNPs were passed through a 0.2-micron filter membrane (cellulose acetate). The SLNP-TB4-ID3 was concentrated according to the need using Amicon centrifugal filtration device (cut off size 10 KDa, at 3000 g).

Characterization of the SLNP-TB4-ID3 was determined using a Malvern Zetasizer (Malvern Instrumentation Co., Westborough, MA, USA). Briefly, two (2) ml of SLNP-TB4-103 (concentration of the SLNP was of 0.5-1 mg/ml) was placed in a 4-sided, clear, plastic cuvette and analyzed directly at 25° C. The results shown in FIG. 14 show the Zav size of the nanoparticles were approximately 104.3 nm with a PDI of approximately 0.119.

Additionally, Zeta potential of the SLNP-TB4-ID3 solid-lipid nanoparticle in aqueous dispersion was determined using a Malvern zeta seizer Instrument (Malvern Instrumentation Co, Westborough, MA, USA). Briefly, approximately one (1) ml of the SLNP (concentration approximately 2 mg/ml in NaCl) was placed in a disposable capillary zeta potential cell available for the Zetasizer. The measurement was done at 25° C. The results show the Zeta potential determination of SLNP-TB4-ID3 was approximately −10.3 mV (FIG. 15).

Additionally, a summary table of additional co-formulated SLNP-TB4 is set forth Table V.

Example 9: Tumor Inhibition of SLNP-TB4 Using B16F10 Cells In Vivo

In this experiment, evaluation of SLNP-TB4 was performed using the following protocols. Murine melanoma cancer B16F10 cells (cells ($0.2\times10^6$)) were inoculated subcutaneously in the right rear flank region of C57BL/6 mice. Animals were treated with vehicle control, LNP-MTO (Mitoxantrone dihydrochloride in liposome form) at 3 mg/kg, LNP-AR5 (AR5-Stearic Acid in liposome form) at 3 mg/kg, combination of LNP-AR5 and LNP-TB4 (TB4-Stearic acid in liposome form) at 3 mg/kg and combination of LNP-MTO and SLNP-TB4 (TB4-stearic acid in solid lipid nanoparticle) at 3 mg/kg two times weekly through iv injection. Tumor volumes were measured three (3) times in two dimensions using a caliper, and the volume was calculated using the formula: $V=(L\times W\times W)\times 0.5$, where V is tumor volume, L is tumor length (the longest tumor dimension), and W is tumor width (the longest tumor dimension perpendicular to L). The tumor growth inhibition (TGI) was calculated based on the tumor size data of day 15.

The results show that the combination of SLNP-TB4 in combination with LNP-MTO provided significant anti-tumor activities. The TGI was calculated at 44.12% (all $p<0.05$). (FIG. 16).

Example 10: Tumor Inhibition of LNP-TB4 in Multiple Combination(s) Using B16F10 Cells In Vivo In this experiment, evaluation of LNP-TB4 was performed using the following protocols. Murine melanoma cancer B16F10 cells (cells ($0.2\times10^6$)) were inoculated subcutaneously in the right rear flank region of C57BL/6 mice. Animals were treated with vehicle control, LNP-MTO (Mitoxantrone dihydrochloride in liposome form) at 3 mg/kg, combination of LNP-TB4 (TB4-Stearic acid in liposome form) and LNP-TR6 (TR6-Chemes in liposome form) at 3 mg/kg, a further combination LNP-TB4 and LNP-AR5 (AR5-Stearic Acid in liposome form) at 3 mg/kg, and a further combination of LNP-TB4 and LNP-ID3 (ID3-Stearic acid in liposome form) at 3 mg/kg, and a further combination of LNP-TB4 and LNP-PD3 (PD3-Cholesterol at 3 mg/kg, a further combination of LNP-TB4, LNP-MTO and LNP-ID3 at 3 mg/kg and a further combination of LNP-TB4, LNP-MTO, and LNP-AR5 at 3 mg/kg two times weekly through iv injection. Tumor volumes were measured three (3) times in two dimensions using a caliper, and the volume was calculated using the formula: $V=(L\times W\times W)\times 0.5$, where V is tumor volume, L is tumor length (the longest tumor dimension), and W is tumor width (the longest tumor dimension perpendicular to L). The tumor growth inhibition (TGI) was calculated based on the tumor size data of day 16.

The results show that treatment of LNP-MTO as a single agent at 3 mg/kg produced anti-tumor activity. The TGI was calculated at 32.6% ($p<0.05$). In addition, the combination of LNP-TB4+LNP-MTO+LNP-ID3 and LNP-AR5+LNP-MTO+LNP-TB4 produced anti-tumor activity. The TGI was calculated at 32.86% ($p<0.05$) and 37.86% ($p<0.05$) respectively. (FIG. 17).

Example 11: Validation of LNP-TB4 and SLNP-TB4 Mechanism of Action In Vitro

In this experiment, evaluation of the LNP-TB4 and SLNP-TB4 mechanism of action was performed in vitro using the following protocols. The following assay was performed to confirm that TB4 in liposome form (LNP) and TB4 in solid-lipid nanoparticle form (SLNP) can have biological effects in-vitro. Briefly, HEK-Blue™ TGF-β cells and QUANTI-Blue™ (InvivoGen, San Diego, CA) assay were used using standard methods. Stimulation of HEK-Blue™ TGF-β cells with TGF-β induces the activation of the TGF-β/Smad signaling pathway leading to the formation of a Smad3/Smad4 complex. The heterocomplex enters the nucleus and binds SBE sites inducing the production of SEAP. The quantity of SEAP secreted in the supernatant can be readily assessed using QUANTI-Blue. Cells were incubated with TB4, LNP-TB4 and SLNP-TB4 at different concentration in presence of TGF-β at 10 ng/ml. After a twenty-four (24) hour incubation with the respective compounds, the percent (%) of TGF-β inhibition was assessed by measuring the levels of SEAP optimal density (OD) using QUANTI-Blue™ assay and normalizing the data to the control group (cells treated only with TGF-β).

The results showed that treating the cells with LNP-TB4 and SLNP-TB4 causes inhibition of TGF-β. (See, FIG. 18).

Example 12: Human Clinical Trials for the Treatment of Human Carcinomas Through the Use of Formulated and/or Co-Formulated Liposomes Comprising TB Prodrugs Formulated and/or co-formulated liposomes containing TB Prodrugs are used in accordance with the present invention which specifically accumulate in a tumor cell and are used in the treatment of certain tumors and other immunological disorders and/or other diseases. In connection with each of these indications, two clinical approaches are successfully pursued.

I.) Adjunctive therapy: In adjunctive therapy, patients are treated with formulated and/or co-formulated liposomes containing TB Prodrugs in combination with a chemotherapeutic or pharmaceutical or biopharmaceutical agent or a combination thereof. Primary cancer targets are treated under standard protocols by the addition of formulated and/or co-formulated liposomes containing TB Prodrugs. Protocol designs address effectiveness as assessed by the following examples, including but not limited to, reduction in tumor mass of primary or metastatic lesions, increased progression free survival, overall survival, improvement of patient's health, disease stabilization, as well as the ability to reduce usual doses of standard chemotherapy and other biologic agents. These dosage reductions allow additional and/or prolonged therapy by reducing dose-related toxicity of the chemotherapeutic or biologic agent.

II.) Monotherapy: In connection with the use of the formulated and/or co-formulated liposomes containing TB Prodrugs in monotherapy of tumors, the formulated and/or co-formulated liposomes containing TB Prodrugs are administered to patients without a chemotherapeutic or pharmaceutical or biological agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patient's health, disease stabilization, as well as the ability to reduce usual doses of standard chemotherapy and other biologic agents.

Dosage

Dosage regimens may be adjusted to provide the optimum desired response. For example, a single formulated and/or co-formulated liposome containing TB Prodrugs may be administered, several divided doses may be administered over time or the dose may be proportionally reduced or increased as indicated by the exigencies of the therapeutic situation. "Dosage Unit Form" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention is dictated by and directly dependent on (a) the unique characteristics of the formulated and/or co-formulated liposomes containing TB Prodrugs, (b) the individual mechanics of the combination compound, if any, (c) the particular therapeutic or prophylactic effect to be achieved, and (d) the limitations inherent in the art of compounding such a compound for the treatment of sensitivity in individuals.

Clinical Development Plan (CDP)

The CDP follows and develops treatments of using formulated and/or co-formulated liposomes containing TB Prodrugs in connection with adjunctive therapy or monotherapy. Trials initially demonstrate safety and thereafter confirm efficacy in repeat doses. Trials are open label comparing standard chemotherapy and/or the current standard of therapy plus formulated and/or co-formulated liposomes containing TB Prodrugs. As will be appreciated, one non-limiting criteria that can be utilized in connection with enrollment of patients is expression of TGFβ in a tumor as determined by standard detection methods known in the art.

It is believed that formulated and/or co-formulated liposomes, or any of the embodiments disclosed herein, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The present invention is not to be limited in scope by the embodiments disclosed herein, which are intended as single illustrations of individual aspects of the invention, and any that are functionally equivalent are within the scope of the invention. Various modifications to the models, methods, and life cycle methodology of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Examples of Lipids.

| No. | Abbreviation | Name/Chemical Formula |
|---|---|---|
| 1 | CHOL | Cholesterol |
| 2 | DPPG•Na | 1,2-dipalmitoyl-sn-glycero-3-phospho-(1'-rac-glycerol) (sodium salt) |
| 3 | DMPG•Na | 1,2-dimyristoyl-sn-glycero-3-phospho-(1'-rac-glycerol) (sodium salt) |
| 4 | Lyso PC | 1-decanoyl-2-hydroxy-sn-glycero-3-phosphocholine |
| 5 | (Δ9-Cis) PG | 1,2-dioleoyl-sn-glycero-3-phospho-(1'-rac-glycerol) (sodium salt) |
| 6 | Soy Lyso PC | L-α-lysophosphatidylcholine (Soy) |
| 7 | PG | 1,2-dilauroyl-sn-glycero-3-phospho-(1'-rac-glycerol) (sodium salt) |
| 8 | PA-PEG3-mannose | 1,2-dipalmitoyl-sn-glycero-3-phospho((ethyl-1',2',3'-triazole)triethyleneglycolmannose) (ammonium salt) |
| 9 | C16 PEG2000 Ceramide | N-palmitoyl-sphingosine-1-{succinyl[methoxy(polyethylene glycol)2000]} |
| 10 | MPLA | Monophosphoryl Lipid A |

TABLE II

Examples of Helper Lipids.

| No. | Abbreviation | Name |
|---|---|---|
| 1 | DOTAP | 1,2-dioleoyl-3-trimethylammonium-propane (chloride salt) |
| 2 | DODMA | 1,2-dioleyloxy-3-dimethylaminopropane |
| 3 | DLinDMA | 1,2-dilinoleyloxy-3-dimethylaminopropane |
| 4 | DLin-KC2-DMA | 2,2-dilinoleyl-4-dimethylaminoethyl-[1,3]-dioxolane |
| 5 | Δ9-Cis PE (DOPE) | 1,2-Dioleoyl-sn-glycero-3-phosphoethanolamine |
| 6 | DOPC | 1,2-dioleoyl-sn-glycero-3-phosphocholine |
| 7 | CHOL | Cholesterol |
| 8 | PEG-C-DMA | N-[(methoxy poly(ethylene glycol)2000)carbamyl]-1,2-dimyristyloxlpropyl-3-amine |
| 9 | CHEMS | cholesteryl hemisuccinate |
| 10 | DPPC | 1,2-dipalmitoyl-sn-glycero-3-phosphocholine |
| 11 | DSPC | 1,2-distearoyl-sn-glycero-3-phosphocholine |
| 12 | MO-CHOL | 4-(2-aminoethyl)-morpholino-cholesterolhemisuccinate |
| 13 | DSPE-PEG(2000) Carboxylic Acid | (1,2-distearoyl-sn-glycero-3-phosphoethanolamine-N-[carboxy(polyethylene glycol) |
| 14 | Hydro Soy PC ("HSPC") | L-α-phosphatidylcholine, hydrogenated (Soy) powder |

TABLE III

Examples of Phospholipids/Fatty Acids.

| No. | Name |
|---|---|
| 1 | Oleic acid |
| 2 | linolenic acid |
| 3 | arachidonic acid |
| 4 | docosahexaenoic (DHA) |
| 5 | Palmitic acid |
| 6 | Palmitoleic acid |
| 7 | Stearic acid |
| 8 | Eicosapentaenoic acid (EPA) |
| 9 | DSPE-PEG(2000) Carboxylic Acid (1,2-distearoyl-sn-glycero-3-phosphoethanolamine-N-[carboxy(polyethylene glycol) |
| 10 | DOPE-PEG(2000) Carboxylic acid (1,2-dioleoyl-sn-glycero-3-phosphoethanolamine-N-[carboxy(polyethylene glycol)-2000] (sodium salt) |

TABLE IV

Summary of LNP-TB4 Co-Formulations.

| Nano-formulation | Size in nm diameter | PDI | Zeta potential (mV) |
|---|---|---|---|
| LNP-TB4-PD3 | 91.4 | 0.148 | −12.1 |
| LNP-TB4-ID3 | 87.29 | 0.075 | −11.5 |
| LNP-TB4-TR5 | 101.4 | 0.136 | −11.1 |

TABLE V

Summary of SLNP-TB4 Formulations and Co-Formulations.

| Nano-formulation | Different Stabilizers used | Size in nm diameter | PDI | Zeta potential (mV) |
|---|---|---|---|---|
| SLNP-TB4 | Moliwol 488 | 89.42 | 0.074 | −11.9 |
| SLNP-TB4 | Pluronic F127 | 92.35 | 0.129 | −12.1 |
| SLNP-TB4 | Kolliphor RH 40 | 73.88 | 0.124 | −16.4 |
| SLNP-TB4-ID3 | Moliwol 488 | 104.3 | 0.119 | −10.3 |
| SLNP-TB4-ID3 | Pluronic F127 | 95.6 | 0.146 | −9.8 |
| SLNP-TB4-MPLA | Moliwol 488 | 108.2 | 0.138 | −14.8 |

The invention claimed is:

1. A method of treating a subject suffering or diagnosed with cancer comprising, (i) administering to a subject in need of such treatment an effective amount of a nanocarrier, wherein the nanocarrier comprises a TB prodrug; and (ii) a pharmaceutically acceptable salt thereof.

2. The method of claim 1, wherein the TB prodrug comprises TB4.

3. The method of claim 2, wherein the TB4 has the following chemical structure:

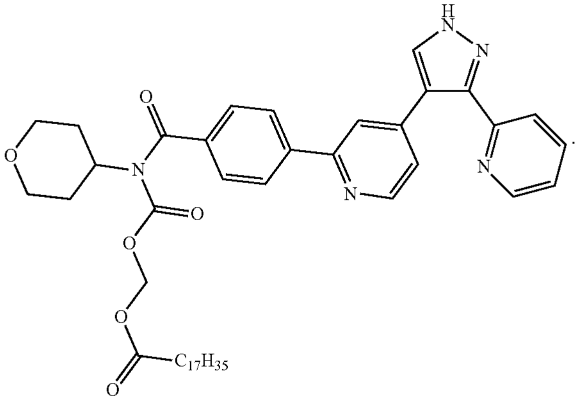

4. The method of claim 1, wherein the nanocarrier comprises TB4 further co-formulated with and ICD-inducing chemotherapeutic.

5. The method of claim 4, wherein the ICD-inducing chemotherapeutic is selected from the group consisting of DOX, MTO, OXA, CP, Bortezomib, Carfilzomib, or Paclitaxel.

6. The method of claim 1, wherein the nanocarrier comprises TB4 further co-formulated with an immune modulating agent.

7. The method of claim 6, wherein the immune modulating agent is selected from the group consisting of other TLR agonists, immunogenic-cell death inducing chemotherapeutics, IDO antagonists, STING agonists, CTLA-4 inhibitors, and PD-1/PD-L1 inhibitors.

8. The method of claim 6, whereby the immune modulating agent is a toll-receptor agonist, and wherein the toll-receptor agonist is selected from the group consisting of Resiquimod (R848), Gardiquimod, 852A, DSR 6434, Telratolimod, CU-T12-9, monophosphoryl Lipid A (MPLA), Monophosphoryl Hexa-acyl Lipid A, 3-Deacyl (Synthetic), SMU127, Pam3CSK4, and 3-deacyl-phosphorylated hexa-acyl disaccharide.

9. The method of claim 6, whereby the immune modulating agent is a PD-1/PD-L1 antagonist, and wherein the PD-1/PD-L1 antagonist is selected from the group consisting of AUNP12, CA-170, and BMS-986189.

10. The method of claim 1, wherein the nanocarrier comprises a liposome.

11. The method of claim 10, wherein the liposome is LNP-TB4.

12. The method of claim 10, wherein the liposome is LNP-TB4-PD3.

13. The method of claim 10, wherein the liposome is LNP-TB4-ID3.

14. The method of claim 10, wherein the liposome is LNP-TB4-TR5.

15. The method of claim 1, wherein the nanocarrier comprises a solid-lipid nanoparticle (SLNP).

16. The method of claim 15, wherein the SLNP is SLNP-TB4.

17. The method of claim 15, wherein the SLNP is SLNP-TB4-ID3.

18. The method of claim 15, wherein the SLNP is SLNP-TB4-MPLA.

19. The method of claim 1, wherein the subject is a human.

20. The method of claim 1, wherein the cancer is melanoma.

21. A kit comprising a nanocarrier, wherein the nanocarrier comprises TB4 further co-formulated with and ICD-inducing chemotherapeutic-4.

22. A kit comprising a nanocarrier, wherein the nanocarrier comprises TB4 further co-formulated with and toll-receptor agonist.

* * * * *